(12) United States Patent
Wong et al.

(10) Patent No.: US 8,450,355 B2
(45) Date of Patent: *May 28, 2013

(54) COMPOUNDS FOR THE TREATMENT OF INFLAMMATORY DISEASES

(75) Inventors: Michael K. C. Wong, Somerset, NJ (US); Wensheng Yu, Edison, NJ (US); Ling Tong, Warren, NJ (US); Brian J. Lavey, New Providence, NJ (US); Bandarpalle B. Shankar, Branchburg, NJ (US); Joseph A. Kozlowski, Princeton, NJ (US); Seong Heon Kim, Livington, NJ (US); Guowei Zhou, Somerset, NJ (US); De-Yi Yang, Morris Plains, NJ (US); Razia K. Rizvi, Bloomfield, NJ (US); Lei Chen, Roselle Park, NJ (US); Aneta Maria Kosinzki, South Amboy, NJ (US); Kristin E. Rosner, Watertown, NJ (US); Luke Fire, Cambridge, MA (US); Judson E. Richard, Kittery, ME (US); Dansu Li, Reading, MA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/120,730

(22) PCT Filed: Sep. 22, 2009

(86) PCT No.: PCT/US2009/057805
§ 371 (c)(1),
(2), (4) Date: Aug. 12, 2011

(87) PCT Pub. No.: WO2010/036640
PCT Pub. Date: Apr. 1, 2010

(65) Prior Publication Data
US 2011/0288077 A1    Nov. 24, 2011

Related U.S. Application Data

(60) Provisional application No. 61/099,732, filed on Sep. 24, 2008.

(51) Int. Cl.
*A61K 31/4166* (2006.01)
*A61K 31/4178* (2006.01)
*C07D 233/02* (2006.01)

(52) U.S. Cl.
USPC .................................... 514/397; 548/311.1

(58) Field of Classification Search
USPC .................................... 548/311.1; 514/397
See application file for complete search history.

(56) References Cited

U.S. PATENT DOCUMENTS

| | | | |
|---|---|---|---|
| 6,495,565 B2 | 12/2002 | Duan et al. |
| 6,534,491 B2 | 3/2003 | Levin et al. |
| 6,677,355 B1 | 1/2004 | Conrad et al. |
| 7,041,693 B2 | 5/2006 | Sheppeck |
| 7,482,370 B2 | 1/2009 | Yu et al. |
| 7,488,745 B2 | 2/2009 | Yu et al. |
| 7,504,424 B2 | 3/2009 | Yu et al. |
| 7,524,842 B2 | 4/2009 | Lavey et al. |
| 7,683,085 B2 | 3/2010 | Yu et al. |
| 7,687,527 B2 | 3/2010 | Yu et al. |
| 7,772,263 B2 | 8/2010 | Lavey et al. |
| 7,879,890 B2 | 2/2011 | Yu et al. |
| 7,998,961 B2 | 8/2011 | Mansoor et al. |
| 8,178,553 B2 | 5/2012 | Lavey et al. |
| 2012/0010181 A1 | 1/2012 | Kozlowski et al. |
| 2012/0015926 A1 | 1/2012 | Tong et al. |

FOREIGN PATENT DOCUMENTS

| | | |
|---|---|---|
| WO | WO02/074750 A1 | 9/2002 |
| WO | WO02/096426 A1 | 12/2002 |
| WO | WO03/053940 A1 | 7/2003 |
| WO | WO03/053941 A2 | 7/2003 |
| WO | WO2004/012663 A2 | 2/2004 |
| WO | WO2004/024698 A1 | 3/2004 |
| WO | WO2004/024715 A1 | 3/2004 |
| WO | WO2004/024721 A1 | 3/2004 |
| WO | WO2004/056766 A1 | 7/2004 |
| WO | WO-2006/019768 | * 2/2006 |

OTHER PUBLICATIONS

Copending U.S. Appl. No. 13/120,728, commonly assigned.*
PCT International Search Report dated Jun. 22, 2010 for corresponding PCT Application No. PCT/US2009/057805.
Knaggs, A., et al., "Biotransformation of Alosetron: Mechanism of Hydantoin Formation", Tetrahedron Letters, vol. 36, No. 3, pp. 477-480 (1995).

* cited by examiner

*Primary Examiner* — Kamal Saeed
*Assistant Examiner* — Janet L Coppins
(74) *Attorney, Agent, or Firm* — Eric A. Meade; Valerie J. Camara

(57) ABSTRACT

This invention relates to compounds of the Formula (I)-(IX):, as defined herein, or a pharmaceutically acceptable salt, solvate or ester thereof, which can be useful for the treatment of diseases or conditions mediated by MMPs, ADAMs, TACE, aggrecanase, TNF-α combinations thereof.

Formula (I)

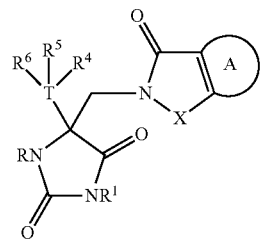

Formula (II)
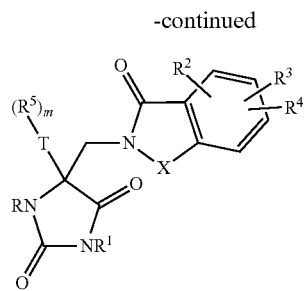
Formula (III)
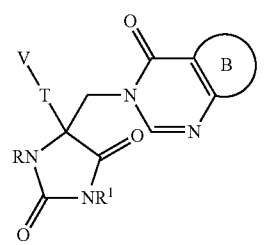
Formula (IV)
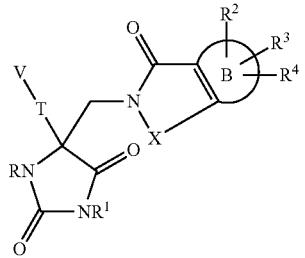
Formula (VI)
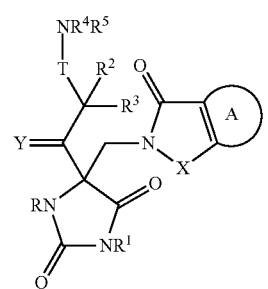
Formula (VII)
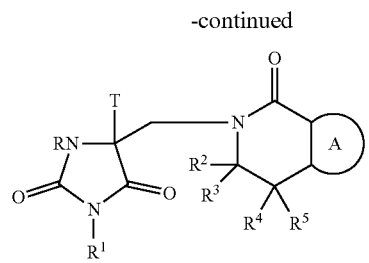
Formula (VIII)
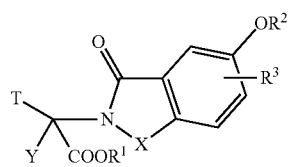
Formula (IX)
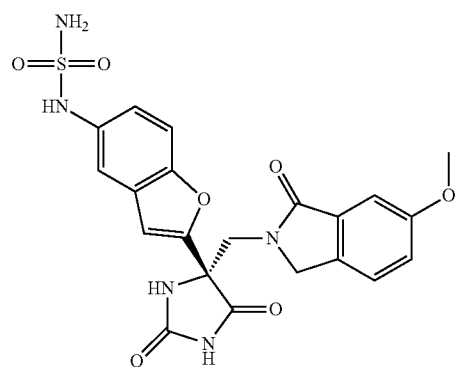
Formula (V)
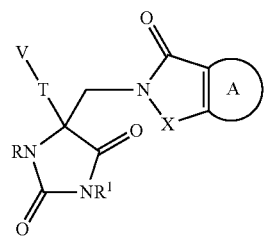
19 Claims, No Drawings

COMPOUNDS FOR THE TREATMENT OF INFLAMMATORY DISEASES

CROSS-REFERENCE TO RELATED APPLICATIONS

This application claims the benefit of priority of U.S. Provisional Application No. 61/099,732, filed Sep. 24, 2008, which is herein incorporated by reference in its entirety.

BACKGROUND OF THE INVENTION

1. Field of the Invention

This invention relates generally to novel hydantoin derivatives that can inhibit matrix metalloproteinases (MMPs), a disintegrin and metalloproteases (ADAMs) and/or tumor necrosis factor alpha-converting enzyme (TACE) and in so doing prevent the release of tumor necrosis factor alpha (TNF-α), pharmaceutical compositions comprising such compounds, and methods of treatment using such compounds.

2. Description

Osteo- and rheumatoid arthritis (OA and RA, respectively) are destructive diseases of articular cartilage characterized by localized erosion of the cartilage surface. Findings have shown that articular cartilage from the femoral heads of patients with OA, for example, had a reduced incorporation of radiolabeled sulfate over controls, suggesting that there must be an enhanced rate of cartilage degradation in OA (Mankin et al. J. Bone Joint Surg. 52A (1970) 424-434). There are four classes of protein degradative enzymes in mammalian cells: serine, cysteine, aspartic and metalloproteases. The available evidence supports the belief that it is the metalloproteases that are responsible for the degradation of the extracellular matrix of articullar cartilage in OA and RA. Increased activities of collagenases and stromelysin have been found in OA cartilage and the activity correlates with severity of the lesion Nankin et al. Arthritis Rheum. 21, 1978, 761-766, Woessner et al. Arthritis Rheum. 26, 1983, 63-68 and Ibid. 27, 1984, 305-312). In addition, aggrecanase (a newly identified metalloprotease) has been identified that provides the specific cleavage product of proteoglycan, found in RA and OA patients (Lohmander L. S. et al. Arthritis Rheum. 36, 1993, 1214-22).

Metalloproteases (MPs) have been implicated as the key enzymes in the destruction of mammalian cartilage and bone. It can be expected that the pathogenesis of such diseases can be modified in a beneficial manner by the administration of MP inhibitors (see Wahl et al. Ann. Rep. Med. Chem. 25, 175-184, AP, San Diego, 1990).

MMPs are a family of over 20 different enzymes that are involved in a variety of biological processes important in the uncontrolled breakdown of connective tissue, including proteoglycan and collagen, leading to resorption of the extracellular matrix. This is a feature of many pathological conditions, such as RA and OA, corneal, epidermal or gastric ulceration; tumor metastasis or invasion; periodontal disease and bone disease. Normally these catabolic enzymes are tightly regulated at the level of their synthesis as well as at their level of extracellular activity through the action of specific inhibitors, such as alpha-2-macroglobulins and TIMPs (tissue inhibitor of MPs), which form inactive complexes with the MMP's.

Tumor necrosis factor alpha (TNF-α) is a cell-associated cytokine that is processed from a 26 kDa precursor form to a 17 kd active form. See Black R. A. "Tumor necrosis factor-alpha converting enzyme" Int J Biochem Cell Biol. 2002 January; 34(1):1-5 and Moss M L, White J M, Lambert M H, Andrews R C. "TACE and other ADAM proteases as targets for drug discovery" Drug Discov Today. 2001 Apr. 1; 6(8): 417-426, each of which is incorporated by reference herein.

TNF-α has been shown to play a pivotal role in immune and inflammatory responses. Inappropriate or over-expression of TNF-α is a hallmark of a number of diseases, including RA, Crohn's disease, multiple sclerosis, psoriasis and sepsis. Inhibition of TNF-α production has been shown to be beneficial in many preclinical models of inflammatory disease, making inhibition of TNF-α production or signaling an appealing target for the development of novel anti-inflammatory drugs.

TNF-α is a primary mediator in humans and animals of inflammation, fever and acute phase responses, similar to those observed during acute infection and shock, Excess TNF-α has been shown to be lethal. Blocking the effects of TNF-α with specific antibodies can be beneficial in a variety of conditions, including autoimmune diseases such as RA (Feldman et al, Lancet, (1994) 344, 1105), non-insulin dependent diabetes mellitus (Lohmander L. S. et al., Arthritis Rheum. 36 (1993) 1214-22) and Crohn's disease (Macdonald T. et al., Clin. Exp. Immunol. 81 (1990) 301).

Compounds that inhibit the production of TNF-α are therefore of therapeutic importance for the treatment of inflammatory disorders. Recently it has been shown that metalloproteases, such as TACE, are capable of converting TNF-α from its inactive to active form (Gearing et al Nature, 1994, 370, 555). Since excessive TNF-α production has been noted in several disease conditions also characterized by MMP-mediated tissue degradation, compounds which inhibit both MMPs and TNF-α production may also have a particular advantage in diseases where both mechanisms are involved.

One approach to inhibiting the harmful effects of TNF-α is to inhibit the enzyme, TACE before it can process TNF-α to its soluble form. TACE is a member of the ADAM family of type I membrane proteins and mediates the ectodomain shedding of various membrane-anchored signaling and adhesion proteins. TACE has become increasingly important in the study of several diseases, including inflammatory disease, because of its role in cleaving TNF-α from its "stalk" sequence and thus releasing the soluble form of the TNF-α protein (Black R. A. Int J Biochem Cell Biol. 2002 34, 1-5).

There are numerous patents and publications which disclose hydroxamate, sulphonamide, hydantoin, carboxylate and/or lactam based MMP inhibitors.

U.S. Pat. No. 6,677,355 and U.S. Pat. No. 6,534,491(B2), describe compounds that are hydroxamic acid derivatives and MMP inhibitors.

U.S. Pat. No. 6,495,565 discloses lactam derivatives that are potential inhibitors of MMPs and/or TNF-α.

PCT Publications WO2002/074750, WO2002/096426, WO20040067996, WO2004012663, WO200274750 and WO2004024721 disclose hydantoin derivatives that are potential inhibitors of MMPs.

PCT Publications WO2004024698 and WO2004024715 disclose sulphonamide derivatives that are potential inhibitors of MMPs.

PCT Publications WO2004056766, WO2003053940 and WO2003053941 also describe potential inhibitors of TACE and MMPs.

PCT Publications WO 2006/019768, WO 2007/084415, WO 2007/084451, and WO 2007/084455 refer to hydantoin derivatives that are TACE inhibitors.

There is a need in the art for inhibitors of MMPs, ADAMs, TACE, and TNF-α, which can be useful as anti-inflammatory compounds and cartilage protecting therapeutics. The inhibition of TNF-α, TACE and or other MMPs can prevent the degradation of cartilage by these enzymes, thereby alleviating the pathological conditions of OA and RA as well as many other auto-immune diseases.

SUMMARY OF THE INVENTION

In its many embodiments, the present invention provides a novel class of compounds as inhibitors of TACE, the production of TNF-α, MMPs, ADAMs, aggrecanase, or any combination thereof, methods of preparing such compounds, pharmaceutical compositions comprising one or more such compounds, methods of preparing pharmaceutical formulations comprising one or more such compounds, and methods of treatment, prevention, inhibition or amelioration of one or more diseases associated with TACE, aggrecanaseTNF-α, MMPs, ADAMs or any combination thereof using such compounds or pharmaceutical compositions.

In one embodiment, the present application discloses a compound represented by Formula (I):

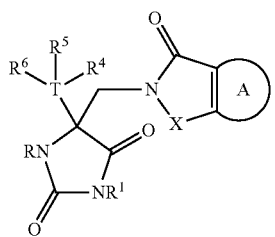

Formula (I)

or a pharmaceutically acceptable salt or solvate thereof, wherein:

ring A is aryl or heteroaryl, wherein said aryl or heteroaryl is unsubstituted or substituted with $R^2$ or $—OR^3$, wherein $R^2$ is H or halo, and $R^3$ is H or alkyl;

T is aryl or heteroaryl, substituted with an $R^4$, $R^5$, and $R^6$ as shown;

X is selected from the group consisting of —S—, —O—, —S(O)$_2$—, —S(O)—, —(CR$^8_2$)$_p$— and —N(R')—;

p is 1 to 3;

R' is selected from the group consisting of H, alkyl, and aryl;

R is selected from the group consisting of H, alkyl, cycloalkyl, cycloalkenyl, heterocyclyl, heterocyclenyl, aryl, heteroaryl, —C(═O)alkyl, —C(═O)cycloalkyl, —C(═O)heterocyclyl, —C(═O)aryl, —C(═O)heteroaryl, —C(═O)O-alkyl, —C(═O)O-cycloalkyl, —C(═O)O-heterocyclyl, —C(═O)O-aryl, and —C(═O)O-heteroaryl;

$R^1$ is selected from the group consisting of H and —C($R^7$)$_2$-(Q)$_n R^9$;

$R^4$ is selected from the group consisting of H, alkyl, and halogen;

$R^5$ and $R^6$ are substituents on adjacent carbon atoms, wherein $R^5$ and $R^6$ together with the carbon atoms to which they are attached form a first five- to eight-membered cycloalkyl, cycloalkenyl, heterocyclyl, or heterocyclenyl; wherein said first five- to eight-membered cycloalkyl, cycloalkenyl, heterocyclyl, or heterocyclenyl contains two radicals on the same carbon atom, and said radicals taken together with the carbon atom to which they are attached form a second five- to eight-membered cycloalkyl, cycloalkenyl, heterocyclyl, or heterocyclenyl; wherein said first five- to eight-membered cycloalkyl, cycloalkenyl, heterocyclyl, or heterocyclenyl, optionally with said second five- to eight-membered cycloalkyl, cycloalkenyl, heterocyclyl, or heterocyclenyl is unsubstituted or substituted with one to four $R^{10}$ moieties;

each $R^7$ independently is selected from the group consisting of H, alkyl, and aryl;

each $R^8$ independently is selected from the group consisting of H, alkyl, and aryl;

$R^9$ is selected from the group consisting of H, alkyl, heterocyclyl, aryl, heteroaryl, —C(═O)N($R^{12}$)$_2$, —C(═O)-alkyl, C(═O)-cycloalkyl, C(═O)-heterocyclyl, —C(═O)-aryl, —C(═O)-heteroaryl, —C(═O)—O-alkyl, —C(═O)—O-cycloalkyl, —C(═O)—O-heterocyclyl, —C(═O)—O-aryl, —C(═O)—O-heteroaryl, —P(═O)(—OH)$_2$, —P(═O)(—O-alkyl)$_2$, wherein when each of said "cycloalkyl", "heterocyclyl", "aryl", or "heteroaryl" in any of the aforementioned $R^9$ groups contains two radicals on adjacent carbon atoms, said radicals may optionally be taken together with the carbon atoms to which they are attached to form a five- or six-membered cycloalkyl, aryl, heterocyclyl or heteroaryl ring;

each $R^{10}$ is independently selected from the group consisting of cyano, nitro, —OC(O)$R^{11}$, —C($R^{11}$)═N—O$R^{11}$, —S$R^{11}$, —N($R^{11}$)$_2$, —S(O)$R^{11}$, —S(O)$_2 R^{11}$, —N($R^{11}$)S(O)$_2 R^{11}$, —N($R^{11}$)—C(O)—$R^{11}$, —N($R^{11}$)—C(O)—N($R^{11}$)$_2$, —N($R^{11}$)—C(O)—O$R^{11}$, —OC(O)N($R^{11}$)$_2$, —C(O)N($R^{11}$)—S(O)$_2 R^{11}$, —S(O)$_2$N($R^{11}$)—C(O)—$R^{11}$, —C(O)N($R^{11}$)C(O)$R^{11}$, —C(O)N($R^{11}$)C(O)N$R^{11}$, —S(O)$_2$N($R^{11}$)$_2$, —N($R^{11}$)—C(═N$R^{11}$)—N($R^{11}$)$_2$, —N($R^{11}$)—C(═N—CN)—N($R^{11}$)$_2$, -haloalkoxy, —C(O)O$R^{11}$, —C(O)$R^{11}$, —C(O)N($R^{11}$)$_2$, halogen, alkyl, haloalkyl, aryl, heteroaryl, heterocyclyl, heterocyclenyl, cycloalkenyl, and cycloalkyl, with the proviso that there are no adjacent heteroatoms in any of said $R^{10}$;

each $R^{11}$ independently is selected from the group consisting of H, alkyl, cycloalkyl, haloalkyl, hydroxy, heterocyclyl, aryl, and heteroaryl;

Q is selected from the group consisting of —N$R^{12}$—, —O—, —S—, —S(O)—, and —S(O)$_2$—;

each $R^{12}$ is independently selected from the group consisting of H and alkyl; and n is 0 or 1.

In another embodiment, the present application discloses a compound represented by Formula (II):

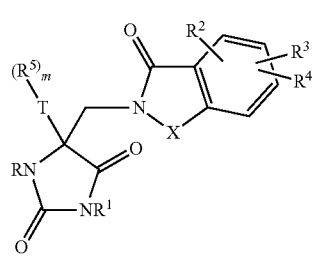

Formula (II)

or a pharmaceutically acceptable salt or solvate thereof, wherein:

T is aryl or heteroaryl, each of which is substituted with m $R^5$ substituents as shown;

X is selected from the group consisting of —S—, —O—, —S(O)$_2$—, —S(O)—, —(CR$^6_2$)$_p$— and —N(R')—;

p is 1 to 3;

R' is selected from the group consisting of H, alkyl, and aryl;

R is selected from the group consisting of H, alkyl, cycloalkyl, cycloalkenyl, heterocyclyl, heterocyclenyl, aryl, heteroaryl, —C(=O)alkyl, —C(=O)cycloalkyl, —C(=O)heterocyclyl, —C(=O)aryl, —C(=O)heteroaryl, —C(=O)O-alkyl, —C(=O)O-cycloalkyl, —C(=O)O-heterocyclyl, —C(=O)O-aryl, and —C(=O)O-heteroaryl;

$R^1$ is selected from the group consisting of H and —C($R^6$)$_2$-(Q)$_n R^7$;

$R^2$ is selected from the group consisting of H, alkyl, and halogen;

$R^3$ and $R^4$ are substituents on adjacent carbon atoms, wherein $R^3$ and $R^4$ together with the carbon atoms to which they are attached form a first five or six-membered heteroaryl, which is unsubstituted or substituted with one or two substituents independently selected from the group consisting of alkyl and cycloalkyl;

$R^5$ is selected from the group consisting of alkyl, cycloalkyl, heterocyclyl, aryl and heteroaryl;

each $R^6$ independently is selected from the group consisting of H, alkyl, and aryl;

$R^7$ is selected from the group consisting of H, alkyl, heterocyclyl, aryl, heteroaryl, —C(=O)N($R^8$)$_2$, —C(=O)-alkyl, C(=O)-cycloalkyl, C(=O)-heterocyclyl, —C(=O)-aryl, —C(=O)-heteroaryl, —C(=O)—O-alkyl, —C(=O)—O-cycloalkyl, —C(=O)—O-heterocyclyl, —C(=O)—O-aryl, —C(=O)—O-heteroaryl, —P(=O)(—OH)$_2$, —P(=O)(—O-alkyl)$_2$, wherein when each of said "cycloalkyl", "heterocyclyl", "aryl", or "heteroaryl" in any of the aforementioned $R^9$ groups contains two radicals on adjacent carbon atoms, said radicals may optionally be taken together with the carbon atoms to which they are attached to form a five- or six-membered cycloalkyl, aryl, heterocyclyl or heteroaryl ring;

each $R^8$ is independently selected from the group consisting of H and alkyl;

Q is selected from the group consisting of —$NR^8$—, —O—, —S—, —S(O)—, and —S(O)$_2$—;

n is 0 or 1; and m is 0-3.

In another embodiment, the present application discloses a compound represented by Formula (III):

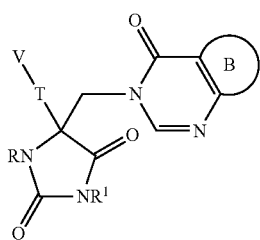

Formula (III)

or a pharmaceutically acceptable salt or solvate thereof, wherein:

ring B is aryl or heteroaryl, wherein said aryl or heteroaryl is unsubstituted or substituted with alkoxy;

at least one of T and V is present;

T is absent or present, and if present, is selected from the group consisting of alkyl, alkenyl, alkynyl, cycloalkyl, cycloalkenyl, aryl, heterocyclyl, heterocyclenyl, and heteroaryl;

V is absent or present, and if present, is selected from the group consisting of alkyl, alkenyl, alkynyl, cycloalkyl, cycloalkenyl, aryl, heterocyclyl, heterocyclenyl, and heteroaryl;

R is selected from the group consisting of H, alkyl, cycloalkyl, cycloalkenyl, heterocyclyl, heterocyclenyl, aryl, heteroaryl, —C(=O)alkyl, —C(=O)cycloalkyl, —C(=O)heterocyclyl, —C(=O)aryl, —C(=O)heteroaryl, —C(=O)—O-alkyl, —C(=O)O-cycloalkyl, —C(=O)O-heterocyclyl, —C(=O)O-aryl, and —C(=O)O-heteroaryl;

$R^1$ is selected from the group consisting of H and —C($R^3$)$_2$-(Q)$_n R^4$;

each $R^3$ independently is selected from the group consisting of H, alkyl and aryl;

$R^4$ is selected from the group consisting of H, alkyl, heterocyclyl, aryl, heteroaryl, —C(=O)N($R^5$)$_2$, —C(=O)-alkyl, C(=O)-cycloalkyl, C(=O)-heterocyclyl, —C(=O)-aryl, —C(=O)-heteroaryl, —C(=O)—O-alkyl, —C(=O)—O-cycloalkyl, —C(=O)—O-heterocyclyl, —C(=O)—O-aryl, —C(=O)—O-heteroaryl, —P(=O)(—OH)$_2$, —P(=O)(—O-alkyl)$_2$, wherein when each of said "cycloalkyl", "heterocyclyl", "aryl", or "heteroaryl" in any of the aforementioned $R^9$ groups contains two radicals on adjacent carbon atoms, said radicals may optionally be taken together with the carbon atoms to which they are attached to form a five- or six-membered cycloalkyl, aryl, heterocyclyl or heteroaryl ring;

Q is selected from the group consisting of —$NR^5$—, —O—, —S—, —S(O)—, and —S(O)$_2$—;

each $R^5$ is independently selected from the group consisting of H and alkyl;

and n is 0 or 1.

In another embodiment, the present application discloses a compound represented by Formula (IV):

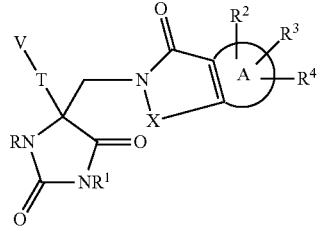

Formula (IV)

or a pharmaceutically acceptable salt or solvate thereof, wherein:

ring A is aryl or heteroaryl, substituted on adjacent ring atoms with $R^2$, $R^3$, and $R^4$;

at least one of T and V is present;

T is absent or present, and if present, is selected from the group consisting of alkyl, alkenyl, alkynyl, cycloalkyl, cycloalkenyl, aryl, heterocyclyl, heterocyclenyl, and heteroaryl;

V is absent or present, and if present, is selected from the group consisting of alkyl, alkenyl, alkynyl, cycloalkyl, cycloalkenyl, aryl, heterocyclyl, heterocyclenyl, and heteroaryl;

X is selected from the group consisting of —S—, —O—, —S(O)$_2$—, —S(O)—, —(C$R^5$$_2$)$_p$— and —N(R')—;

p is 1 to 3;

R' is selected from the group consisting of H, alkyl, and aryl;

R is selected from the group consisting of H, alkyl, cycloalkyl, cycloalkenyl, heterocyclyl, heterocyclenyl, aryl, heteroaryl, —C(=O)alkyl, —C(=O)cycloalkyl, —C(=O)heterocyclyl, —C(=O)aryl, —C(=O)heteroaryl, —C(=O)O-alkyl, —C(=O)O-cycloalkyl, —C(=O)O-heterocyclyl, —C(=O)O-aryl, and —C(=O)O-heteroaryl;

$R^1$ is selected from the group consisting of H and —C($R^6$)$_2$-(Q)$_n$$R^7$;

$R^2$, $R^3$, and $R^4$ are substitutents on adjacent ring atoms, wherein each of $R^2$, $R^3$, and $R^4$ is independently selected from the group consisting of halo, alkyl, and alkoxy;

each $R^5$ independently is selected from the group consisting of H, alkyl, and aryl;

each $R^6$ independently is selected from the group consisting of H, alkyl, and aryl;

$R^7$ is selected from the group consisting of H, alkyl, heterocyclyl, aryl, heteroaryl, —C(=O)N($R^8$)$_2$, —C(=O)-alkyl, C(=O)-cycloalkyl, C(=O)-heterocyclyl, —C(=O)-aryl, —C(=O)-heteroaryl, —C(=O)—O-alkyl, —C(=O)—O-cycloalkyl, —C(=O)—O-heterocyclyl, —C(=O)—O-aryl, —C(=O)—O-heteroaryl, —P(=O)(—OH)$_2$, —P(=O)(—O-alkyl)$_2$, wherein when each of said "cycloalkyl", "heterocyclyl", "aryl", or "heteroaryrl" in any of the aforementioned $R^9$ groups contains two radicals on adjacent carbon atoms, said radicals may optionally be taken together with the carbon atoms to which they are attached to form a five- or six-membered cycloalkyl, aryl, heterocyclyl or heteroaryl ring;

Q is selected from the group consisting of —N$R^8$—, —O—, —S—, and —S(O)$_2$—;

each $R^8$ is independently selected from the group consisting of H and alkyl; and n is 0 or 1.

In another embodiment, the present application discloses a compound represented by Formula (V):

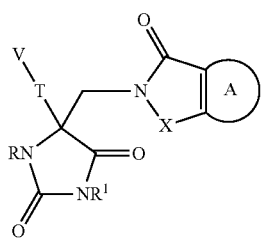

Formula (V)

or a pharmaceutically acceptable salt or solvate thereof, wherein:

ring A is aryl or heteroaryl, wherein said aryl or heteroaryl is unsubstituted or substituted with alkoxy or deuterium;

at least one of T and V is present, and at least one of T and V is substituted with 1-3 $R^2$ substituents;

T is absent or present, and if present is selected from the group consisting of: alkyl, alkenyl, alkynyl, cycloalkyl, cycloalkenyl, aryl, heterocyclyl, heterocyclenyl, and heteroaryl;

V is absent or present, and if present is selected from the group consisting of: alkyl, alkenyl, alkynyl, cycloalkyl, cycloalkenyl, aryl, heterocyclyl, heterocyclenyl, and heteroaryl;

X is selected from the group consisting of —S—, —O—, —S(O)$_2$—, —S(O)—, —(C$R^7$$_2$)$_p$— and —N(R')—;

p is 1 to 3;

R' is selected from the group consisting of H, alkyl, and aryl;

R is selected from the group consisting of H, alkyl, cycloalkyl, cycloalkenyl, heterocyclyl, heterocyclenyl, aryl, heteroaryl, —C(=O)alkyl, —C(=O)cycloalkyl, —C(=O)heterocyclyl, —C(=O)aryl, —C(=O)heteroaryl, —C(=O)O-alkyl, —C(=O)O-cycloalkyl, —C(=O)O-heterocyclyl, —C(=O)O-aryl, and —C(=O)O-heteroaryl;

$R^1$ is selected from the group consisting of H and —C($R^6$)$_2$-(Q)$_n$$R^9$;

Q is selected from the group consisting of —N$R^6$—, —O—, —S—, —S(O)—, and —S(O)$_2$—;

n is 0 or 1;

$R^2$ is selected from the group consisting of deuterium, —C(=N—OH)—N($R^6$)$_2$, —C(=O)N$R^6$S(=O)$_2$N($R^6$)$_2$, —C($R^6$)((C=O)O$R^6$)-heterocyclyl-C(=O)O$R^6$, —C($R^6$)((C=O)N($R^6$)$_2$)-heterocyclyl-C(=O)Oalkyl, —C(=N$R^6$)—N($R^6$)O$R^6$, —C(=N$R^6$)—N($R^6$)-heterocyclyl, —C(=N$R^6$)—N($R^6$)-aryl, —C(=N$R^6$)—N($R^6$)-heteroaryl, —C(=N$R^6$)—N($R^6$)$_2$, and —N$R^6$—C(=S)N($R^6$)-alkyl-heterocyclyl;

each $R^6$ independently is H or alkyl;

each $R^7$ independently is H, alkyl, or aryl;

$R^9$ is selected from the group consisting of H, alkyl, heterocyclyl, aryl, heteroaryl, —C(=O)N($R^6$)$_2$, —C(=O)-alkyl, C(=O)-cycloalkyl, C(=O)-heterocyclyl, —C(=O)-aryl, —C(=O)-heteroaryl, —C(=O)—O-alkyl, —C(=O)—O-cycloalkyl, —C(=O)—O-heterocyclyl, —C(=O)—O-aryl, —C(=O)—O-heteroaryl, —P(=O)(—OH)$_2$, —P(=O)(—O-alkyl)$_2$, wherein when each of said "cycloalkyl", "heterocyclyl", "aryl", or "heteroaryl" in any of the aforementioned $R^9$ groups contains two radicals on adjacent carbon atoms, said radicals may optionally be taken together with the carbon atoms to which they are attached to form a five- or six-membered cycloalkyl, aryl, heterocyclyl or heteroaryl ring.

In another embodiment, the present application discloses a compound represented by Formula (VI):

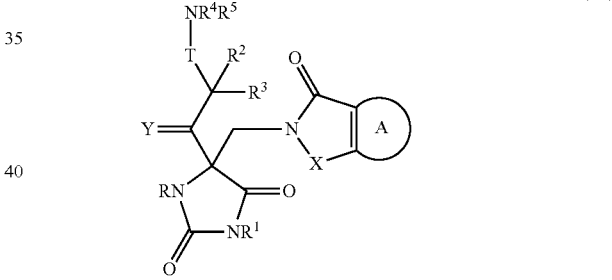

Formula (VI)

or a pharmaceutically acceptable salt or solvate thereof; wherein:

ring A is aryl or heteroaryl, where said aryl or heteroaryl is unsubstituted or is substituted with one or two substituents selected from the group consisting of halo and alkoxy;

X is selected from the group consisting of —S—, —O—, —S(O)$_2$—, —S(O)—, —(C$R^7$$_2$)$_p$— and —N(R')—;

p is 1 to 3;

Y is O or S;

T is aryl or heteroaryl;

R' is selected from the group consisting of H, alkyl, and aryl;

R is selected from the group consisting of H, alkyl, cycloalkyl, cycloalkenyl, heterocyclyl, heterocyclenyl, aryl, heteroaryl, —C(=O)alkyl, —C(=O)cycloalkyl, —C(=O)heterocyclyl, —C(=O)aryl, —C(=O)heteroaryl, —C(=O)-alkyl, —C(=O)O-cycloalkyl, —C(=O)O-heterocyclyl, —C(=O)O-aryl, and —C(=O)-heteroaryl;

$R^1$ is selected from the group consisting of H and —C($R^6$)$_2$-(Q)$_n$$R^9$;

Q is selected from the group consisting of —N$R^6$—, —O—, —S—, —S(O)—, and —S(O)$_2$—;

n is 0 or 1;

each of $R^1$ and $R^2$ is independently H or alkyl;

each of $R^4$ and $R^5$ is independently selected from the group consisting of H, alkyl, cycloalkyl, heterocyclyl, aryl, and heteroaryl;

or wherein $R^4$ and $R^5$ together with the nitrogen atom to which they are shown attached form a heterocyclyl or heteroaryl ring;

each $R^6$ independently is H or alkyl;

each $R^7$ independently is H, alkyl or aryl; and $R^9$ is selected from the group consisting of H, alkyl, heterocyclyl, aryl, heteroaryl, —C(=O)N($R^6$)$_2$, —C(=O)-alkyl, C(=O)-cycloalkyl, C(=O)-heterocyclyl, —C(=O)-aryl, —C(=O)-heteroaryl, —C(=O)—O-alkyl, —C(=O)—O-cycloalkyl, —C(=O)—O-heterocyclyl, —C(=O)—O-aryl, —C(=O)—O-heteroaryl, —P(=O)(—OH)$_2$, —P(=O)(—O-alkyl)$_2$, wherein when each of said "cycloalkyl", "heterocyclyl", "aryl", or "heteroaryl" in any of the aforementioned $R^9$ groups contains two radicals on adjacent carbon atoms, said radicals may optionally be taken together with the carbon atoms to which they are attached to form a five- or six-membered cycloalkyl, aryl, heterocyclyl or heteroaryl ring.

In another embodiment, the present application discloses a compound represented by Formula (VII):

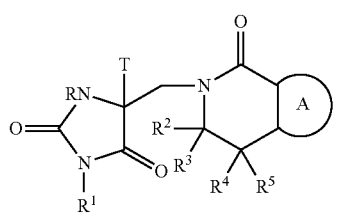

Formula (VII)

or a pharmaceutically acceptable salt or solvate thereof; wherein:

ring A is aryl, wherein said aryl is unsubstituted or substituted with alkoxy;

T is heteroaryl, wherein when said T heteroaryl contains two radicals on adjacent carbon atoms, said radicals may optionally be taken together with the carbon atoms to which they are attached to form a five- to eight membered heterocyclyl ring;

R is selected from the group consisting of H, alkyl, cycloalkyl, cycloalkenyl, heterocyclyl, heterocyclenyl, aryl, heteroaryl, —C(=O)alkyl, —C(=O)cycloalkyl, —C(=O) heterocyclyl, —C(=O)aryl, —C(=O)heteroaryl, —C(=O)O-alkyl, —C(=O)O-cycloalkyl, —C(=O)O-heterocyclyl, —C(=O)O-aryl, and —C(=O)O-heteroaryl;

$R^1$ is selected from the group consisting of H and —C($R^6$)$_2$-(Q)$_n$$R^7$;

each of $R^2$, $R^3$, $R^4$, and $R^5$ independently is H or alkyl;

each $R^6$ independently is H or alkyl;

$R^7$ is selected from the group consisting of H, alkyl, heterocyclyl, aryl, heteroaryl, —C(=O)N($R^6$)$_2$, —C(=O)-alkyl, C(=O)-cycloalkyl, C(=O)-heterocyclyl, —C(=O)-aryl, —C(=O)-heteroaryl, —C(=O)—O-alkyl, —C(=O)—O-cycloalkyl, —C(=O)—O-heterocyclyl, —C(=O)—O-aryl, —C(=O)—O-heteroaryl, —P(=O)(—OH)$_2$, —P(=O)(—O-alkyl)$_2$, wherein when each of said "cycloalkyl", "heterocyclyl", "aryl", or "heteroaryl" in any of the aforementioned $R^7$ groups contains two radicals on adjacent carbon atoms, said radicals may optionally be taken together with the carbon atoms to which they are attached to form a five- or six-membered cycloalkyl, aryl, heterocyclyl or heteroaryl ring; and Q is selected from the group consisting of —NR$^6$—, —O—, —S—, —S(O)—, and —S(O)$_2$—; and n is 0 or 1.

In another embodiment, the present application discloses a compound represented by Formula (VIII):

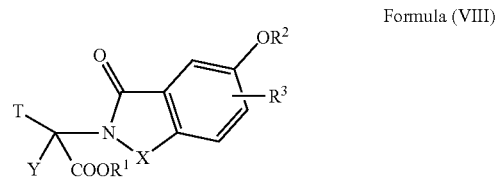

Formula (VIII)

or a pharmaceutically acceptable salt or solvate thereof; wherein:

X is selected from the group consisting of —S(O)$_2$—, —S(O)—, —(CR$^7$$_2$)$_p$— and —N(R')—;

R' is selected from the group consisting of H, alkyl, and aryl;

T is heteroaryl, wherein said heteroaryl is unsubstituted or substituted with a halo;

Y is selected from the group consisting of —OR$^6$, —N(R$^6$)$_2$, and —NR$^6$—C(=O)N(R$^6$)$_2$;

each of $R^1$ and $R^2$ is independently H or alkyl;

$R^3$ is selected from the group consisting of H or halo;

each $R^6$ independently is H or alkyl;

each $R^7$ independently is H, alkyl or aryl;

and p is 1-3.

In another embodiment, the present application discloses a compound represented by Formula (IX):

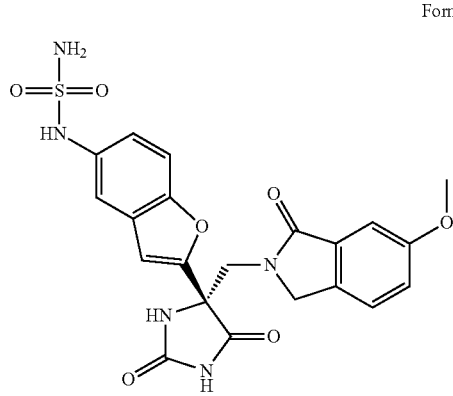

Formula (IX)

or a pharmaceutically acceptable salt or solvate thereof.

The compounds of Formulae (I)-(IX) can be useful as inhibitors of TACE and may be useful in the treatment and prevention of diseases associated with TACE, TNF-α, MMPs, ADAMs or any combination thereof.

DETAILED DESCRIPTION OF THE INVENTION

In its several embodiments, the present invention provides a novel class of inhibitors of TACE, aggrecanase, the production of TNF-α, MMPs, ADAMs or any combination thereof, pharmaceutical compositions containing one or more of the compounds, methods of preparing pharmaceutical formulations comprising one or more such compounds, and methods of treatment, prevention or amelioration of one or more of the symptoms of inflammation.

In one embodiment, the present invention provides compounds which are represented by structural Formulae (I)-(IX) above or a pharmaceutically acceptable salt, solvate, ester or isomer thereof, wherein the various moieties are as described above.

In another embodiment, in formula (I), said $T(R^4)(R^5)(R^6)$ is

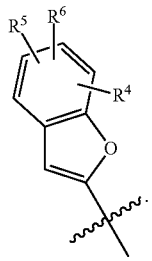

In another embodiment, in formula (I), X is $—(CR^8_2)_p—$.

In another embodiment, in formula (I), ring A is aryl or heteroaryl.

In another embodiment, in formula (I), ring A is aryl or heteroaryl substituted by $—OR^3$ wherein $R^3$ is H or alkyl.

In another embodiment, in formula (I), ring A is aryl or heteroaryl substituted by $—OCH_3$.

In another embodiment, in formula (I), ring A is aryl.

In another embodiment, in formula (I), ring A is phenyl.

In another embodiment, in formula (I), ring A is phenyl substituted by $—OR^3$ wherein $R^3$ is H or alkyl.

In another embodiment, in formula (I), ring A is phenyl substituted by $—OCH_3$.

In another embodiment, in formula (I), X is $—(CR^8_2)_p—$, wherein $R^8$ is H.

In another embodiment, in formula (I), X is $—(CR^8_2)_p—$, wherein p is 1 or 2.

In another embodiment, in formula (I), R is H.

In another embodiment, in formula (I), $R^1$ is H.

In another embodiment, in formula (I), $R^4$ is H.

In another embodiment, in formula (I), $R^5$ and $R^6$ together with the carbon atoms to which they are attached form a five- or six-membered cycloalkyl, wherein said five- or six-membered cycloalkyl contains two radicals on the same carbon atom, said radicals taken together with the carbon atom to which they are attached form a five-membered heterocyclyl.

In another embodiment, in formula (I), $R^5$ and $R^6$ together with the carbon atoms to which they are attached form a five- or six-membered cycloalkyl, wherein said five- or six-membered cycloalkyl contains two radicals on the same carbon atom, said radicals taken together with the carbon atom to which they are attached form a five-membered heterocyclyl, wherein said five- or six-membered cycloalkyl comprising $R^5$ and $R^6$ and further comprising said five-membered heterocyclyl is selected from the group consisting of:

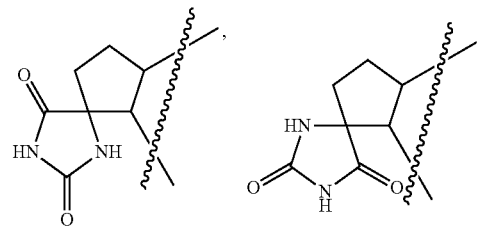

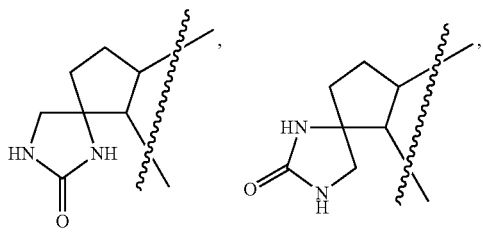

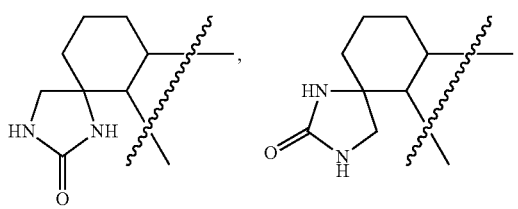

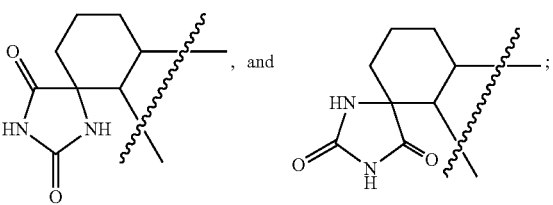

each of which is unsubstituted or independently substituted with one to four $R^{10}$ moieties.

In another embodiment, formula (I), formula (I) is selected from the group consisting of Formula (IA)

Formula (IA)

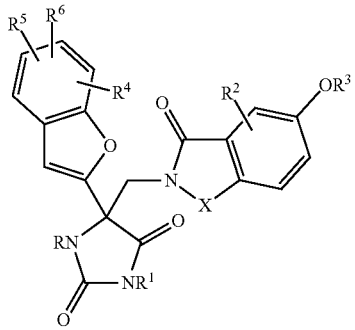

and Formula (IB):

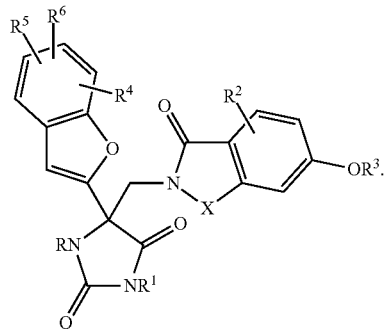
Formula (IB)

wherein in each of Formula (IA) and (IB), $R^2$ is selected from the group consisting of H, alkyl, and halo; and $R^3$ is selected from the group consisting of H and alkyl.

In another embodiment, in formula (IA) or (IB), $R^2$ is selected from the group consisting of H and halo.

In another embodiment, in formula (IA) or (IB), $R^2$ is selected from the group consisting of H and fluoro.

In another embodiment, the compound of formula (I) is selected from the group consisting of:

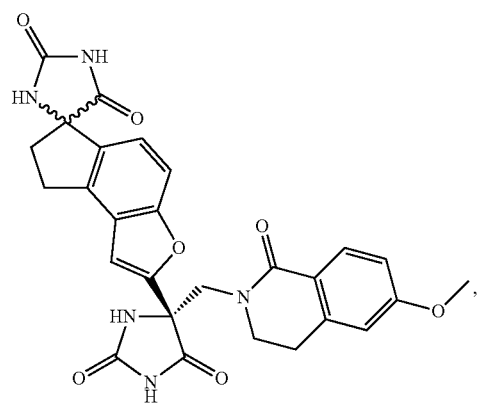

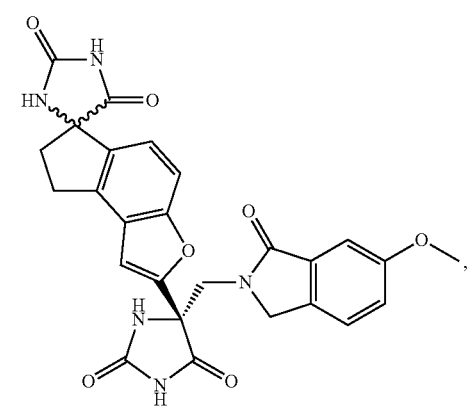

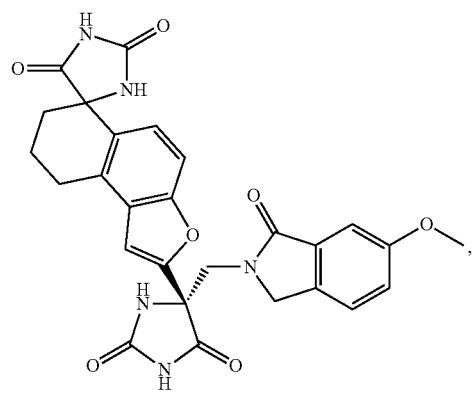

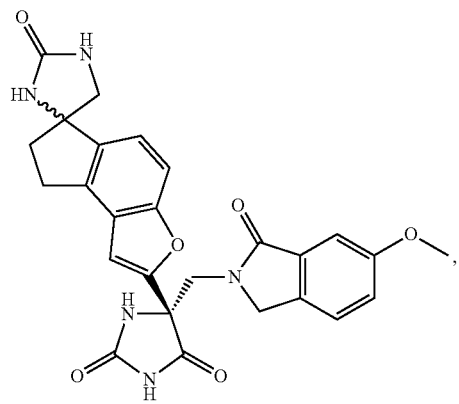

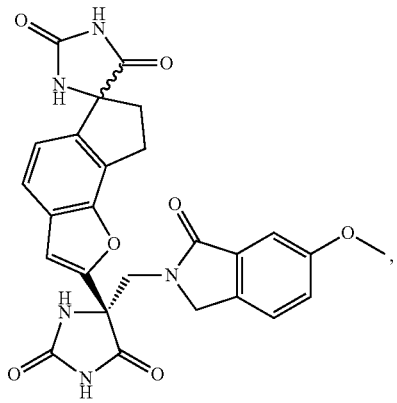

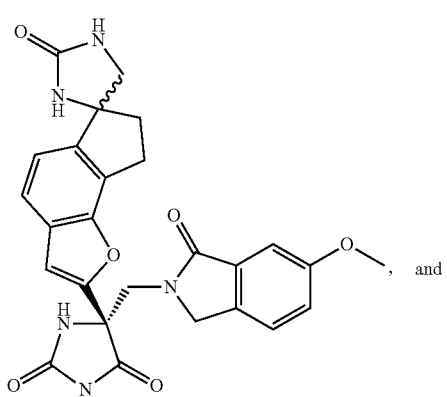

and

-continued

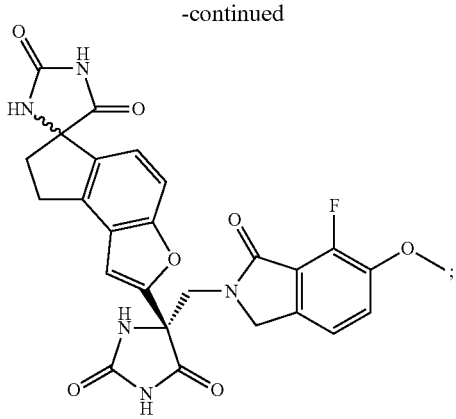

or a pharmaceutically acceptable salt or solvate thereof.

In another embodiment, in formula (II), T is heteroaryl and is represented by

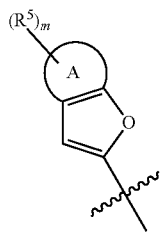

wherein:

ring A is pyridine substituted with m $R^5$ substituents on carbon atoms as shown.

In another embodiment, in formula (II), X is —$(CR^6_2)_p$—.

In another embodiment, in formula (II), X is —$(CR^6_2)_p$—, wherein $R^8$ is H.

In another embodiment, in formula (II), X is —$(CR^6_2)_p$—, wherein p is 1 or 2.

In another embodiment, in formula (II), X is —$(CR^6_2)_p$—, wherein p is 1.

In another embodiment, in formula (II), R is H.

In another embodiment, in formula (II), $R^1$ is H.

In another embodiment, in formula (II), $R^2$ is selected from the group consisting of H and halo.

In another embodiment, in formula (II), $R^2$ is selected from the group consisting of H and fluoro.

In another embodiment, in formula (II), $R^3$ and $R^4$ together with the carbon atoms to which they are attached form a first five or six-membered heteroaryl, which is unsubstituted or substituted with a substituent selected from the group consisting of alkyl, alkoxyalkyl, benzyl, and cycloalkyl.

In another embodiment, in formula (II), $R^3$ and $R^4$ together with the carbon atoms to which they are attached form a furanyl group which is unsubstituted or substituted with a substituent selected from the group consisting of alkyl and cycloalkyl.

In another embodiment, in formula (II), $R^3$ and $R^4$ together with the carbon atoms to which they are attached form a furanyl group which is unsubstituted or substituted with a substituent selected from the group consisting of alkyl, alkoxyalkyl, benzyl, and cycloalkyl.

In another embodiment, in formula (II), $R^3$ and $R^4$ together with the carbon atoms to which they are attached form a furanyl group which is unsubstituted or substituted with a substituent selected from the group consisting of alkyl and cycloalkyl, wherein said alkyl substituent is unsubstituted or substituted with an alkoxy or an aryl group.

In another embodiment, in formula (II), $R^3$ and $R^4$ together with the carbon atoms to which they are attached form a furanyl group which is unsubstituted or substituted with a substituent selected from the group consisting of alkyl and cycloalkyl, wherein said alkyl substituent is selected from the group consisting of methyl, methoxymethyl, and benzyl.

In another embodiment, in formula (II), $R^3$ and $R^4$ together with the carbon atoms to which they are attached form a furanyl group which is unsubstituted or substituted with a substituent selected from the group consisting of alkyl and cycloalkyl, wherein said cycloalkyl is cyclopropyl.

In another embodiment, in formula (II), m is 0.

In another embodiment, in formula (II), m is 1.

In another embodiment, in formula (II), $R^5$ is heteroaryl.

In another embodiment, in formula (II), $R^5$ is pyrazolyl.

In another embodiment, the compound of formula (II) is elected from the group consisting of:

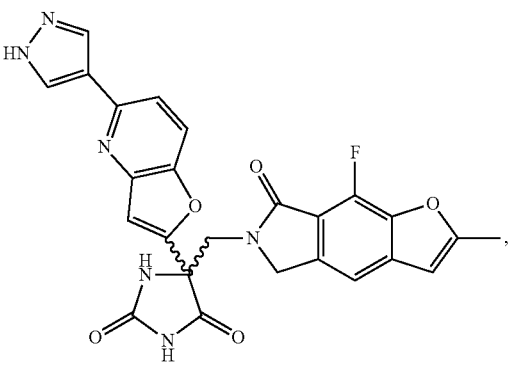

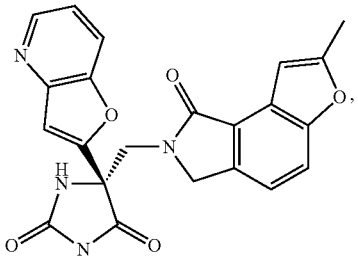

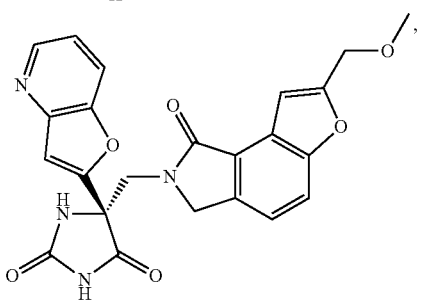

-continued

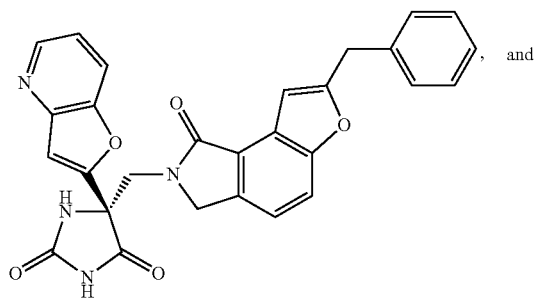

, and

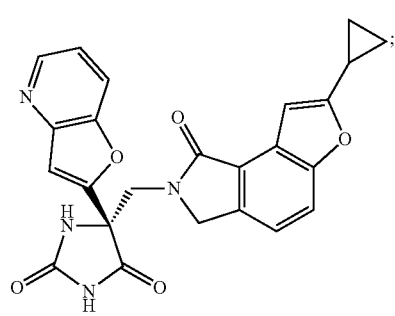

;

or a pharmaceutically acceptable salt or solvate thereof.

In another embodiment, in formula (III), ring B is aryl or heteroaryl.

In another embodiment, in formula (III), ring B is aryl or heteroaryl substituted with an alkoxy.

In another embodiment, in formula (III), ring B is aryl.

In another embodiment, in formula (III), ring B is phenyl.

In another embodiment, in formula (III), said ring B phenyl is substituted with an alkoxy.

In another embodiment, in formula (III), said ring B phenyl is substituted with an alkoxy, wherein said alkoxy is methoxy.

In another embodiment, in formula (III), T alkynyl is —C≡C—.

In another embodiment, in formula (III), V heteroaryl is pyridyl.

In another embodiment, in formula (III), R is H.

In another embodiment, in formula (III), $R^1$ is H.

In another embodiment, the compound of formula (III) is selected from the group consisting of:

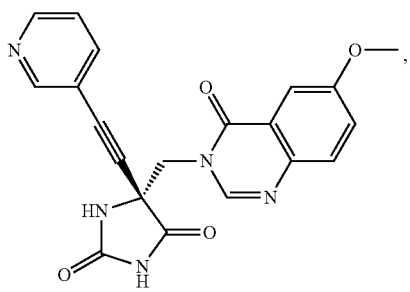

-continued

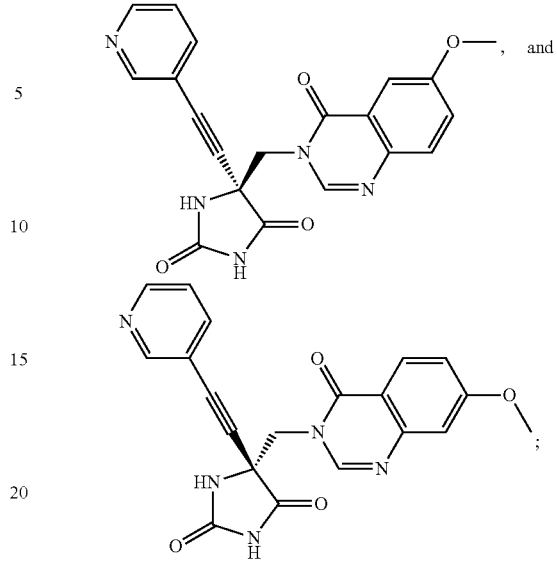

or a pharmaceutically acceptable salt or solvate thereof.

In another embodiment, in formula (IV), ring A is aryl.

In another embodiment, in formula (IV), T is selected from the group consisting of alkynyl and heteroaryl.

In another embodiment, in formula (IV), V is aryl or heteroaryl.

In another embodiment, the compound of formula (IV) is represented by formula (IVA):

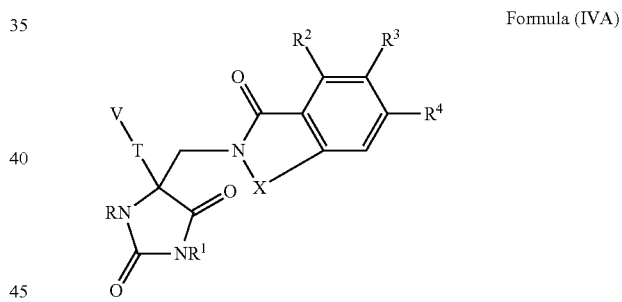

Formula (IVA)

or a pharmaceutically acceptable salt or solvate thereof, wherein T, V, X, R, $R^1$, $R^2$, $R^3$, and $R^4$ are as defined in Formula (IV).

In another embodiment, in formula (IV):
T is selected from the group consisting of alkynyl and heteroaryl; and
V is absent or present, and if present, is selected from the group consisting of aryl and heterocyclyl.

In another embodiment, in formula (IV), said T alkynyl is —C≡C—.

In another embodiment, in formula (IV), said T heteroaryl is

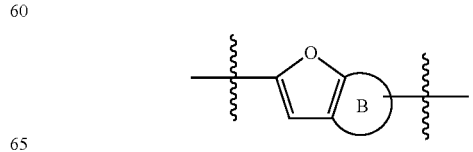

wherein ring B is pyridine.

In another embodiment, in formula (IV), said V heterocyclyl is selected from the group consisting of piperidinyl, and

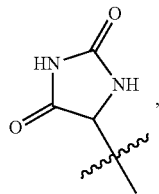 [SMILES: *C1NC(=O)NC1=O]

each of which independently is unsubstituted or substituted with one or two substituents independently selected from the group consisting of —NH$_2$, —NH(alkyl), —N(alkyl)$_2$, and aminoalkyl.

In another embodiment, in formula (IV), said V aryl is phenyl which is unsubstituted or substituted with one to two substitutents selected from the group consisting of —C(=O)NH$_2$, —C(=O)NH(alkyl), and —C(=O)N(alkyl)$_2$.

In another embodiment, in formula (IV), R is H.

In another embodiment, in formula (IV), R$^1$ is H.

In another embodiment, in formula (IV), R$^2$ is halo.

In another embodiment, in formula (IV), R$^2$ is fluoro or chloro.

In another embodiment, in formula (IV), R$^3$ is alkoxy.

In another embodiment, in formula (IV), R$^3$ is methoxy.

In another embodiment, in formula (IV), R$^4$ is halo.

In another embodiment, in formula (IV), R$^4$ is fluoro or chloro.

In another embodiment, in formula (IV), X is —(CR$^5{}_2$)$_p$—.

In another embodiment, in formula (IV), X is —(CR$^5{}_2$)$_p$—, wherein R$^5$ is H.

In another embodiment, in formula (IV), X is —(CR$^5{}_2$)$_p$—, wherein p is 1.

In another embodiment, the compound of formula (IV) is selected from the group consisting of:

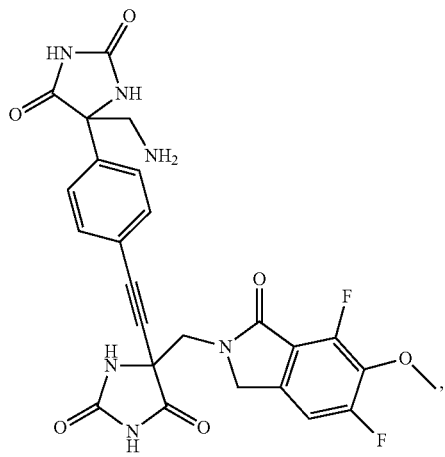

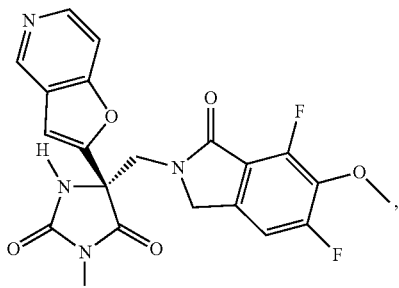

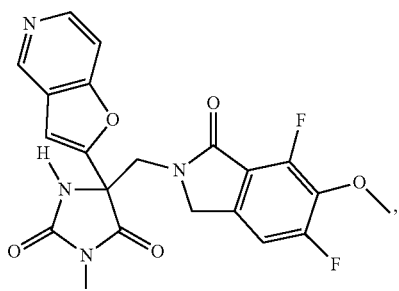

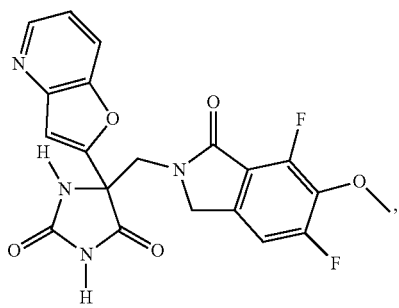

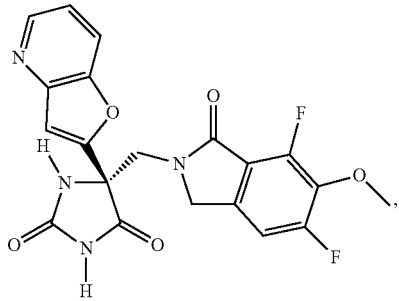

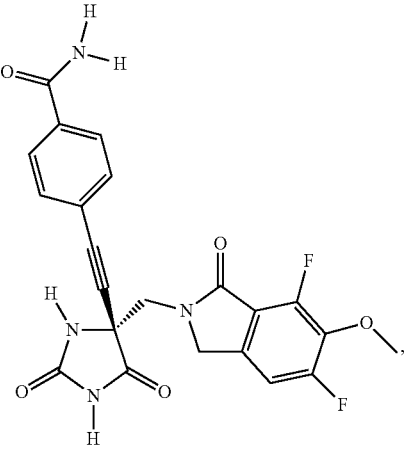

-continued

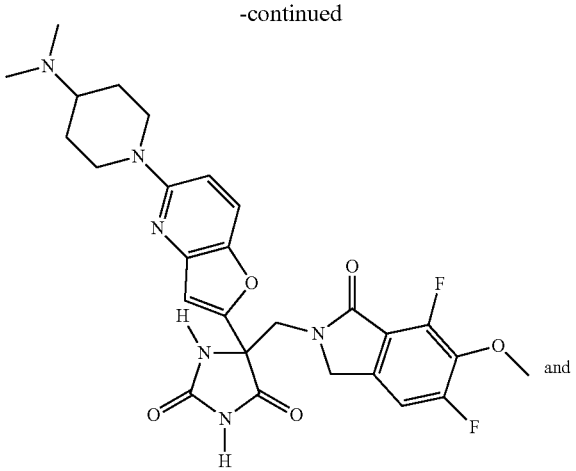

and

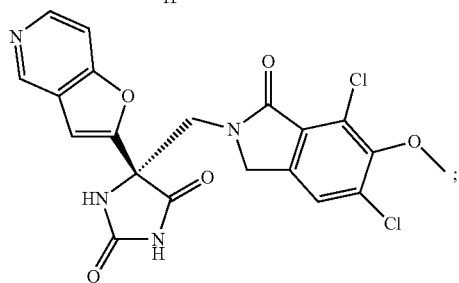

or a pharmaceutically acceptable salt or solvate thereof.

In another embodiment, in formula (V), at least one of T and V is substituted with an R² substituent; and at least one of T and V is present, and at least one of T and V is substituted with an R² substituent.

In another embodiment, in formula (V):
ring A is aryl;
only one of T and V is present and is heteroaryl which is substituted with an R².

In another embodiment, in formula (V):
ring A is aryl;
both T and V are present;
T is —C≡C—; and
V is selected from the group consisting of aryl and heteroaryl, each of which is substituted with R².

In another embodiment, in formula (V), at least one of T and V is substituted with an R² substituent.

In another embodiment, in formula (V), ring A is aryl or heteroaryl.

In another embodiment, in formula (V), ring A is aryl or heteroaryl substituted with an alkoxy.

In another embodiment, in formula (V), ring A is phenyl substituted with an alkoxy.

In another embodiment, in formula (V), ring A is phenyl substituted with a methoxy.

In another embodiment, in formula (V), said V aryl is phenyl.

In another embodiment, in formula (V), said V heteroaryl is thiophenyl.

In another embodiment, in formula (V), X is —(CR⁷₂)ₚ—.

In another embodiment, in formula (V), X is —(CR⁷₂)ₚ—, wherein R⁷ is H.

In another embodiment, in formula (V), X is —(CR⁷₂)ₚ—, wherein p is 1.

In another embodiment, in formula (V), wherein R' is H.

In another embodiment, in formula (V), wherein R is H.

In another embodiment, in formula (V), wherein R¹ is H.

In another embodiment, in formula (V), R³ is selected from the group consisting of: —C(=N—OH)—N(alkyl)₂, —C(=O)NHS(=O)₂NH₂, —C(H)((C=O)OH)-heterocyclyl-C(=O)Oalkyl, —C(H)((C=O)(H₂)-heterocyclyl-C(=O)Oalkyl, —NH—C(=S)N(H)-alkyl-heterocyclyl, —C(=NH)NHOH, —C(=NH)-heterocyclyl-alkyl, and —C(=NH)—NH₂.

In another embodiment, the compound of formula (V) is selected from the group consisting of:

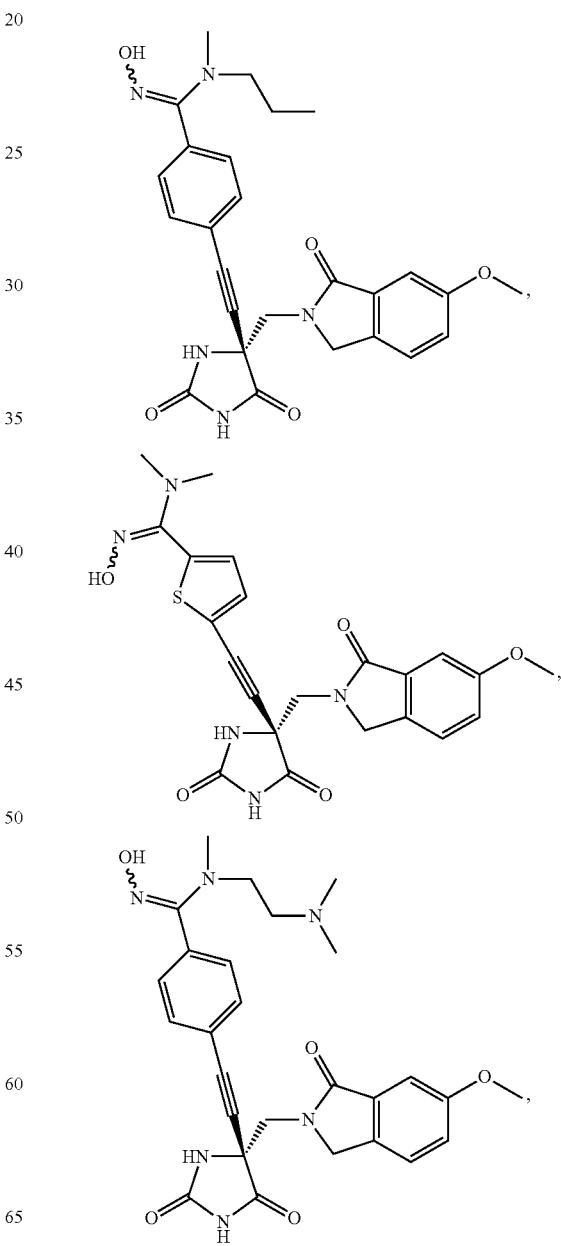

23
-continued
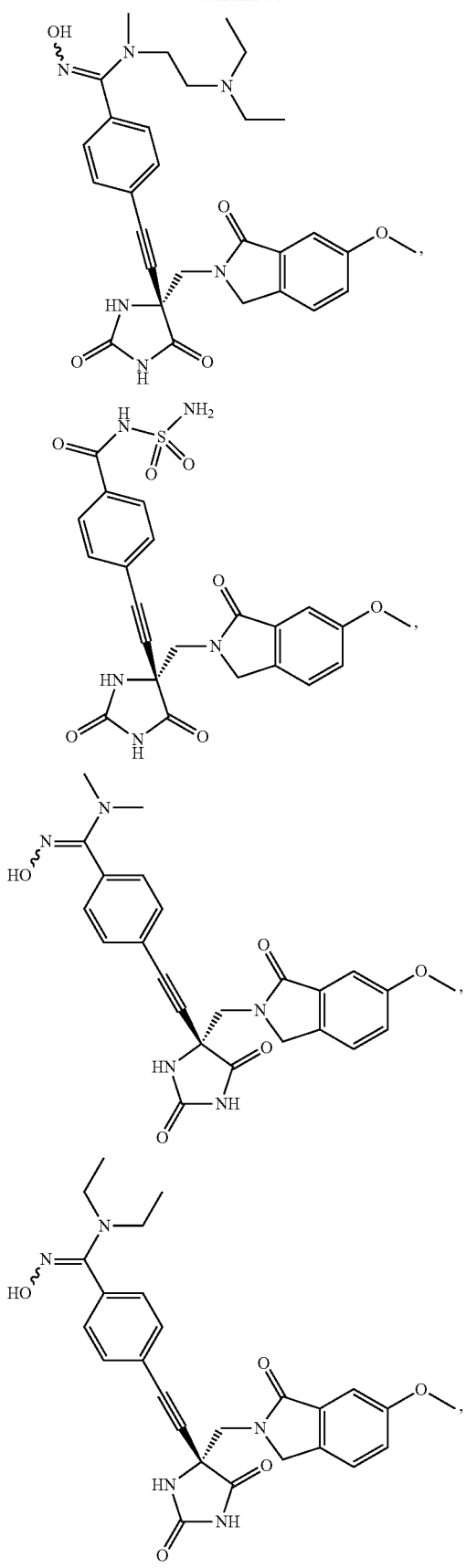
24
-continued
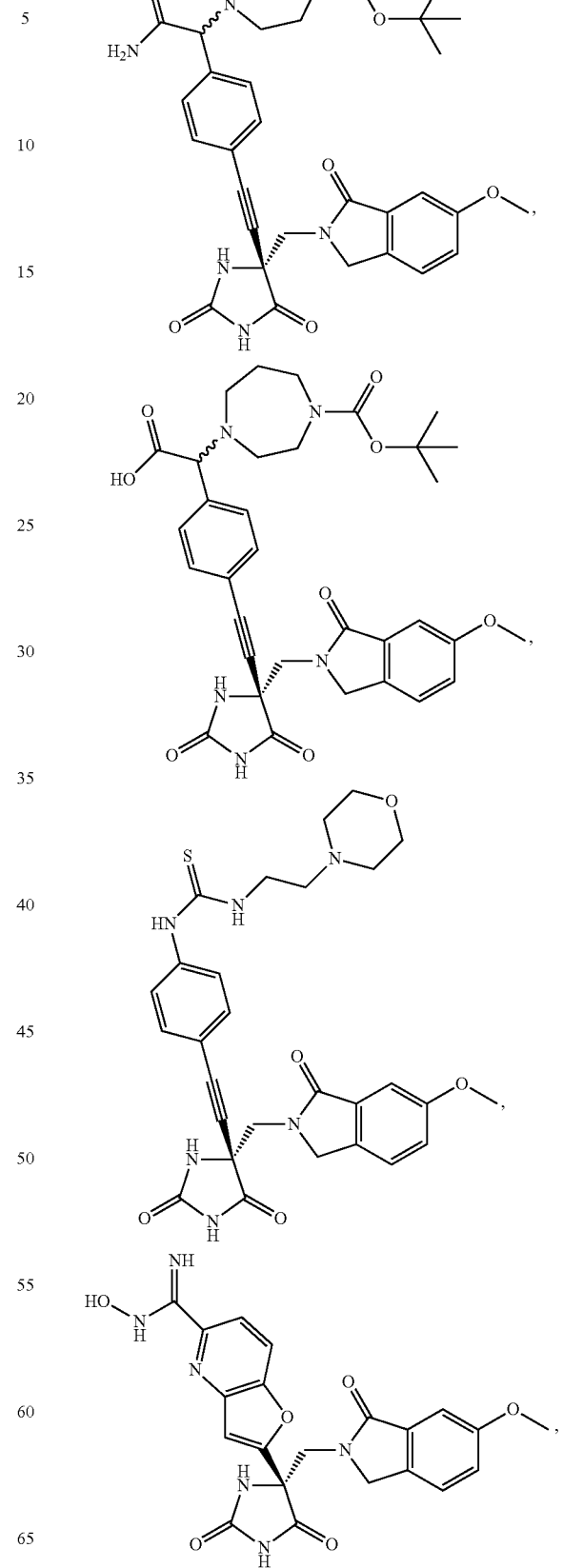

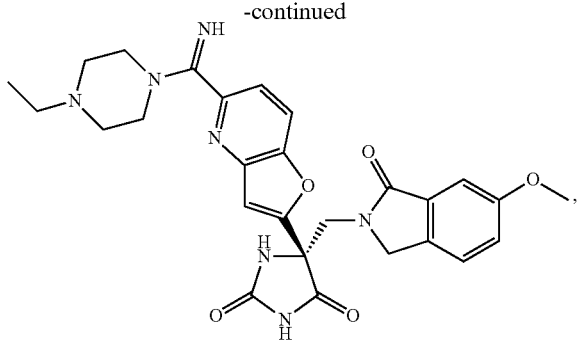

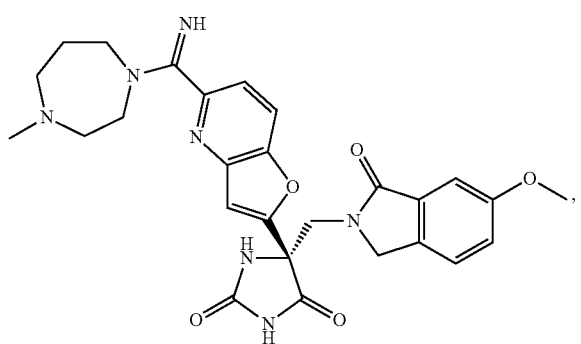

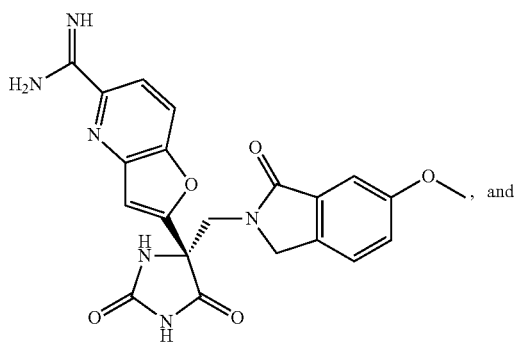

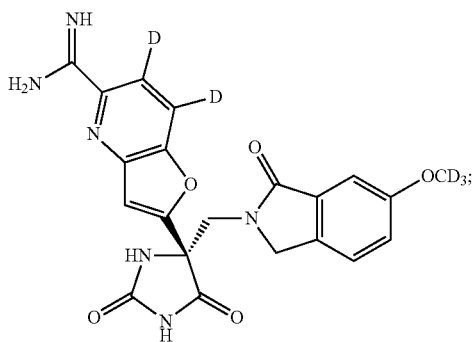

or a pharmaceutically acceptable salt or solvate thereof.

In another embodiment, in formula (VI), X is —(CR$^7_2$)$_p$—.

In another embodiment, in formula (VI), X is —(CR$^7_2$)$_p$—, wherein R$^7$ is H.

In another embodiment, in formula (VI), X is —(CR$^7_2$)$_p$—, wherein p is 1.

In another embodiment, in formula (VI), R' is H.

In another embodiment, in formula (VI), R is H.

In another embodiment, in formula (VI), R$^1$ is H.

In another embodiment, in formula (VI), ring A is aryl or heteroaryl.

In another embodiment, in formula (VI), ring A is aryl or heteroaryl, which is substituted with one or two substituents selected from the group consisting of halo and alkoxy.

In another embodiment, in formula (VI), ring A is aryl.

In another embodiment, in formula (VI), ring A is phenyl.

In another embodiment, in formula (VI), ring A is phenyl, which is substituted with one or two substituents selected from the group consisting of halo and alkoxy.

In another embodiment, in formula (VI), ring A is phenyl, which is substituted with one or two substituents selected from the group consisting of fluoro and methoxy.

In another embodiment, in formula (VI), Y is O.

In another embodiment, in formula (VI), T is heteroaryl wherein said heteroaryl is pyridyl.

In another embodiment, in formula (VI). T is pyridyl which is substituted with a hydroxy substituent.

In another embodiment, in formula (VI), —NR$^4$R$^5$ is selected from the group consisting of —NH(heteroaryl), —NH(heterocyclyl) and heterocyclyl.

In another embodiment, the compound of formula (VI) is selected from the group consisting of:

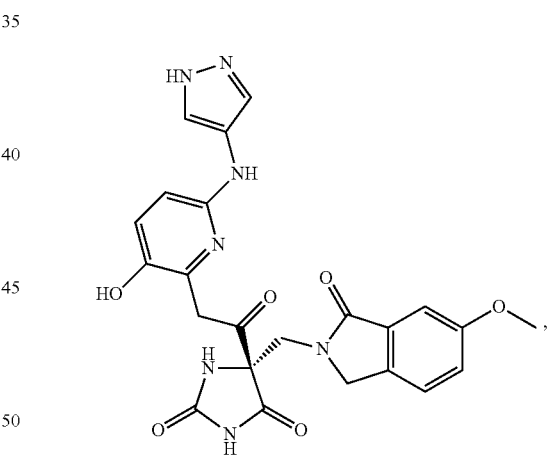

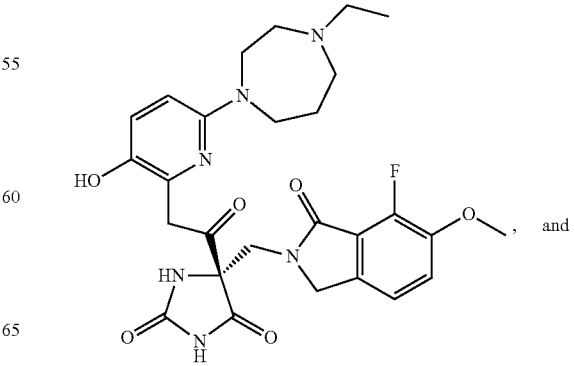

-continued

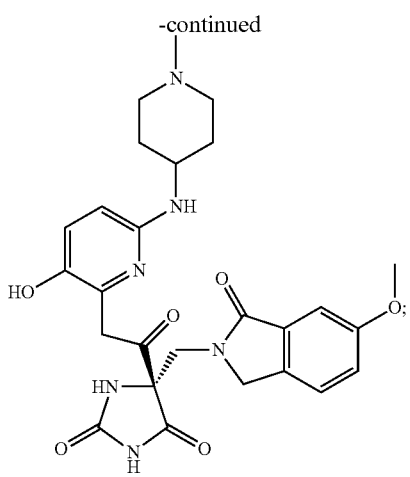

or a pharmaceutically acceptable salt or solvate thereof.

In another embodiment, in formula (VII), ring A is aryl which is unsubstituted or is substituted with an alkoxy.

In another embodiment, in formula (VII), ring A is aryl which is substituted with an alkoxy.

In another embodiment, in formula (VII), ring A is aryl.

In another embodiment, in formula (VII), ring A is phenyl.

In another embodiment, in formula (VII), ring A is phenyl, which is unsubstituted or substituted with an alkoxy.

In another embodiment, in formula (VII), ring A is phenyl, which is unsubstituted or substituted with a methoxy.

In another embodiment, in formula (VII), said T heteroaryl, optionally with said five- to eight membered heterocyclyl ring is selected from the group consisting of:

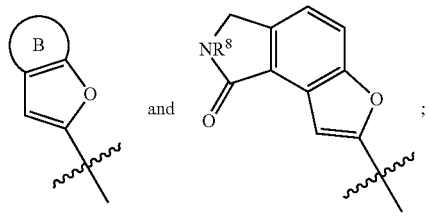

wherein ring B is pyridyl and $R^8$ is H or alkyl.

In another embodiment, in formula (VII), when said T heteroaryl, optionally with said five- to eight membered heterocyclyl ring is

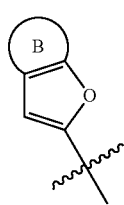

ring B pyridyl is unsubstituted or substituted with a heteroaryl.

In another embodiment, in formula (VII), when said T heteroaryl, optionally with said five- to eight membered heterocyclyl ring is

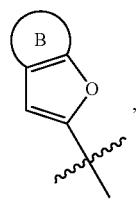

ring B pyridyl is substituted with a pyrazolyl.

In another embodiment, in formula (VII), R is H.

In another embodiment, in formula (VII), $R^1$ is H.

In another embodiment, in formula (VII), $R^2$, $R^3$, $R^4$, and $R^5$ are all H.

In another embodiment, the compound of formula (VII) is selected from the group consisting of:

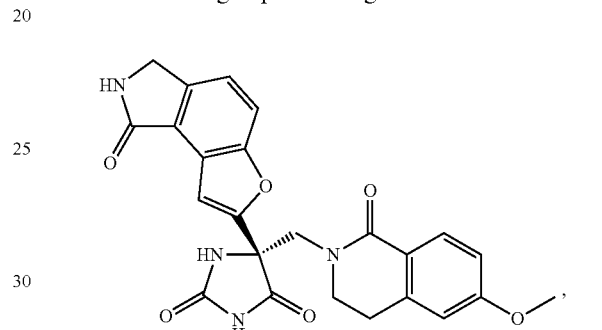

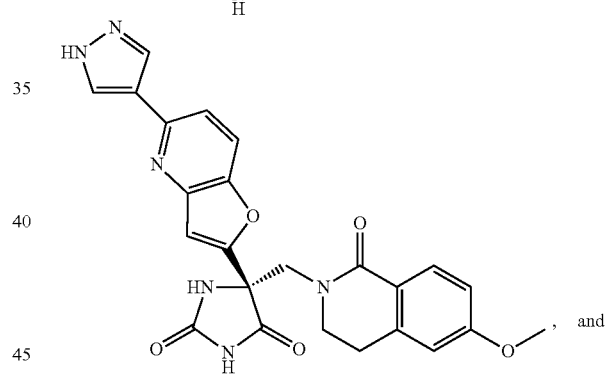

, and

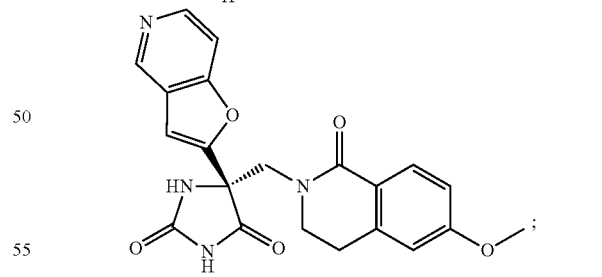

;

or a pharmaceutically acceptable salt or solvate thereof.

In another embodiment, in formula (VIII), X is —(CR$^7_2$)$_p$—.

In another embodiment, in formula (VIII), X is —(CR$^7_2$)$_p$—, wherein R$^7$ is H.

In another embodiment, in formula (VIII), X is —(CR$^7_2$)$_p$—, wherein p is 1.

In another embodiment, in formula (VIII), T is heteroaryl.

In another embodiment, in formula (VIII), T is

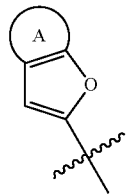

wherein ring A is pyridyl.

In another embodiment, in formula (VIII), T is

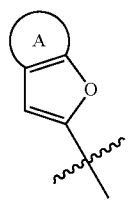

wherein ring A is pyridyl, wherein said pyridyl is substituted with a halo.

In another embodiment, in formula (VIII), Y is selected from the group consisting of —NH$_2$, —OH, and —NHC(=O)NH$_2$.

In another embodiment, in formula (VIII), R$^2$ is alkyl.

In another embodiment, in formula (VIII), R$^2$ is methyl.

In another embodiment, in formula (VIII), R$^3$ is selected from the group consisting of H and fluoro.

In another embodiment, the compound of formula (VIII) is selected from the group consisting of:

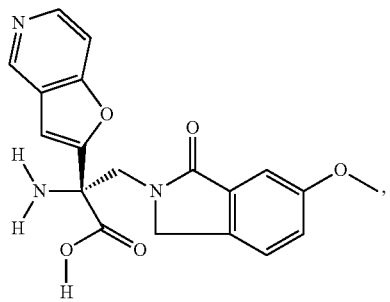

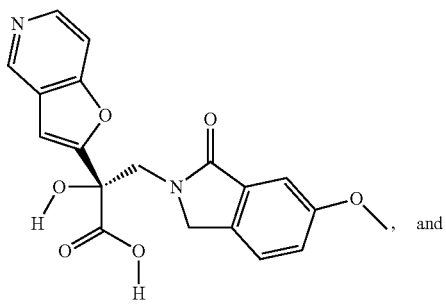, and

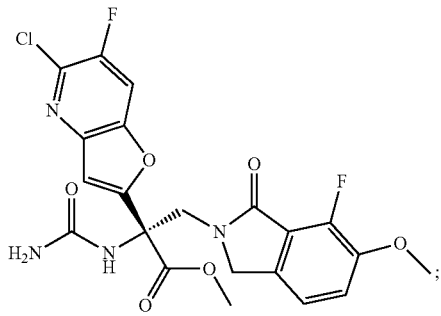

or a pharmaceutically acceptable salt or solvate thereof.

In another embodiment, the present invention provides a compound selected from the group consisting of:

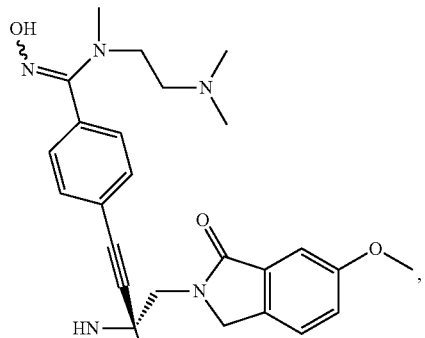

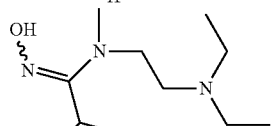

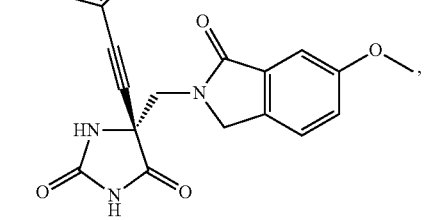

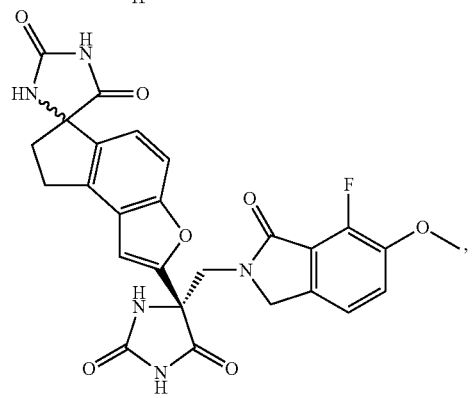

31
-continued
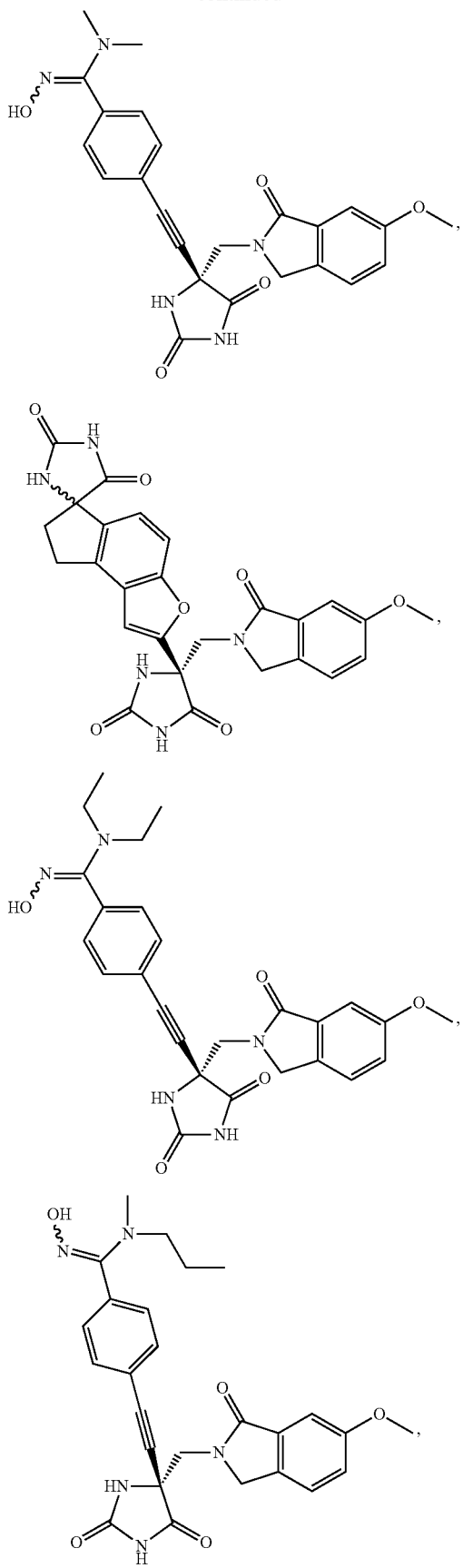
32
-continued
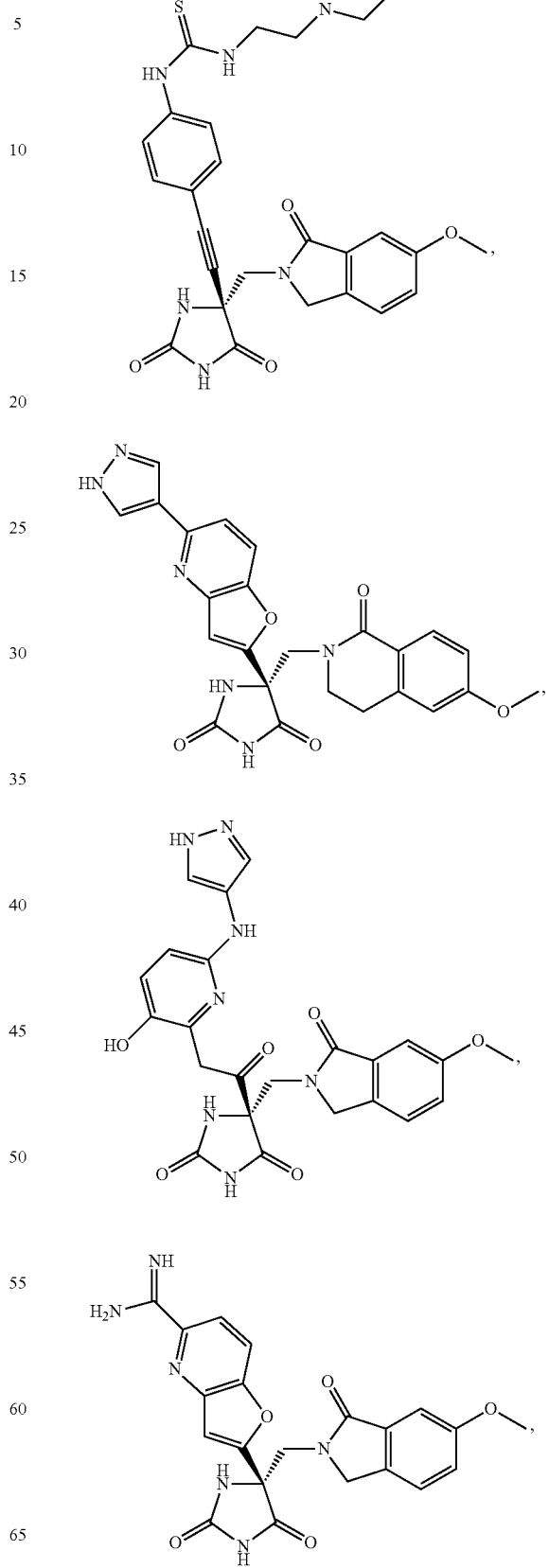

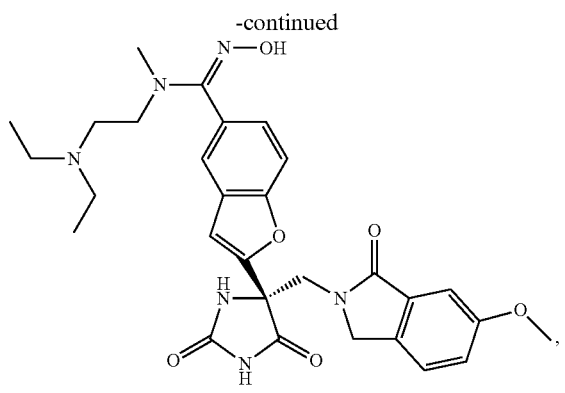

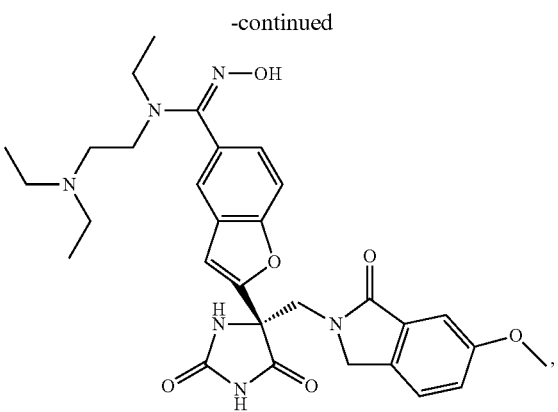

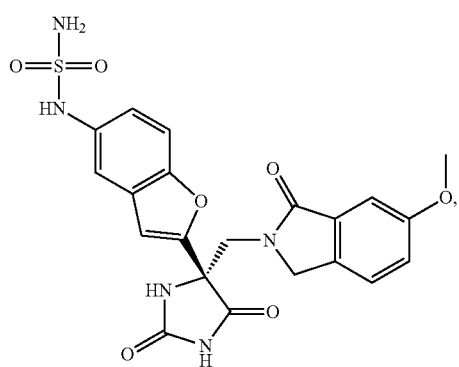

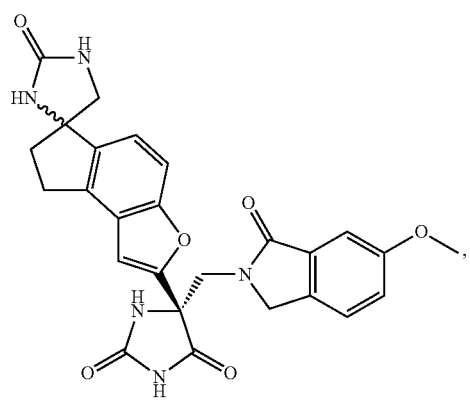

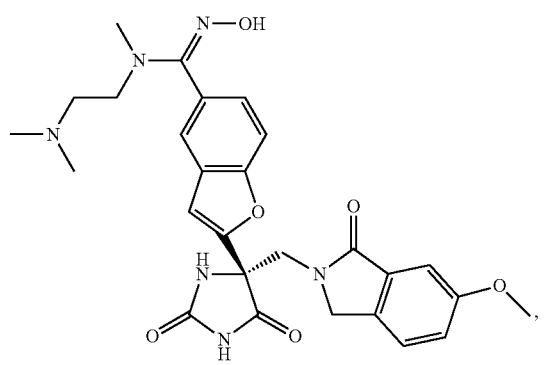

or a pharmaceutically acceptable salt or solvate thereof.

As used above, and throughout this disclosure, the following terms, unless otherwise indicated, shall be understood to have the following meanings:

"Patient" includes both human and animals.

"Mammal" means humans and other mammalian animals.

"Alkyl" means an aliphatic hydrocarbon group which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. "Lower alkyl" means a group having about 1 to about 6 carbon atoms in the chain which may be straight or branched. The alkyl group may be substituted by one or more substituents which may be the same or different, each substituent being independently selected from the group consisting of halo, alkyl, aryl, heteroaryl, cycloalkyl, cyano, hydroxy, alkoxy, alkylthio, amino, oxime (e.g., =N—OH), —NH(alkyl), —NH(cycloalkyl), —N(alkyl)$_2$, —O—C(O)-alkyl, —O—C(O)-aryl, —O—C(O)-cycloalkyl, carboxy and —C(O)O-alkyl. Non-limiting examples of suitable alkyl groups include methyl, ethyl, n-propyl, isopropyl and t-butyl.

"Alkenyl" means an aliphatic hydrocarbon group containing at least one carbon-carbon double bond and which may be straight or branched and comprising about 2 to about 15 carbon atoms in the chain. Preferred alkenyl groups have about 2 to about 12 carbon atoms in the chain; and more preferably about 2 to about 6 carbon atoms in the chain. Branched means that one or more lower alkyl groups such as methyl, ethyl or propyl, are attached to a linear alkenyl chain. "Lower alkenyl" means about 2 to about 6 carbon atoms in the chain which may be straight or branched. "Alkenyl" may be unsubstituted or optionally substituted by one or more substituents which may be the same or different, each substituent being independently selected from the group consisting of halo, alkyl, aryl, heteroaryl, cycloalkyl, cyano, alkoxy and —S(alkyl). Non-limiting examples of suitable alkenyl groups include ethenyl, propenyl, n-butenyl, 3-methylbut-2-enyl, n-pentenyl, octenyl and decenyl.

"Alkylene" means a difunctional group obtained by removal of a hydrogen atom from an alkyl group that is defined above. Non-limiting examples of alkylene include methylene, ethylene and propylene.

"Alkynyl" means an aliphatic hydrocarbon group containing at least one carbon-carbon triple bond and which may be straight or branched and comprising about 2 to about 15 carbon atoms in the chain. Preferred alkynyl groups have about 2 to about 12 carbon atoms in the chain; and more preferably about 2 to about 4 carbon atoms in the chain. Branched means that one or more lower alkyl groups such as methyl, ethyl or propyl, are attached to a linear alkynyl chain. "Lower alkynyl" means about 2 to about 6 carbon atoms in the chain which may be straight or branched. Non-limiting examples of suitable alkynyl groups include ethynyl, propynyl, 2-butyryl and 3-methylbutynyl. "Alkynyl" may be unsubstituted or optionally substituted by one or more substituents which may be the same or different, each substituent being independently selected from the group consisting of alkyl, aryl and cycloalkyl.

"Aryl" means an aromatic monocyclic or multicyclic ring system comprising about 6 to about 14 carbon atoms, preferably about 6 to about 10 carbon atoms. The aryl group can be optionally substituted with one or more "ring system substituents" which may be the same or different, and are as defined herein. Non-limiting examples of suitable aryl groups include phenyl and naphthyl.

"Heteroaryl" means an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination. Preferred heteroaryls contain about 5 to about 6 ring atoms. The "heteroaryl" can be optionally substituted by one or more "ring system substituents" which may be the same or different, and are as defined herein. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide. "Heteroaryl" may also include a heteroaryl as defined above fused to an aryl as defined above. Non-limiting examples of suitable heteroaryls include pyridyl, pyrazinyl, furanyl, thienyl, pyrimidinyl, pyridone (including N-substituted pyridones), isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like. The term "heteroaryl" also refers to partially saturated heteroaryl moieties such as, for example, tetrahydroisoquinolyl, tetrahydroquinolyl and the like.

"Aralkyl" or "arylalkyl" means an aryl-alkyl- group in which the aryl and alkyl are as previously described. Preferred aralkyls comprise a lower alkyl group. Non-limiting examples of suitable aralkyl groups include benzyl, 2-phenethyl and naphthalenylmethyl. The bond to the parent moiety is through the alkyl.

"Alkylaryl" means an alkyl-aryl- group in which the alkyl and aryl are as previously described. Preferred alkylaryls comprise a lower alkyl group. Non-limiting example of a suitable alkylaryl group is tolyl. The bond to the parent moiety is through the aryl.

"Cycloalkyl" means a non-aromatic mono- or multicyclic ring system comprising about 3 to about 10 carbon atoms, preferably about 5 to about 10 carbon atoms. Preferred cycloalkyl rings contain about 5 to about 7 ring atoms. The cycloalkyl can be optionally substituted with one or more "ring system substituents" which may be the same or different, and are as defined above. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalinyl, norbornyl, adamantyl and the like.

"Cycloalkylalkyl" means a cycloalkyl moiety as defined above linked via an alkyl moiety (defined above) to a parent core. Non-limiting examples of suitable cycloalkylalkyls include cyclohexylmethyl, adamantylmethyl and the like.

"Cycloalkenyl" means a non-aromatic mono or multicyclic ring system comprising about 3 to about 10 carbon atoms, preferably about 5 to about 10 carbon atoms which contains at least one carbon-carbon double bond. Preferred cycloalkenyl rings contain about 5 to about 7 ring atoms. The cycloalkenyl can be optionally substituted with one or more "ring system substituents" which may be the same or different, and are as defined above. Non-limiting examples of suitable monocyclic cycloalkenyls include cyclopentenyl, cyclohexenyl, cyclohepta-1,3-dienyl, and the like. Non-limiting example of a suitable multicyclic cycloalkenyl is norbornylenyl.

"Cycloalkenylalkyl" means a cycloalkenyl moiety as defined above linked via an alkyl moiety (defined above) to a parent core. Non-limiting examples of suitable cycloalkenylalkyls include cyclopentenylmethyl, cyclohexenylmethyl and the like.

"Halo" or "Halogen" means fluorine, chlorine, bromine, or iodine. Preferred are fluorine, chlorine and bromine.

"Ring system substituent" means a substituent attached to an aromatic or non-aromatic ring system which, for example, replaces an available hydrogen on the ring system. Ring system substituents may be the same or different, each being independently selected from the group consisting of alkyl, alkenyl, alkynyl, aryl, heteroaryl, aralkyl, alkylaryl, heteroaralkyl, heteroarylalkenyi, heteroarylalkynyl, alkylheteroaryl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylthio, arylthio, heteroarylthio, aralkylthio, heteroaralkylthio, cycloalkyl, heterocyclyl, —O—C(O)-alkyl, —O—C(O)-aryl, —O—C(O)-cycloalkyl, —C(=N—CN)—NH$_2$, —C(=NH)—NH$_2$, —C(=NH)—NH(alkyl), oxime (e.g., =N—OH), —NY$_1$Y$_2$, -alkyl-NY$_1$Y$_2$, —C(O)NY$_1$Y$_2$, —SO$_2$NY$_1$Y$_2$ and —SO$_2$NY$_1$Y$_2$, wherein $Y_1$ and $Y_2$ can be the same or different and are independently selected from the group consisting of hydrogen, alkyl, aryl, cycloalkyl, and aralkyl. "Ring system substituent" may also mean a single moiety which simultaneously replaces two available hydrogens on two adjacent carbon atoms (one H on each carbon) on a ring system. Examples of such moiety are methylene dioxy, ethylenedioxy, —C(CH$_3$)$_2$— and the like which form moieties such as, for example:

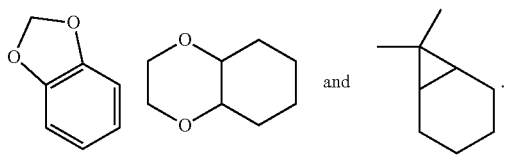

"Heteroarylalkyl" means a heteroaryl moiety as defined above linked via an alkyl moiety (defined above) to a parent core. Non-limiting examples of suitable heteroaryls include 2-pyridinylmethyl, quinolinylmethyl and the like. "Heterocyclyl" means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocyclyls contain about 5 to about 6 ring atoms. The prefix aza, oxa or thia before the heterocyclyl root name means that at least a nitrogen, oxygen or sulfur atom respectively is present as a ring atom. Any —NH in a heterocyclyl ring may exist protected such as, for example, as an —N(Boc), —N(CBz), —N(Tos) group and the like; such protections are also considered part of this invention. The heterocyclyl can be optionally substituted by one or more "ring system substituents" which may be the same or different, and are as defined herein. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, morpholinyl, thiomorpholinyl, thiazolidinyl, 1,4-dioxanyl, tetrahydrofuranyl, tetrahydrothiophenyl, lactam, lactone, and the like. "Heterocyclyl" also includes heterocyclyl rings as described above wherein =O replaces two available hydrogens on the same ring carbon atom. Example of such moiety is pyrrolidone:

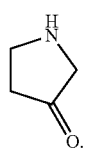

"Heterocyclylalkyl" means a heterocyclyl moiety as defined above linked via an alkyl moiety (defined above) to a parent core. Non-limiting examples of suitable heterocyclylalkyls include piperidinylmethyl, piperazinylmethyl and the like.

"Heterocyclenyl" means a non-aromatic monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur atom, alone or in combination, and which contains at least one carbon-carbon double bond or carbon-nitrogen double bond. There are no adjacent oxygen and/or sulfur atoms present in the ring system. Preferred heterocyclenyl rings contain about 5 to about 6 ring atoms. The prefix aza, oxa or thia before the heterocyclenyl root name means that at least a nitrogen, oxygen or sulfur atom respectively is present as a ring atom. The heterocyclenyl can be optionally substituted by one or more ring system substituents, wherein "ring system substituent" is as defined above. The nitrogen or sulfur atom of the heterocyclenyl can be optionally oxidized to the corresponding N-oxide, S-oxide or S,S-dioxide. Non-limiting examples of suitable heterocyclenyl groups include 1,2,3,4-tetrahydropyridinyl, 1,2-dihydropyridinyl, 1,4-dihydropyridinyl, 1,2,3,6-tetrahydropyridinyl, 1,4,5,6-tetrahydropyrimidinyl, 2-pyrrolinyl, 3-pyrrolinyl, 2-imidazolinyl, 2-pyrazolinyl, dihydroimidazolyl, dihydrooxazolyl, dihydrooxadiazolyl, dihydrothiazolyl, 3,4-dihydro-2H-pyranyl, dihydrofuranyl, fluorodihydrofuranyl, 7-oxabicyclo[2.2.1]heptenyl, dihydrothiophenyl, dihydrothiopyranyl, and the like. "Heterocyclenyl" also includes heterocyclenyl rings as described above wherein =O replaces two available hydrogens on the same ring carbon atom. Example of such moiety is pyrrolidinone:

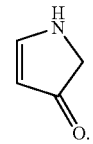

"Heterocyclenylalkyl" means a heterocyclenyl moiety as defined above linked via an alkyl moiety (defined above) to a parent core.

It should be noted that in hetero-atom containing ring systems of this invention, there are no hydroxyl groups on carbon atoms adjacent to a N, O or S, as well as there are no N or S groups on carbon adjacent to another heteroatom. Thus, for example, in the ring:

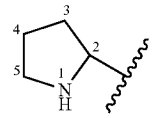

there is no —OH attached directly to carbons marked 2 and 5.

It should also be noted that tautomeric forms such as, for example, the moieties:

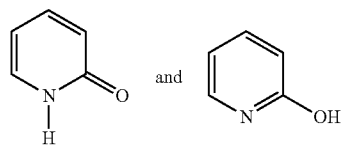 [SMILES: O=c1cccc[nH]1 ; Oc1ccccn1]

are considered equivalent in certain embodiments of this invention.

"Alkynylalkyl" means an alkynyl-alkyl- group in which the alkynyl and alkyl are as previously described. Preferred alkynylalkyls contain a lower alkynyl and a lower alkyl group. The bond to the parent moiety is through the alkyl. Non-limiting examples of suitable alkynylalkyl groups include propargylmethyl.

"Heteroaralkyl" means a heteroaryl-alkyl- group in which the heteroaryl and alkyl are as previously described. Preferred heteroaralkyls contain a lower alkyl group. Non-limiting examples of suitable aralkyl groups include pyridylmethyl, and quinolin-3-ylmethyl. The bond to the parent moiety is through the alkyl.

"Hydroxyalkyl" means a HO-alkyl- group in which alkyl is as previously defined. Preferred hydroxyalkyls contain lower alkyl. Non-limiting examples of suitable hydroxyalkyl groups include hydroxymethyl and 2-hydroxyethyl.

"Acyl" means an H—C(O)—, alkyl-C(O)— or cycloalkyl-C(O)—, group in which the various groups are as previously described. The bond to the parent moiety is through the carbonyl. Preferred acyls contain a lower alkyl. Non-limiting examples of suitable acyl groups include formyl, acetyl and propanoyl.

"Aroyl" means an aryl-C(O)— group in which the aryl group is as previously described. The bond to the parent moiety is through the carbonyl. Non-limiting examples of suitable groups include benzoyl and 1-naphthoyl.

"Alkoxy" means an alkyl-O— group in which the alkyl group is as previously described. Non-limiting examples of suitable alkoxy groups include methoxy, ethoxy, n-propoxy, isopropoxy and n-butoxy. The bond to the parent moiety is through the ether oxygen.

"Aryloxy" means an aryl-O— group in which the aryl group is as previously described. Non-limiting examples of suitable aryloxy groups include phenoxy and naphthoxy. The bond to the parent moiety is through the ether oxygen.

"Aralkyloxy" means an aralkyl-O— group in which the aralkyl group is as previously described. Non-limiting examples of suitable aralkyloxy groups include benzyloxy and 1- or 2-naphthalenemethoxy. The bond to the parent moiety is through the ether oxygen.

"Alkylthio" means an alkyl-S— group in which the alkyl group is as previously described. Non-limiting examples of suitable alkylthio groups include methylthio and ethylthio. The bond to the parent moiety is through the sulfur.

"Arylthio" means an aryl-S— group in which the aryl group is as previously described. Non-limiting examples of suitable arylthio groups include phenylthio and naphthylthio. The bond to the parent moiety is through the sulfur.

"Aralkylthio" means an aralkyl-S— group in which the aralkyl group is as previously described. Non-limiting example of a suitable aralkylthio group is benzylthio. The bond to the parent moiety is through the sulfur.

"Alkoxycarbonyl" means an alkyl-O—CO— group. Non-limiting examples of suitable alkoxycarbonyl groups include methoxycarbonyl and ethoxycarbanyl. The bond to the parent moiety is through the carbonyl.

"Aryloxycarbonyl" means an aryl-O—C(O)— group. Non-limiting examples of suitable aryloxycarbonyl groups include phenoxycarbonyl and naphthoxycarbonyl. The bond to the parent moiety is through the carbonyl.

"Aralkoxycarbonyl" means an aralkyl-O—C(O)— group. Non-limiting example of a suitable aralkoxycarbonyl group is benzyloxycarbonyl. The bond to the parent moiety is through the carbonyl.

"Alkylsulfonyl" means an alkyl-S($O_2$)— group. Preferred groups are those in which the alkyl group is lower alkyl. The bond to the parent moiety is through the sulfonyl.

"Arylsulfonyl" means an aryl-S($O_2$)— group. The bond to the parent moiety is through the sulfonyl.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound" or "stable structure" is meant a compound that is sufficiently robust to survive isolation to a useful degree of purity from a reaction mixture, and formulation into an efficacious therapeutic agent.

The term "optionally substituted" means optional substitution with the specified groups, radicals or moieties.

The term "purified", "in purified form" or "in isolated and purified form" for a compound refers to the physical state of said compound after being isolated from a synthetic process (e.g. from a reaction mixture), or natural source or combination thereof. Thus, the term "purified", "in purified form" or "in isolated and purified form" for a compound refers to the physical state of said compound after being obtained from a purification process or processes described herein or well known to the skilled artisan (e.g., chromatography, recrystallization and the like), in sufficient purity to be characterizable by standard analytical techniques described herein or well known to the skilled artisan.

It should also be noted that any carbon as well as heteroatom with unsatisfied valences in the text, schemes, examples and Tables herein is assumed to have the sufficient number of hydrogen atom(s) to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in organic Synthesis* (1991), Wiley, New York.

When any variable (e.g., aryl, heterocycle, $R^2$, etc.) occurs more than one time in any constituent or in Formulae (I)-(IX), its definition on each occurrence is independent of its definition at every other occurrence.

As used herein, the term "composition" is intended to encompass a product comprising the specified ingredients in the specified amounts, as well as any product which results, directly or indirectly, from combination of the specified ingredients in the specified amounts.

Prodrugs and solvates of the compounds of the invention are also contemplated herein. The term "prodrug", as employed herein, denotes a compound that is a drug precursor which, upon administration to a subject, undergoes chemical conversion by metabolic or chemical processes to yield a compound of Formulae (I)-(IX) or a salt and/or solvate thereof. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press, both of which are incorporated herein by reference thereto. The term "prodrug" means a compound (e.g, a drug precursor) that is transformed in vivo to yield a compound of Formulae (I)-(IX) or a pharmaceutically acceptable salt, hydrate or solvate of the compound. The transformation may occur by various mechanisms (e.g., by metabolic or chemical processes), such as, for example, through hydrolysis in blood. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

For example, if a compound of Formulae (I)-(IX) or a pharmaceutically acceptable salt, hydrate or solvate of the compound contains a carboxylic acid functional group, a prodrug can comprise an ester formed by the replacement of the hydrogen atom of the acid group with a group such as, for example, ($C_1$-$C_8$)alkyl, ($C_2$-$C_{12}$)alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—($C_1$-$C_2$)alkylamino($C_2$-$C_3$)alkyl (such as β-dimethylaminoethyl), carbamoyl-($C_1$-$C_2$)alkyl, N,N-di ($C_1$-$C_2$)alkylcarbamoyl-($C_1$-$C_2$)alkyl and piperidino-, pyrrolidino- or morpholino($C_2$-$C_3$) alkyl, and the like.

Similarly, if a compound of Formula (I)-(IX) contains an alcohol functional group, a prodrug can be formed by the replacement of the hydrogen atom of the alcohol group with a group such as, for example, ($C_1$-$C_6$)alkanoyloxymethyl, 1-(($C_1$-$C_6$)alkanoyloxy)ethyl, 1-methyl-1-(($C_1$-$C_6$)alkanoyloxy)ethyl, ($C_1$-$C_6$)alkoxycarbonyloxymethyl, N—($C_1$-$C_6$)alkoxycarbonylaminomethyl, succinoyl, ($C_1$-$C_6$)alkanoyl, α-amino($C_1$-$C_4$)alkanyl, arylacyl and α-aminoacyl, or α-aminoacyl-α-aminoacyl, where each α-aminoacyl group is independently selected from the naturally occurring L-amino acids. P(O)(OH)$_2$, —P(O)(O($C_1$-$C_6$)alkyl)$_2$ or glycosyl (the radical resulting from the removal of a hydroxyl group of the hemiacetal form of a carbohydrate), and the like.

If a compound of Formulae (I)-(IX) incorporates an amine functional group, a prodrug can be formed by the replacement of a hydrogen atom in the amine group with a group such as, for example, R-carbonyl, RO-carbonyl, NRR'-carbonyl where R and R' are each independently ($C_1$-$C_{10}$)alkyl, ($C_3$-$C_7$) cycloalkyl, benzyl, or R-carbonyl is a natural α-aminoacyl or natural α-aminoacyl, —C(OH)C(O)OY$^1$ wherein Y$^1$ is H, ($C_1$-$C_6$)alkyl or benzyl, —C(OY$^2$)Y$^3$ wherein Y$^2$ is ($C_1$-$C_4$)alkyl and Y$^3$ is ($C_1$-$C_6$)alkyl, carboxy ($C_1$-$C_6$)alkyl, amino ($C_1$-$C_4$)alkyl or mono-N— or di-N,N—($C_1$-$C_6$)alkylaminoalkyl, —C(Y$^4$)Y$^5$ wherein Y$^4$ is H or methyl and Y$^5$ is mono-N— or di-N,N—($C_1$-$C_6$)alkylamino morpholino, piperidin-1-yl or pyrrolidin-1-yl, and the like.

"Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

"Effective amount" or "therapeutically effective amount" is meant to describe an amount of compound or a composition of the present invention effective in inhibiting TACE, the production of TNF-α, MMPs, ADAMS or any combination thereof and thus producing the desired therapeutic, ameliorative, inhibitory or preventative effect.

The compounds of Formulae (I)-(IX) can form salts which are also within the scope of this invention. Reference to a compound of Formulae (I)-(IX) herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of Formulae (I)-(IX) contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the Formulae (I)-(IX) may be formed, for example, by reacting a compound of Formulae (I)-(IX) with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates,) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use*. (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quarternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Compounds of Formulae (I)-(IX), and salts, solvates and prodrugs thereof, may exist in their tautomeric form (for example, as an amide or imino ether). All such tautomeric forms are contemplated herein as part of the present invention.

All stereoisomers (for example, geometric isomers, optical isomers and the like) of the present compounds (including those of the salts, solvates and prodrugs of the compounds as well as the salts and solvates of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers (such as, for example, 4-pyridyl and 3-pyridyl). Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate" "prodrug" and the like, is intended to equally apply to the salt, solvate and prodrug of enantiomers, stereoisomers, rotamers, tautomers, positional isomers, racemates or prodrugs of the inventive compounds.

The present invention also embraces isotopically-labelled compounds of the present invention which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine and iodine, such as $^2H$, $^3H$, $^{11}C$, $^{13}C$, $^{14}C$, $^{15}N$, $^{18}O$, $^{17}O$, $^{31}P$, $^{32}P$, $^{35}S$, $^{18}F$, $^{36}Cl$ and $^{123}I$, respectively.

Certain isotopically-labelled compounds of Formulae (I)-(IX) (e.g., those labeled with $^3H$ and $^{14}C$) are useful in compound and/or substrate tissue distribution assays. Tritiated (i.e., $^3H$) and carbon-14 (i.e., $^{14}C$) isotopes are particularly preferred for their ease of preparation and detectability. Certain isotopically-labelled compounds of Formula (I) can be useful for medical imaging purposes such as those labeled with positron-emitting isotopes like $^{11}C$ or $^{18}F$ can be useful for application in Positron Emission Tomography (PET) and those labeled with gamma ray emitting isotopes like $^{123}I$ can be useful for application in Single photon emission computed tomography (SPECT). Further, substitution with heavier isotopes such as deuterium (i.e., $^2H$) may afford certain therapeutic advantages resulting from greater metabolic stability (e.g., increased in vivo half-life or reduced dosage requirements) and hence may be preferred in some circumstances. Additionally, isotopic substitution at a site where epimerization occurs may slow or reduce the epimerization process and thereby retain the more active or efficacious form of the compound for a longer period of time. Isotopically labeled compounds of Formula (I), in particular those containing isotopes with longer half lives (T1/2>1 day), can generally be prepared by following procedures analogous to those disclosed in the Schemes and/or in the Examples herein below, by substituting an appropriate isotopically labeled reagent for a non-isotopically labeled reagent.

Polymorphic forms of the compounds of Formulae (I)-(IX), and of the salts, solvates and prodrugs of the compounds of Formulae (I)-(IX) are intended to be included in the present invention.

The compounds according to the invention have pharmacological properties; in particular, the compounds of Formulae (I)-(IX) can be inhibitors of TACE, aggrecanase, TNF-α and/or MMP activity.

In one aspect, the invention provides a pharmaceutical composition comprising as an active ingredient at least one compound of Formulae (I)-(IX).

In another aspect, the invention provides a pharmaceutical composition comprising at least one compound of Formulae (I)-(IX) and additionally comprising at least one pharmaceutically acceptable carrier.

In another aspect, the invention provides a method of treating disorders associated with TACE, aggrecanase, TNF-α, MMPs, ADAMs or any combination thereof, said method comprising administering to a patient in need of such treatment an effective amount of at least one compound of Formulae (I)-(IX).

In another aspect, the invention provides a use of a compound of Formulae (I)-(IX) for the manufacture of a medicament to treat disorders associated with TACE, aggrecanase, TNF-α, MMPs, ADAMs or any combination thereof.

The compounds of Formulae (I)-(IX) can have anti-inflammatory activity and/or immunomodulatory activity and can be useful in the treatment of diseases including but not limited to septic shock, haemodynamic shock, sepsis syndrome, post ischaemic reperfusion injury, malaria, mycobacterial infection, meningitis, psoriasis, congestive heart failure, fibrotic diseases, cachexia, graft rejection, cancers such as cutaneous T-cell lymphoma, diseases involving angiogenesis, autoimmune diseases, skin inflammatory diseases, inflammatory bowel diseases such as Crohn's disease and colitis, OA and RA, ankylosing spondylitis, psoriatic arthritis, adult Still's disease, ureitis, Wegener's granulomatosis, Behcehe disease, Sjogren's syndrome, sarcoidosis, polymyositis, dermatomyositis, multiple sclerosis, sciatica, complex regional pain syndrome, radiation damage, hyperoxic alveolar injury, periodontal disease, HIV, non-insulin dependent diabetes mellitus, systemic lupus erythematosus, glaucoma, sarcoidosis, idiopathic pulmonary fibrosis, bronchopulmonary dysplasia, retinal disease, scleroderma, osteoporosis, renal ischemia, myocardial infarction, cerebral stroke, cerebral ischemia, nephritis, hepatitis, glomerulonephritis, cryptogenic fibrosing aveolitis, psoriasis, transplant rejection, atopic dermatitis, vasculitis, allergy, seasonal allergic rhinitis, reversible airway obstruction, adult respiratory distress syndrome, asthma, chronic obstructive pulmonary disease (COPD) and/or bronchitis. It is contemplated that a compound of this invention may be useful in treating one or more of the diseases listed.

In another aspect, the invention provides a method of preparing a pharmaceutical composition for treating the disorders associated with TACE, aggrecanase, TNF-α, MMPs, ADAMs or any combination thereof, said method comprising bringing into intimate contact at least one compound of Formulae (I)-(IX) and at least one pharmaceutically acceptable carrier.

In another aspect, the invention provides a compound of Formulae (I)-(IX) exhibiting TACE, TNF-α, MMPs, ADAMs or any combination thereof inhibitory activity, including enantiomers, stereoisomers and tautomers of said compound, and pharmaceutically acceptable salts, solvates, or esters of said compound, said compound being selected from the compounds of structures listed in Table 1 set forth below.

In another aspect, the invention provides a pharmaceutical composition for treating disorders associated with TACE, aggrecanase, TNF-α, MMP, ADAM or any combination thereof in a patient comprising, administering to the patient in need of such treatment a therapeutically effective amount of at least one compound of Formulae (I)-(IX) or a pharmaceutically acceptable salt, solvate, ester, or isomer thereof.

In another aspect, the invention provides a compound of Formulae (I)-(IX) in purified form.

In another aspect, the invention provides a method of treating a condition or disease mediated by TACE, MMPs, TNF-α, aggrecanase, or any combination thereof in a patient comprising: administering to the patient in need of such treatment a therapeutically effective amount of at least one compound of Formulae (I)-(IX) or a pharmaceutically acceptable salt, solvate, ester or isomer thereof.

In another aspect, the invention provides a method of treating a condition or disease selected from the group consisting of rheumatoid arthritis, osteoarthritis, periodontitis, gingivitis, corneal ulceration, solid tumor growth and tumor invasion by secondary metastases, neovascular glaucoma, inflammatory bowel disease, multiple sclerosis and psoriasis in a patient, comprising:
administering to the patient in need of such treatment a therapeutically effective amount of at least one compound of Formulae (I)-(IX) or a pharmaceutically acceptable salt, solvate, ester or isomer thereof.

In another aspect, the invention provides a method of treating a condition or disease selected from the group consisting of fever, cardiovascular conditions, hemorrhage, coagulation, cachexia, anorexia, alcoholism, acute phase response, acute infection, shock, graft versus host reaction, autoimmune disease and HIV infection in a patient comprising administering to the patient in need of such treatment a therapeutically effective amount of at least one compound of Formulae (I)-(IX) or a pharmaceutically acceptable salt, solvate, ester, or isomer thereof.

In another aspect, the invention provides a method of treating a condition or disease selected from the group consisting of septic shock, haemodynamic shock, sepsis syndrome, post ischaemic reperfusion injury, malaria, mycobacterial infection, meningitis, psoriasis, congestive heart failure, fibrotic diseases, cachexia, graft rejection, cancers such as cutaneous T-cell lymphoma, diseases involving angiogenesis, autoimmune diseases, skin inflammatory diseases, inflammatory bowel diseases such as Crohn's disease and colitis, osteo and rheumatoid arthritis, ankylosing spondylitis, psoriatic arthritis, adult Still's disease, ureitis, Wegener's granulomatosis, Behcehe disease, Sjogren's syndrome, sarcoidosis, polymyositis, dermatomyositis, multiple sclerosis, sciatica, complex regional pain syndrome, radiation damage, hyperoxic alveolar injury, periodontal disease, HIV, non-insulin dependent diabetes mellitus, systemic lupus erythematosus, glaucoma, sarcoidosis, idiopathic pulmonary fibrosis, bronchopulmonary dysplasia, retinal disease, scleroderma, osteoporosis, renal ischemia, myocardial infarction, cerebral stroke, cerebral ischemia, nephritis, hepatitis, glomerulonephritis, cryptogenic fibrosing aveolitis, transplant rejection, atopic dermatitis, vasculitis, allergy, seasonal allergic rhinitis, reversible airway obstruction, adult respiratory distress syndrome, asthma, chronic obstructive pulmonary disease (COPD) and bronchitis in a patient comprising administering to the patient in need of such treatment a therapeutically effective amount of at least one compound of Formulae (I)-(IX) or a pharmaceutically acceptable salt, solvate, ester or isomer thereof.

In another aspect, the invention provides a method of treating a condition or disease selected from the group consisting of rheumatoid arthritis, psoriasis, psoriatic arthritis, ankylosing spondylitis, Crohn's disease, and ulcerative colitis, comprising: administering to a patient in need of such treatment a therapeutically effective amount of at least one compound of Formulae (I)-(IX) or a pharmaceutically acceptable salt, solvate, ester or isomer thereof.

In another aspect, the invention provides a method of treating rheumatoid arthritis, psoriasis, or inflammatory bowel disease (e.g., Crohn's disease or ulcerative colitis) comprising: administering to a patient in need of such treatment a therapeutically effective amount of at least one compound of Formulae (I)-(IX) or a pharmaceutically acceptable salt, solvate, ester or isomer thereof.

In another aspect, the invention provides a method of treating a condition or disease associated with COPD, comprising: administering to the patient in need of such treatment a therapeutically effective amount of at least one compound of Formulae (I)-(IX) or a pharmaceutically acceptable salt, solvate, ester or isomer thereof.

In another aspect, the invention provides a method of treating a condition or disease associated with rheumatoid arthritis, comprising:
administering to the patient in need of such treatment a therapeutically effective amount of at least one compound of Formulae (I)-(IX) or a pharmaceutically acceptable salt, solvate, ester, or isomer thereof.

In another aspect, the invention provides a method of treating a condition or disease associated with Crohn's disease, comprising:
administering to the patient in need of such treatment a therapeutically effective amount of at least one compound of Formulae (I)-(IX) or a pharmaceutically acceptable salt, solvate, ester or isomer thereof.

In another aspect, the invention provides a method of treating a condition or disease associated with psoriasis, comprising: administering to the patient in need of such treatment a therapeutically effective amount of at least one compound of Formulae (I)-(IX) or a pharmaceutically acceptable salt, solvate, ester, or isomer thereof. In specific embodiments, the therapeutically effective amount of the at least one compound of Formulae (I)-(IX) or a pharmaceutically acceptable salt, solvate, ester, or isomer thereof is topically administered to the patient in need of treatment for psoriasis.

In another aspect, the invention provides a method of treating a condition or disease associated with ankylosing spondylitis, comprising:
administering to the patient in need of such treatment a therapeutically effective amount of at least one compound of Formulae (I)-(IX) or a pharmaceutically acceptable salt, solvate, ester or isomer thereof.

In another aspect, the invention provides a method of treating a condition or disease associated with sciatica, comprising: administering to the patient in need of such treatment a therapeutically effective amount of at least one compound of Formulae (I)-(IX) or a pharmaceutically acceptable salt, solvate, ester or isomer thereof.

In another aspect, the invention provides a method of treating a condition or disease associated with complex regional pain syndrome, comprising: administering to the patient in need of such treatment a therapeutically effective amount of at least one compound of Formulae (I)-(IX) or a pharmaceutically acceptable salt, solvate, ester, or isomer thereof.

In another aspect, the invention provides a method of treating a condition or disease associated with psoriatic arthritis, comprising:
administering to the patient in need of such treatment a therapeutically effective amount of at least one compound of Formulae (I)-(IX), or a pharmaceutically acceptable salt, solvate, ester, or isomer thereof.

In another aspect, the invention provides a method of treating a condition or disease associated with multiple sclerosis, comprising:
administering to the patient in need of such treatment a therapeutically effective amount of at least one compound of Formulae (I)-(IX) or a pharmaceutically acceptable salt, solvate, ester or isomer thereof, in combination with a compound selected from the group consisting of Avonex®, Betaseron, Copaxone or other compounds indicated for the treatment of multiple sclerosis.

Additionally, a compound of the present invention may be co-administered or used in combination with disease-modifying antirheumatic drugs (DMARDS) such as methotrexate, azathioprine, leflunomide, pencillinamine, gold salts, mycophenolate mofetil, cyclophosphamide and other similar drugs. They may also be co-administered with or used in combination with non-steroidal anti-inflammatory drugs (NSAIDs) such as piroxicam, naproxen, indomethacin, ibuprofen and the like; cycloxygenase-2 selective (COX-2) inhibitors such as Vioxx® and Celebrex®; immunosuppressives such as steroids, cyclosporin, Tacrolimus, rapamycin and the like; biological response modifiers (BRMs) such as Enbrel®, Remicade®, IL-1 antagonists, anti-CD40, anti-CD28, IL-10, anti-adhesion molecules and the like; and other anti-inflammatory agents such as p38 kinase inhibitors, PDE4 inhibitors, other chemically different TACE inhibitors, chemokine receptor antagonists, Thalidomide and other small molecule inhibitors of pro-inflammatory cytokine production.

Also, a compound of the present invention may be co-administered or used in combination with an H1 antagonist for the treatment of seasonal allergic rhinitis and/or asthma. Suitable H1 antagonists may be, for example, Claritin®, Clarinex®, Allegra®, or Zyrtec®.

In another aspect, the invention provides a method of treating a condition or disease mediated by TACE, MMPs, TNF-α, aggrecanase, or any combination thereof in a patient comprising: administering to the patient in need of such treatment a therapeutically effective amount of at least one compound of Formulae (I)-(IX) or a pharmaceutically acceptable salt, solvate or isomer thereof in combination with a therapeutically effective amount of at least one medicament selected from the group consisting of disease modifying anti-rheumatic drugs (DMARDS), NSAIDs, COX-2 inhibitors, COX-1 inhibitors, immunosuppressives, biological response modifiers (BRMs), anti-inflammatory agents and H1 antagonists.

In another aspect, the invention provides a method of treating a condition or disease selected from the group consisting of rheumatoid arthritis, osteoarthritis, periodontitis, gingivitis, corneal ulceration, solid tumor growth and tumor invasion by secondary metastases, neovascular glaucoma, inflammatory bowel disease, multiple sclerosis and psoriasis in a patient, comprising:
administering to the patient in need of such treatment a therapeutically effective amount of at least one compound of Formulae (I)-(IX) or a pharmaceutically acceptable salt, solvate, ester, or isomer thereof in combination with a therapeutically effective amount of at least one medicament selected from the group consisting of DMARDS, NSAIDs, COX-2 inhibitors, COX-1 inhibitors, immunosuppressives, BRMs, anti-inflammatory agents and H1 antagonists.

In another aspect, the invention provides a method of treating a condition or disease selected from the group consisting of fever, cardiovascular conditions, hemorrhage, coagulation, cachexia, anorexia, alcoholism, acute phase response, acute infection, shock, graft versus host reaction, autoimmune disease, and HIV in a patient, comprising administering to the patient in need of such treatment a therapeutically effective amount of at least one compound of Formulae (I)-(IX) or a pharmaceutically acceptable salt, solvate, ester, or isomer thereof in combination with a therapeutically effective amount of at least one medicament selected from the group consisting of DMARDS, NSAIDs, COX-2 inhibitors, COX-1 inhibitors, immunosuppressives, BRMs, anti-inflammatory agents and H1 antagonists.

In another aspect, the invention provides a method of treating a condition or disease selected from the group consisting of septic shock, haemodynamic shock, sepsis syndrome, post ischaemic reperfusion injury, malaria, mycobacterial infection, meningitis, psoriasis, congestive heart failure, fibrotic diseases, cachexia, graft rejection, cancers such as cutaneous T-cell lymphoma, diseases involving angiogenesis, autoimmune diseases, skin inflammatory diseases, inflammatory bowel diseases such as Crohn's disease and colitis, osteo and rheumatoid arthritis, ankylosing spondylitis, psoriatic arthritis, adult Still's disease, ureitis, Wegener's granulomatosis, Behcehe disease, Sjogren's syndrome, sarcoidosis, polymyositis, dermatomyositis, multiple sclerosis, sciatica, complex regional pain syndrome, radiation damage, hyperoxic alveolar injury, periodontal disease, HIV, non-insulin dependent diabetes mellitus, systemic lupus erythematosus, glaucoma, sarcoidosis, idiopathic pulmonary fibrosis, bronchopulmonary dysplasia, retinal disease, scleroderma, osteoporosis, renal ischemia, myocardial infarction, cerebral stroke, cerebral ischemia, nephritis, hepatitis, glomerulonephritis, cryptogenic fibrosing aveolitis, transplant rejection, atopic dermatitis, vasculitis, allergy, seasonal allergic rhinitis, reversible airway obstruction, adult respiratory distress syndrome, asthma, chronic obstructive pulmonary disease (COPD) and bronchitis in a patient comprising administering to the patient in need of such treatment a therapeutically effective amount of at least one compound of Formulae (I)-(IX), or a pharmaceutically acceptable salt, solvate, ester or isomer thereof in combination with a therapeutically effective amount of at least one medicament selected from the group consisting of DMARDS, NSAIDs, COX-2 inhibitors, COX-1 inhibitors, immunosuppressives, BRMs, anti-inflammatory agents and H1 antagonists.

In another aspect, the invention provides a method for treating RA comprising administering a compound of the Formulae (I)-(IX) in combination with compound selected from the class consisting of a COX-2 inhibitor e.g. Celebrex® or Vioxx®; a COX-1 inhibitor, e.g., Feldene®; an immunosuppressive e.g. methotrexate or cyclosporin; a steroid e.g. β-methasone; and anti-TNF-α compound, e.g. Enbrei® or Remicade®; a PDE IV inhibitor, or other classes of compounds indicated for the treatment of RA.

In another aspect, the invention provides a method for treating multiple sclerosis comprising administering a compound of the Formulae (I)-(IX) in combination with a compound selected from the group consisting of Avonex®, Betaseron, Copaxone or other compounds indicated for the treatment of multiple sclerosis.

TACE activity is determined by a kinetic assay measuring the rate of increase in fluorescent intensity generated by TACE catalyzed cleavage of an internally quenched peptide substrate (SPDL-3). The purified catalytic domain of recombinant human TACE (rhTACEc, Residue 215 to 477 with two mutations (S266A and N452Q) and a 6×His tail) is used in the assay. It is purified from the baculovirus/Hi5 cells expression system using affinity chromatography. The substrate SPDL-3 is an internally quenched peptide (MCA-Pro-Leu-Ala-Gln-Ala-Val-Arg-Ser-Ser-Ser-Dpa-Arg-NH2), with its sequence derived from the pro-TNFα cleavage site. MCA is (7-Methoxycoumarin-4-yl)acetyl. Dpa is N-3-(2,4-Dinitrophenyl)-L-2,3-diaminopropionyl.

A 50 µl assay mixture contains 20 mM HEPES, pH 7.3, 5 mM $CaCl_2$, 100 µM $ZnCl_2$, 2% DMSO, 0.04% Methylcellulose, 30 µM SPDL-3, 70 pM rhTACEc and a test compound. RhTACEc is pre-incubated with the test compound for 90 min. at 25° C. Reaction is started by addition of the substrate. The fluorescent intensity (excitation at 320 nm, emission at 405 nm) was measured every 45 seconds for 30 min. using a fluorospectrometer (GEMINI XS, Molecular Devices). Rate of enzymatic reaction is shown as Units per second. Effect of a test compound is shown as % of TACE activity in the absence of the compound.

The compounds' ability to inhibit TACE activity can also be determined in human whole blood using the assay conditions described in Example 35 below.

The pharmaceutical compositions containing the active ingredient may be in a form suitable for oral use, for example, as tablets, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients that are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in U.S. Pat. Nos. 4,256,108; 4,166,452; and 4,265,874 to form osmotic therapeutic tablets for controlled release.

The term pharmaceutical composition is also intended to encompass both the bulk composition and individual dosage units comprised of more than one (e.g., two) pharmaceutically active agents such as, for example, a compound of the present invention and an additional agent selected from the lists of the additional agents described herein, along with any pharmaceutically inactive excipients. The bulk composition and each individual dosage unit can contain fixed amounts of the afore-said "more than one pharmaceutically active agents". The bulk composition is material that has not yet been formed into individual dosage units. An illustrative dosage unit is an oral dosage unit such as tablets, pills and the like. Similarly, the herein-described method of treating a patient by administering a pharmaceutical composition of the present invention is also intended to encompass the administration of the afore-said bulk composition and individual dosage units.

Formulations for oral use may also be presented as hard gelatin capsules wherein the active ingredients is mixed with an inert solid diluent, for example, calcium carbonate, calcium phosphate or kaolin, or a soft gelatin capsules where in the active ingredient is mixed with water or an oil medium, for example peanut oil, liquid paraffin or olive oil.

Aqueous suspensions contain the active material in admixture with excipients suitable for the manufacture of aqueous suspensions. Such excipients are suspending agents, for example, sodium carboxymethylcellulose, methylcellulose, hydroxypropylmethyl-cellulose, sodium alginate, polyvinyl-pyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example, heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example, polyethylene sorbitan monooleate. The aqueous suspensions may also contain one or more preservatives, for example, ethyl or n-propyl, p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example, arachis oil, olive oil, sesame oil or coconut oil, or in mineral oil such as liquid paraffin. The oily suspensions may contain a thickening agent, for example, beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, e.g., sweetening, flavoring and coloring agents, may also be present.

The pharmaceutical compositions of the invention may also be in the form of an oil-in-water emulsion. The oily phase may be a vegetable oil, e.g., olive oil or arachis oil, or a mineral oil, e.g., liquid paraffin or mixtures of these. Suitable emulsifying agents may be naturally-occurring phosphatides, e.g., soy beans, lecithin, and esters or partial esters derived from fatty acids and hexitol anhydrides, for example, sorbitan monooleate, and condensation products of the said partial esters with ethylene oxide, e.g., polyoxyethylene sorbitan monooleate. The emulsions may also contain sweetening and flavoring agents.

Syrups and elixirs may be formulated with sweetening agents, for example, glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, e.g., as a solution in 1,3-butane diol. Among the acceptable vehicles and solvents that may be employed are water, Ringer's solution and isotonic sodium chloride solution. In addition, sterile fixed oils are conventionally employed as a solvent or suspending medium. For this purpose any bland fixed oil may be employed including synthetic mono- or diglycerides. In addition, fatty acids such as oleic acid find use in the preparation of injectables.

Compounds of the invention may also be administered in the form of suppositories for rectal administration of the drug. The compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compounds of the invention are employed. (For purposes of this application, topical application shall include mouthwashes and gargles.)

The compounds for the present invention can be administered in the intranasal form via topical use of suitable intranasal vehicles, or via transdermal routes, using those forms of transdermal skin patches well known to those of ordinary skill in the art. To be administered in the form of a transdermal delivery system, the dosage administration will, of course, be continuous rather than intermittent throughout the dosage regimen. Compounds of the present invention may also be delivered as a suppository employing bases such as cocoa butter, glycerinated gelatin, hydrogenated vegetable oils, mixtures of polyethylene glycols of various molecular weights and fatty acid esters of polyethylene glycol.

The dosage regimen utilizing the compounds of the present invention is selected in accordance with a variety of factors including type, species, weight, sex and medical condition of the patient; the severity of the condition to be treated; the route of administration; the renal and hepatic function of the patient; and the particular compound thereof employed. A physician or veterinarian of ordinary skill can readily determine and prescribe the effective amount of the drug required to prevent, counter, arrest or reverse the progress of the condition. Optimal precision in achieving concentration of drug within the range that yields efficacy without toxicity requires a regimen based on the kinetics of the drug's availability to target sites. This involves a consideration of the distribution, equilibrium, and elimination of a drug. Preferably, doses of the compound of Formulae (I)-(iX) useful in the method of the present invention range from 0.01 to 1000 mg per day. More preferably, dosages range from 0.1 to 1000 mg/day. Most preferably, dosages range from 0.1 to 500 mg/day. For oral administration, the compositions are preferably provided in the form of tablets containing 0.01 to 1000 milligrams of the active ingredient, particularly 0.01, 0.05, 0.1, 0.5, 1.0, 2.5, 5.0, 10.0, 15.0, 25.0, 50.0, 100 and 500 milligrams of the active ingredient for the symptomatic adjustment of the dosage to the patient to be treated. An effective amount of the drug is ordinarily supplied at a dosage level of from about 0.0002 mg/kg to about 50 mg/kg of body weight per day. The range is more particularly from about 0.001 mg/kg to 1 mg/kg of body weight per day.

Advantageously, the active agent of the present invention may be administered in a single daily dose, or the total daily dosage may be administered in dividend doses of two, three or four time daily.

The amount of active ingredient that may be combined with the carrier materials to produce single dosage form will vary depending upon the host treated and the particular mode of administration.

It will be understood, however, that the specific dose level for any particular patient will depend upon a variety of factors including the age, body weight, general health, sex, diet, time of administration, route or administration, rate of excretion, drug combination and the severity of the particular disease undergoing therapy.

The compounds of the invention may be produced by processes known to those skilled in the art and as shown in the following reaction schemes and in the preparations and examples described below.

EXAMPLES

General

The following abbreviations are used in the procedures and schemes:

| ACN | Acetonitrile |
|---|---|
| AcOH | Acetic acid |
| Aq | Aqueous |
| BINAP | 2,2'-bis(diphenylphosphino)-1,1'-binaphthalene |
| BOC | tert-Butoxycarbonyl |
| BOC-ON | [2-(tert-butoxycarbonyloxyimino)-2-phenylacetonitril] |
| BOC$_2$O | BOC Anhydride |
| C. | degrees Celsius |
| Calcd | Calculated |
| CBZCl | Benzyl chloroformate |
| CDI | Carbonyldiimidazole |
| dba | Dibenzylideneacetone |
| DBU | 1,8-Diazabicyclo[5.4.0]undec-7-ene |
| DCE | 1,2-Dichloroethane |
| DCM | Dichloromethane |
| DEAD | Diethyl azodicarboxylate |
| (DHQ)2PHAL | Hydroquinine 1,4-phthalazinediyl diether |
| DIAD | Diisopropylazodicarboxylate |
| DIPEA | Diisopropylethylamine |
| DMA | N,N-Dimethylacetamide |
| DMAP | 4-Dimethylaminopyridine |
| DME | Dimethoxyethane |
| DMF | Dimethylformamide |
| DMFDMA | N,N-Dimethylformamide dimethylacetal |
| DMPU | 1,3-Dimethyl-3,4,5,6-tetrahydro-2(1h)-pyrimidinone |
| DMSO | Dimethyl sulfoxide |
| dppf | 1,1'-Bis(diphenylphosphino)ferrocene |
| EDCI | 1-(3-Dimethylaminopropyl)-3-ethylcarbodiimide hydrochloride |
| EI | Electron ionization |
| Eq | Equivalents |
| EtOAc | Ethyl acetate |
| EtOH | Ethanol |
| F-TEDA | 1-chloromethyl-4-fluoro-1,4-diazoniabicyclo[2,2,2]octane bis(tetrafluoroborate) |
| g | grams |
| h. | hours |
| $^1$H | proton |
| HATU | N,N,N',N'-Tetramethyl-O-(7-Azabenzotriazol-1-yl)Uronium hexafluorophosphate |
| Hex | hexanes |
| HOBT | 1-Hydroxybenzotriazole |
| HPLC | High pressure liquid chromatography |
| LAH | Lithium aluminum hydride |
| LCMS | Liquid Chromatography Mass Spectroscopy |
| LDA | Lithium diisopropylamide |
| LHMDS | Lithium hexamethyldisilazide |
| M | Molar |
| mmol | milimolar |
| mCPBA | meta-Chloroperoxybenzoic acid |
| Me | Methyl |
| MeCN | Acetonitrile |
| MeOH | Methanol |
| min | Minutes |
| mg | Milligrams |
| MHZ | Megahertz |
| mL | Milliliter |
| MPLC | Medium Pressure Liquid Chromatography |
| MS | Mass Spectroscopy |
| N | Normal |
| NMR | Nuclear Magnetic Resonance |
| NBS | N-Bromosuccinimide |
| NCS | N-Chlorosuccinimide |
| NIS | N-Iodosuccinimide |
| nm | nanometers |
| NMM | N-Methylmorpholine |
| NMP | 1-methyl-2-pyrrolidone |
| Obsd | Observed |
| ON | Overnight |
| PCC | Pyridinium Chlorochromate |
| Ph | Phenyl |
| PTLC | Preparative thin layer chromatography |
| PyBop | (Benzotriazol-1-yloxy)tripyrrolidinophosphonium hexafluorophosphate |
| PyBrOP | Bromo-tris-pyrrolidino-phosphonium hexafluorophosphate |
| Pyr | Pyridine |
| RT | Room temperature |
| SEM | 2-(Trimethylsilyl)ethoxymethyl |
| sgc | Silica gel 60 chromatography |
| soln | Solution |
| tBOC | tert-Butoxycarbonyl |
| TACE | TNF-alpha converting enzyme |
| TEA | Triethylamine |

| | |
|---|---|
| TFA | Trifluoroacetic acid |
| THF | Tetrahydrofuran |
| TLC | Thin layer chromatography |
| TMS | Trimethylsilyl |
| $t_R$ | Retention time |
| $UV_{254\,nm}$ | ultraviolet light 254 nm |

NMR spectra were acquired on the following instruments: 400 MHZ NMR (Bruker), 500 MHZ NMR (Bruker), 400 MHz NMR (Varian), 300 MHZ NMR (Varian) using $CD_3OD$, $CDCl_3$ or DMSO-$d_6$, as solvents. LC-MS data were obtained using a PESciex API 150EX quadropole mass spectrometer using electroscopy ionization.

Purification via reverse phase chromatography (Gilson) was accomplished using a C18 reverse phase column with a gradient of (0.1% formic acid) 5:95 to 90:10 acetonitrile: water, at a flow rate of 14 mL/min. Samples were collected using UV detection. Alternatively an ISCO Companion with (0.1% formic acid) 5:95 to 95:5 acetonitrile:water, at a flow rate=10-55 mL/min.

Normal phase silica gel chromatography was either accomplished on a Biotage instrument using a 60 Å 12/M, 25/M, or 40/M flash cartridges, or on a Jones Flash Master Personal instrument using Isolute flash SI 5 g, 10 g, 20 g, 50 g, or 70 g cartridges.

Scheme A:

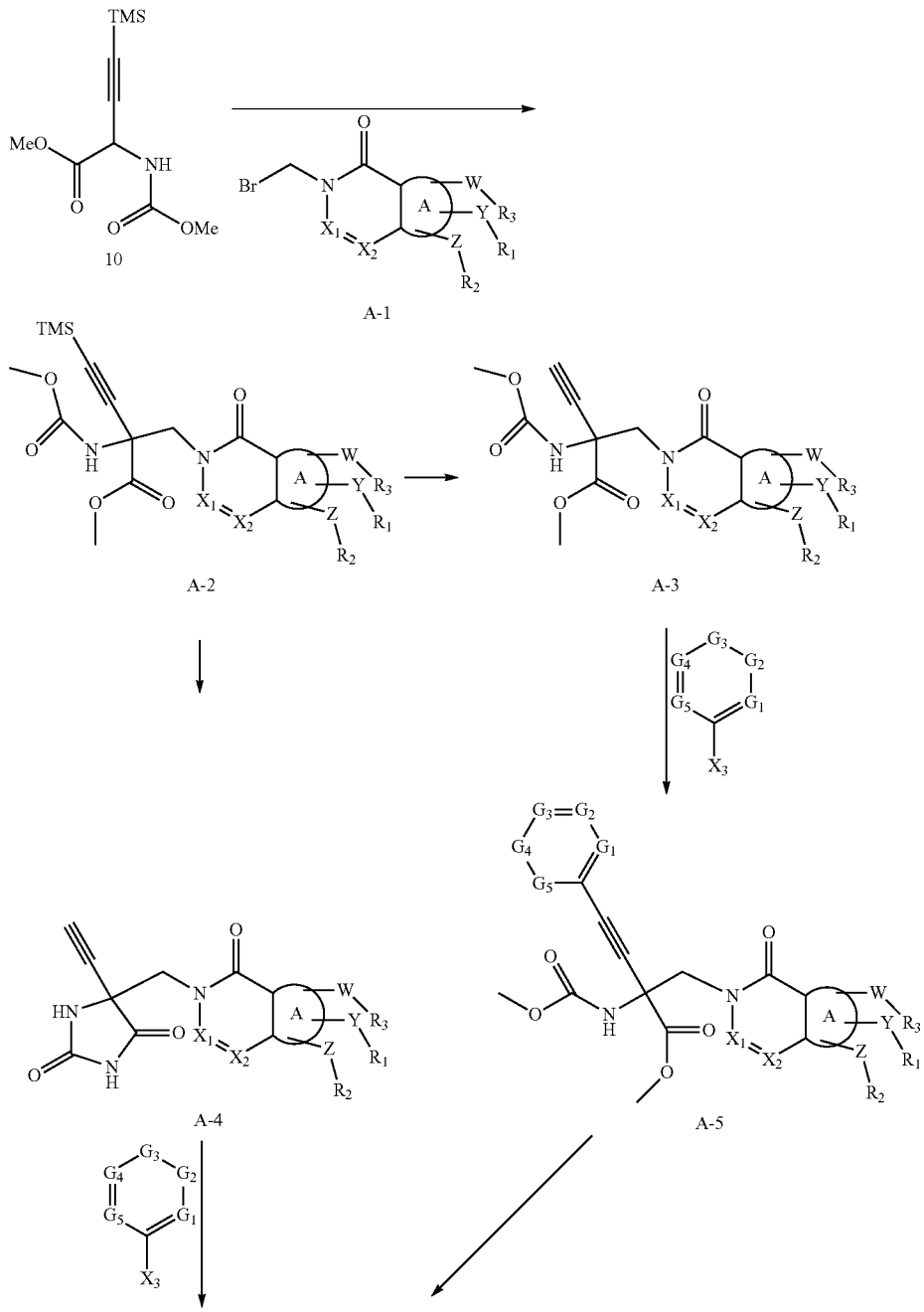

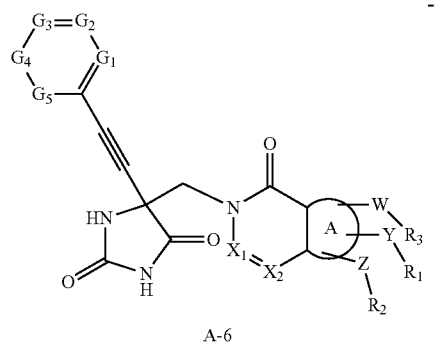

A-6

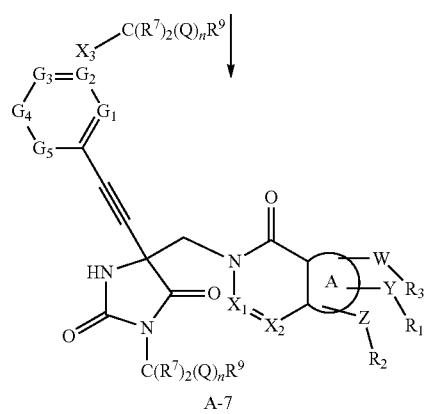

A-7

Alkylation of acetylene 10 with a suitable A-1 compound yields the quaternary protected amino acid derivative A-2. Compound A-2 may be either cyclized into hydantoin A-4 or deprotected to acetylene A-3. Introduction of the (hetero)aryl ring is readily accomplished via a Sonogashira reaction with a (hetero)arylhalide to afford intermediates A-5 or A-6. Compound A-5 is converted to A-6 by treatment with 7M ammonia in methanol solution at 80° C. in a sealed bottle. Compound A-6 may be converted to a pro-drug A-7 by treatment with a suitable alkylating agent.

Scheme B:

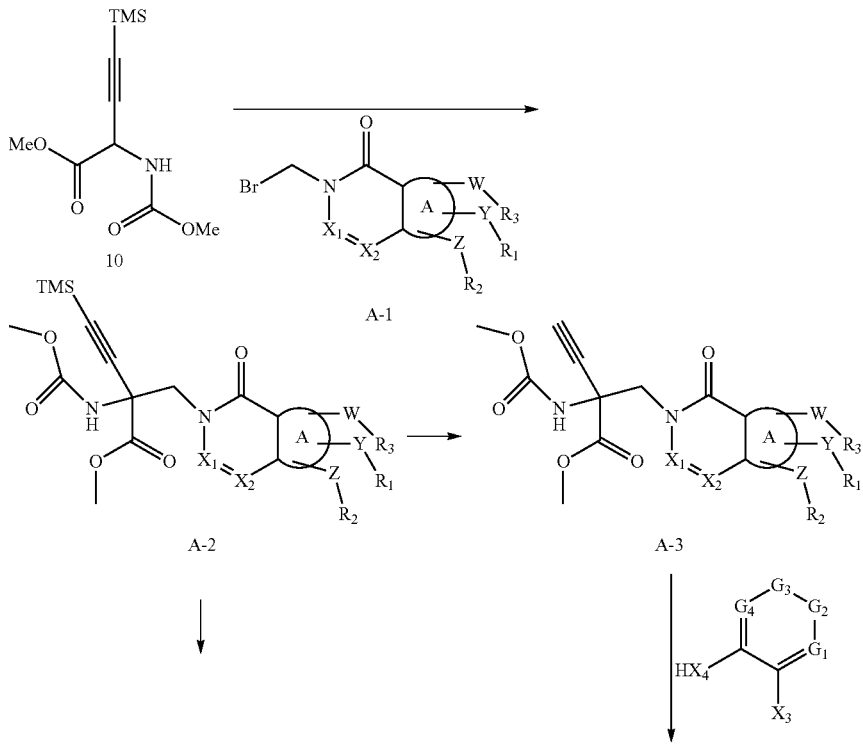

-continued

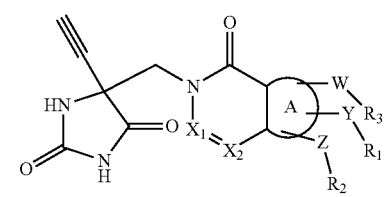
A-4

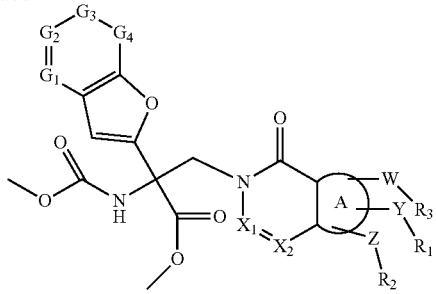
B-5

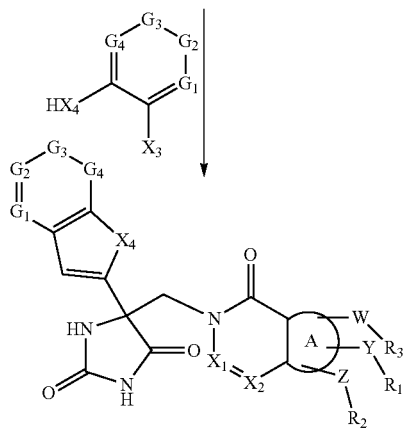
B-6

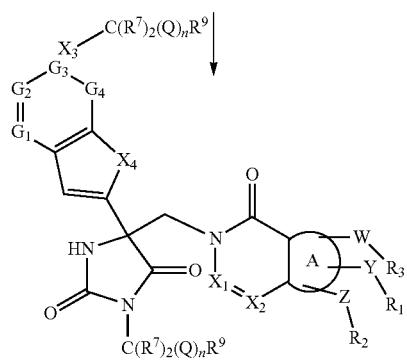
B-7

Alkylation of acetylene 10 with a suitable A-1 compound yields the quaternary protected amino acid derivative A-2. Compound A-2 may be either cyclized into hydantoin A-4 or deprotected to acetylene A-3. Conversion of the acetylene moiety to a fused biaryl ring is readily accomplished via a Sonogashira reaction with a (hetero)arylhalide to afford intermediates B-5 or B-6. Compound B-5 is converted to B-6 by treatment with 7M ammonia in methanol solution at 80° C. in a sealed bottle. Compound B-6 may be converted to a prodrug B-7 by treatment with a suitable alkylating agent.

Example 1

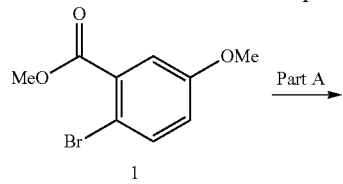
1

-continued

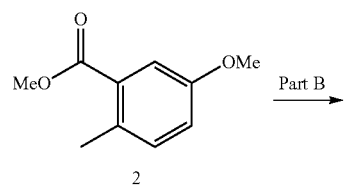
2

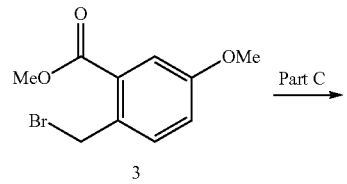
3

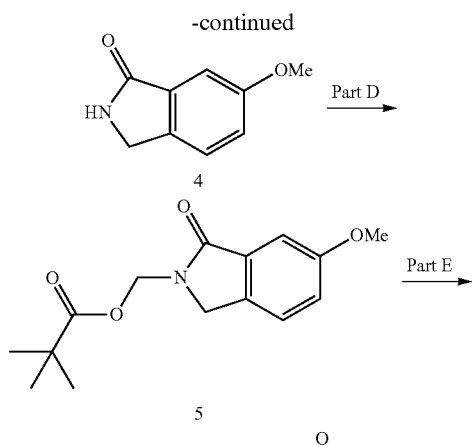

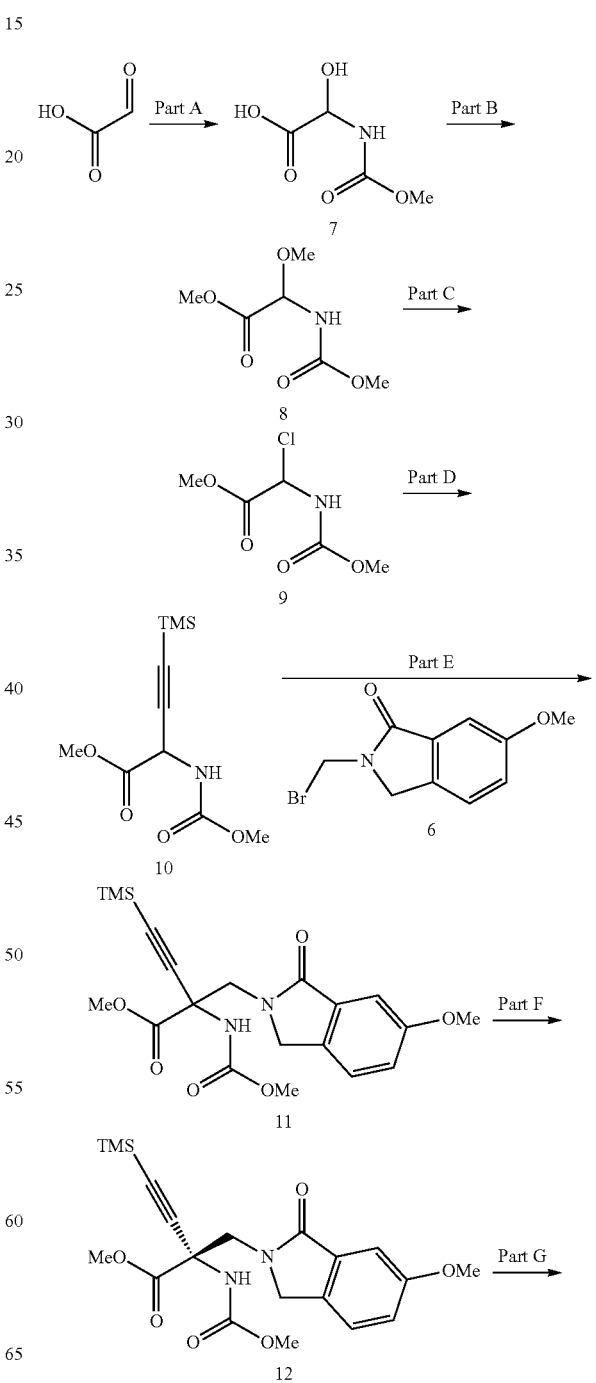

Part A:

Compound 1 (20.0 g, 81.61 mmol), trimethylboroxine (13.36 mL, 97.93 mmol), Pd(dppf)Cl₂ (1.0 g, 1.36 mmol), dioxane (350 mL), water (50 mL), and cesium carbonate (22.5 g, 163 mmol) were stirred at 110° C. (oil bath) under nitrogen for 16 hours. After cooling, the solid was removed by filtration. The solution was concentrated and purified by sgc (10:1 EtOAc/hexanes) to give 2 (12.1 g, 80%).

Part B:

Compound 2 (4.4 g, 24.2 mmol) was dissolved in carbon tetrachloride (80 mL) and N-bromosuccinimide (4.48 g, 24.2 mmol) and benzoyl peroxide (276 mg, 1.13 mmol) were added. The reaction mixture was stirred at reflux for 3 hours and then solids were filtered and washed with ether. The combined organic layers were washed with water, dried over sodium sulfate, and concentrated to provide the desired product 3 (6.1 g, 98%).

Part C:

Compound 3 (32.0 g, 124.0 mmol) was dissolved in 7 M ammonia in MeOH (150 mL) and stirred in a sealed pressure flask at 60° C. overnight. The reaction mixture was cooled and the solvent was removed under reduced pressure. The residue was suspended in ethyl acetate and stirred for 30 minutes. The solids were filtered and dissolved in methylene chloride. The organic layer was washed with water, dried over sodium sulfate, and concentrated to provide the desired product 4 (13.5 g, 67%).

Part D:

Compound 4 (2.2 g, 13.4 mmol) was dissolved in THF (250 mL) and DMPU (40 mL). Sodium t-butoxide (1.55 g, 16.13 mmol) was added and stirred for 5 hours. Chloromethylpivalate (3.0 mL, 20.1 mmol) was added dropwise and stirred overnight. The reaction was quenched with saturated ammonium chloride and extracted with ethyl acetate. The combined ethyl acetate layers were washed with water, brine, dried over sodium sulfate and concentrated. Purification by column chromatography (SiO₂, 25% ethyl acetate/hexanes) afforded the desired product 5 (2.5 g, 67%).

Part E:

Compound 5 (288 mg, 1.04 mmol) was dissolved in methylene chloride (5 mL) and cooled in an ice bath. Bromotrimethylsilane (0.3 mL, 2.08 mmol) was added dropwise and stirred in the ice bath for 30 minutes followed by 2 hours at room temperature. The reaction mixture was concentrated and re-dissolved in methylene chloride (2 mL). Hexanes (8 mL) was added and the solids were filtered to provide the desired product 6 (218 mg, 83%).

Example 2

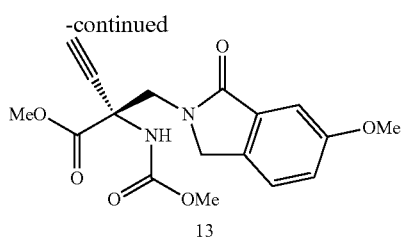

13

Part A:

Glyoxylic acid monohydrate (20.0 g, 218 mmol) and methyl carbamate (16.3 g, 218 mmol) were dissolved in diethyl ether (200 mL) and stirred overnight. The solids were filtered to provide the desired product 7 (32.0 g, 98%).

Part B:

Compound 7 (32.0 g, 214 mmol) was dissolved in MeOH (200 mL) and cooled in an ice bath. Concentrated sulfuric acid (8 mL) was added dropwise and the reaction was stirred overnight. The reaction mixture was diluted with ethyl acetate and water. The organic layer was washed with brine, dried over sodium sulfate, and concentrated to provide compound 8 that was used without purification (27.0 g, 71%).

Part C:

Compound 8 (27.0 g, 152 mmol) was dissolved in carbon tetrachloride (700 mL). Phosphorus pentachloride (50 g, 240 mmol) was added and the suspension was stirred for 18 hours (solution became clear over time). The solvent was removed under reduced pressure and the residue was stirred in petroleum ether (500 mL) overnight. The solids were filtered to provide compound 9 with no need for purification (26.5 g, 96%). Trituration step was repeated if mass yield was too high.

Part D:

Compound 9 (15.0 g, 82.7 mmol) was dissolved in methylene chloride (140 mL) and cooled in an ice bath. Bis(trimethylsilyl)acetylene (15.0 g, 88.2 mmol) was added in methylene chloride (20 mL). Freshly crushed aluminum chloride (11.0 g, 82.7 mmol) was added in portions over 20 minutes. The reaction mixture was allowed to slowly warm to room temperature and stirred overnight. The reaction was cooled in an ice bath and slowly quenched with water. The organic layer was washed several times with water, dried over sodium sulfate, and concentrated. The residue was triturated/recrystallized from hexanes to provide the desired product 10 (14.8 g, 69%). HPLC-MS $t_R$=1.84 min (ELSD); mass calculated for formula $C_{10}H_{17}NO_4Si$ 243.09, observed LCMS m/z 244.1 (M+H).

Part E:

Compound 10 (24.0 g, 98.7 mmol) and compound 6 (25.1 g, 99.0 mmol) were dissolved in THF (300 mL) and cooled to −78° C. A 1M solution of LiHMDS (198 mL, 198 mmol) was added dropwise over 30 minutes and the reaction mixture was stirred for 2 hours. Saturated ammonium chloride solution was added slowly and the reaction was allowed to warm to room temperature. The aqueous layer was extracted with ethyl acetate. The combined organic layers were washed with water, brine, dried over sodium sulfate, and concentrated. Purification by column chromatography ($SiO_2$, 33% ethyl acetate/hexanes to 50% ethyl acetate/hexanes) afforded the desired product 11 (26.0 g, 63%). HPLC-MS $t_R$=1.90 min ($UV_{254\ nm}$); mass calculated for formula $C_{20}H_{26}N_2O_6Si$ 418.15, observed LCMS m/z 419.2 (M+H).

Part F:

The two isomers were separated using a chiral OD column. One gram of material was injected into the column and the two peaks were separated by using a solvent mixture of 85% hexanes/ethanol. The second isomer was the desired compound 12 (400 mg, 80%).

Part G:

Compound 12 (8.0 g, 19.1 mmol) was dissolved in THF (250 mL) and cooled to 0° C. Tetrabutylammonium fluoride (1 M in THF, 22.9 mL, 22.9 mmol) was added dropwise and the reaction was stirred for 1 hour at room temperature. The reaction mixture was diluted with ethyl acetate and water. The organic layer was washed with water, saturated sodium bicarbonate, brine, dried over sodium sulfate and concentrated to provide compound 13 (5.8 g, 88%). The product was used without purification.

Example 3

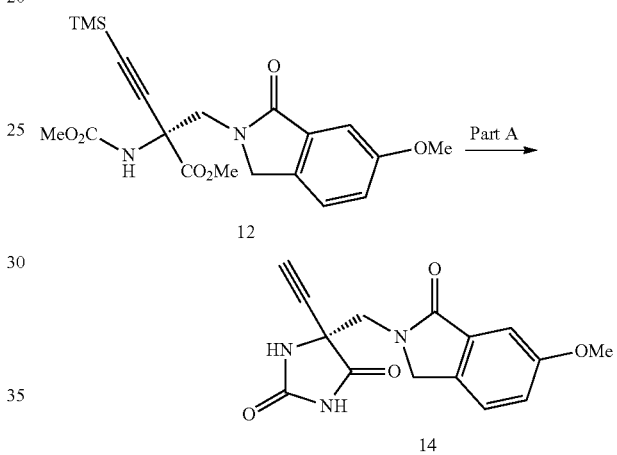

Part A:

Compound 12 (1.26 g, 3.0 mmol) in 7 M ammonia in methanol (20 mL) was heated to 85° C. in a pressure bottle overnight. The reaction mixture was concentrated to afford 14 (900 mg, 100%) which was used without further purification. HPLC-MS $t_R$=1.00 min ($UV_{254\ nm}$); mass calculated for formula $C_{15}H_{13}N_3O_4$ 299.09, observed LCMS m/z 300.1 (M+H).

Example 4

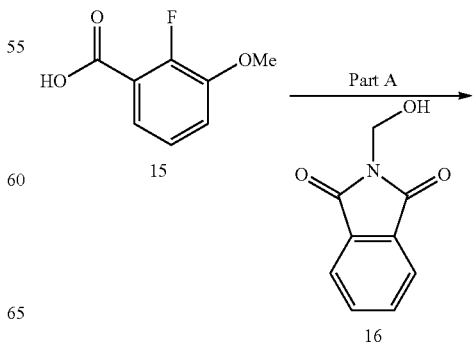

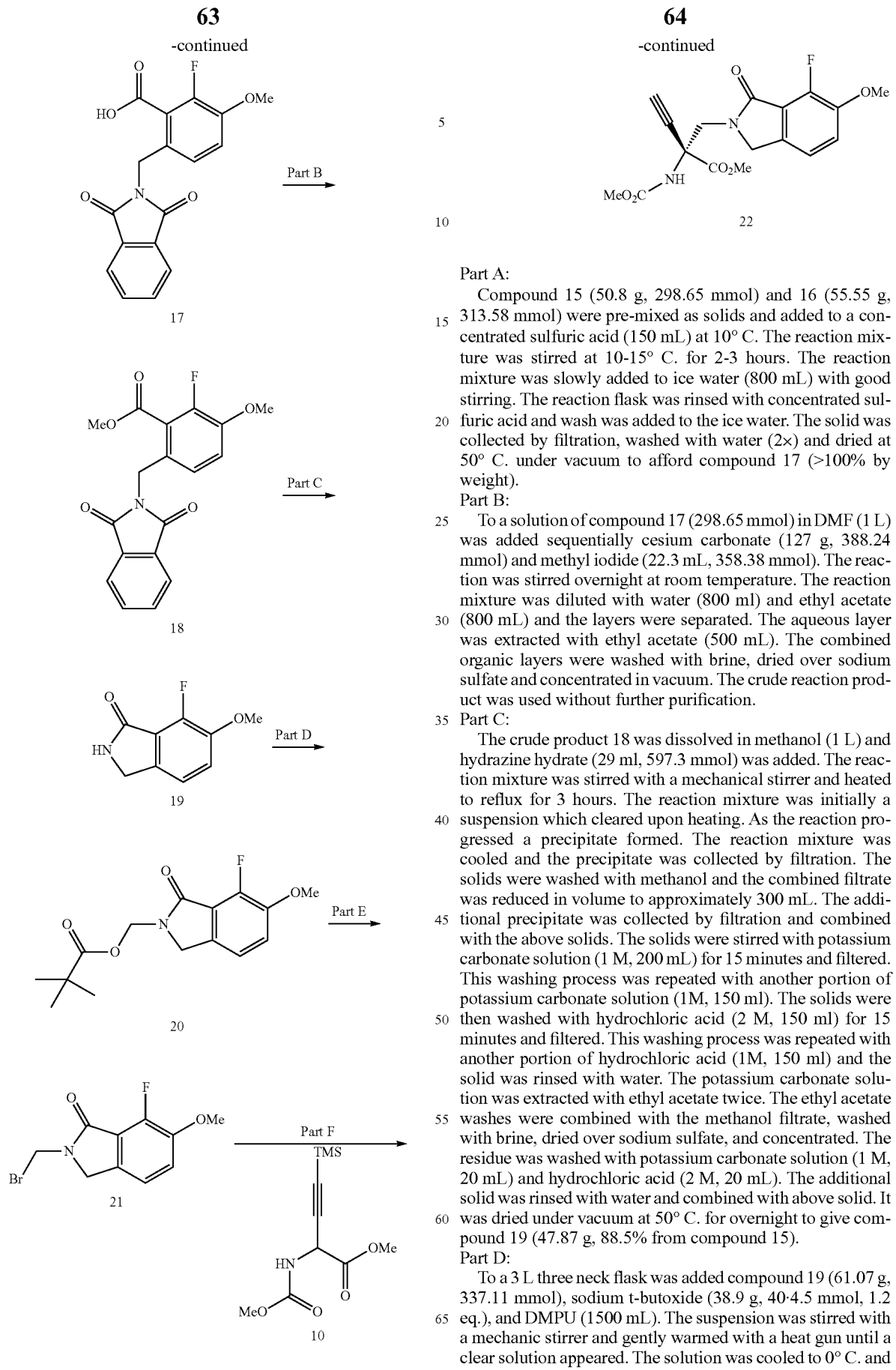

Part A:

Compound 15 (50.8 g, 298.65 mmol) and 16 (55.55 g, 313.58 mmol) were pre-mixed as solids and added to a concentrated sulfuric acid (150 mL) at 10° C. The reaction mixture was stirred at 10-15° C. for 2-3 hours. The reaction mixture was slowly added to ice water (800 mL) with good stirring. The reaction flask was rinsed with concentrated sulfuric acid and wash was added to the ice water. The solid was collected by filtration, washed with water (2×) and dried at 50° C. under vacuum to afford compound 17 (>100% by weight).

Part B:

To a solution of compound 17 (298.65 mmol) in DMF (1 L) was added sequentially cesium carbonate (127 g, 388.24 mmol) and methyl iodide (22.3 mL, 358.38 mmol). The reaction was stirred overnight at room temperature. The reaction mixture was diluted with water (800 ml) and ethyl acetate (800 mL) and the layers were separated. The aqueous layer was extracted with ethyl acetate (500 mL). The combined organic layers were washed with brine, dried over sodium sulfate and concentrated in vacuum. The crude reaction product was used without further purification.

Part C:

The crude product 18 was dissolved in methanol (1 L) and hydrazine hydrate (29 ml, 597.3 mmol) was added. The reaction mixture was stirred with a mechanical stirrer and heated to reflux for 3 hours. The reaction mixture was initially a suspension which cleared upon heating. As the reaction progressed a precipitate formed. The reaction mixture was cooled and the precipitate was collected by filtration. The solids were washed with methanol and the combined filtrate was reduced in volume to approximately 300 mL. The additional precipitate was collected by filtration and combined with the above solids. The solids were stirred with potassium carbonate solution (1 M, 200 mL) for 15 minutes and filtered. This washing process was repeated with another portion of potassium carbonate solution (1M, 150 ml). The solids were then washed with hydrochloric acid (2 M, 150 ml) for 15 minutes and filtered. This washing process was repeated with another portion of hydrochloric acid (1M, 150 ml) and the solid was rinsed with water. The potassium carbonate solution was extracted with ethyl acetate twice. The ethyl acetate washes were combined with the methanol filtrate, washed with brine, dried over sodium sulfate, and concentrated. The residue was washed with potassium carbonate solution (1 M, 20 mL) and hydrochloric acid (2 M, 20 mL). The additional solid was rinsed with water and combined with above solid. It was dried under vacuum at 50° C. for overnight to give compound 19 (47.87 g, 88.5% from compound 15).

Part D:

To a 3 L three neck flask was added compound 19 (61.07 g, 337.11 mmol), sodium t-butoxide (38.9 g, 40·4.5 mmol, 1.2 eq.), and DMPU (1500 mL). The suspension was stirred with a mechanic stirrer and gently warmed with a heat gun until a clear solution appeared. The solution was cooled to 0° C. and chloromethyl pivalate was added slowly with a syringe. The reaction mixture was stirred at 0° C. for three hours, diluted with H$_2$O (1.5 L) and EtOAc (1.5 L), and the layers were separated. The organic layer was washed with H$_2$O (500 mL×4), brine (500 mL), dried over sodium sulfate, and concentrated in vacuum. The product was purified by silica gel chromatography (Hexane/EtOAc: 2:1 to 1:1 to 0:1) to afford compound 20 (77.98 g, 78.3%)

Part E:

Compound 20 (70.97 g, 240.32 mmol) was dissolved in anhydrous CH$_2$Cl$_2$ (1 L). The solution was cooled to 0° C. and TMSBr (37.3 mL, 288.39 mmol) was added via syringe. The reaction mixture was stirred at 0° C. for two hours and concentrated in vacuum at 25° C. The residue was stirred with Hexane (500 mL) for 15 min, filtered, and rinsed with hexane (60 mL×2). The Hexane filtrate was concentrated in volume to approximately 100 mL and the additional solid was filtered, rinsed with hexane (10 mL×2), and combined with above solid. The solid was dried under vacuum for overnight to give compound 21 (64.81 g, 98.4%).

Part F:

To a flamed dried flask was added compound 21 (1.13 g, 4.11 mmol), compound 10 (1.0 g, 4.11 mmol), and anhydrous THF (25 mL). The solution was cooled to −78° C. and LiHMDS (8.63 mL, 8.63 mmol) was added via syringe. The reaction mixture was stirred at −78° C. for two hours, diluted with saturated NH$_4$Cl solution (30 mL) and EtOAc (50 mL). After warming up to room temperature, the aqueous layer was separated and extracted with EtOAc (20 mL) once. The organic layers were combined and TBAF (1 M in THF, 7 mL, 7 mmol) was added. The solution was stirred at 25° C. for 10 min, washed with water (50 mL), brine (50 mL), dried over sodium sulfate, and concentrated in vacuum. The product was purified by silica gel chromatography (Hexane/EtOAc: 2:1 to 1:1 to 0:1) to afford the racemate of compound 22 (891 mg, 59.5%)

The racemic mixture was separated using SFC conditions (20% MeOH/CO$_2$, 180 mL/min, back pressure of 225 bar, run time 9 minutes, OD-H chiral column). The racemate was dissolved in 1:1 acetonitrile/isopropyl alcohol (250 mg/mL). Compound 22 was isolated as the first peak. HPLC-MS $t_R$=1.26 min (UV 254 nm); mass calculated for formula C$_{17}$H$_{17}$FN$_2$O$_6$ 364.11, observed LCMS m/z 365.0 (M+H).

Example 5

Part A:

Using the procedures described in Example 3, compound 22 (8.69 g, 23.8 mmol) was converted to 23 in quantitative yield. HPLC-MS $t_R$=0.93 min (UV 254 nm); mass calculated for formula C$_{15}$H$_{12}$FN$_3$O$_4$ 317.08, observed LCMS m/z 318.1 (M+H).

Example 6

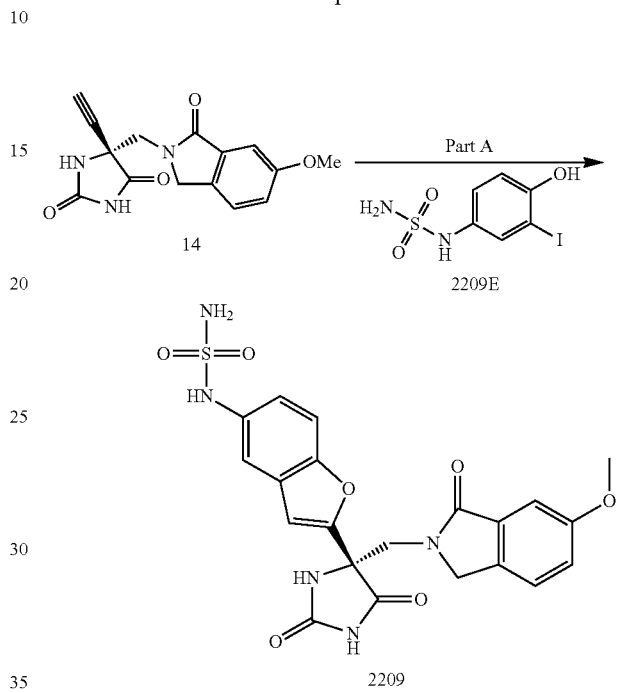

Part A:

Compound 14 (80 mg, 0.266 mmol), compound 2209E (82 mg, 0.26 mmol), Pd(dba)$_3$ (6 mg), dppf (10 mg), CuI (10 mg), and triethylamine (0.1 mL) were dissolved in DMF and stirred at 80° C. overnight. The solvent was removed under reduced pressure and the residue was purified by reverse phase chromatography (18.7 mg). HPLC-MS $t_R$=1.07 min (UV$_{254\ nm}$); mass calculated for formula C$_{21}$H$_{19}$N$_5$O$_7$S 485.1, observed LCMS m/z 486.1 (M+H). $^1$H NMR (400 MHz, DMSO-d6) δ 11.5 (s, 1H), 9.35 (s, 1H), 8.85 (s, 1H), 7.5 (m, 2H), 7.4 (d, 1H), 7.2 (d, 1H), 7.15 (m, 2H), 7.1 (d, 1H), 7.0 (s, 1H), 4.45 (m, 2H), 4.3 (m, 2H), 3.7 (s, 3H).

Example 7

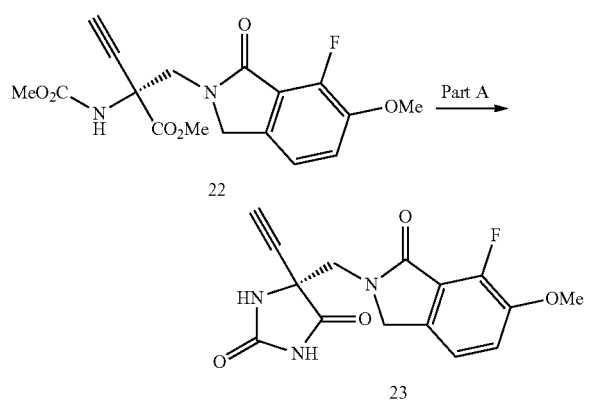

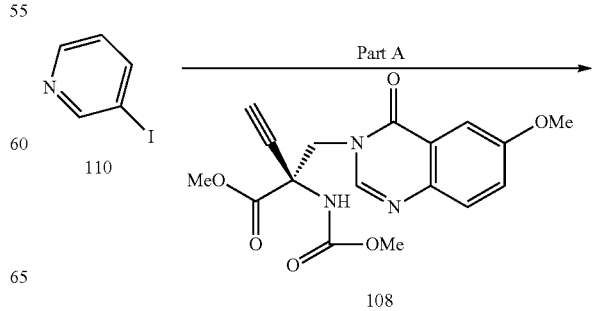

-continued

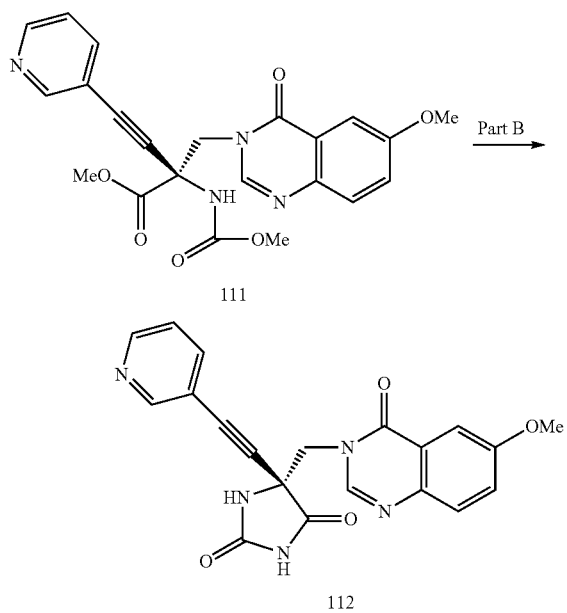

Part A:
Compound 108 (39.1 mg, 0.11 mmol), compound 110 (22.3 mg, 0.11 mmol), Pd(PPh$_3$)$_3$Cl (4 mg), CuI (1 mg), and diisopropylamine (0.3 mL) were dissolved in DMF (3.0 mL) and stirred at 80° C. overnight. The solvent was removed under reduced pressure and the residue was purified by reverse phase chromatography affording compound 111 (22 mg). HPLC-MS t$_R$=1.55 min (ELSD); mass calculated for formula C$_{22}$H$_{20}$N$_4$O$_6$ 436.2, observed LCMS m/z 437.2 (M+H).

Part B:
Compound 111 (22.0 mg, 0.050 mmol) in 7 M ammonia in methanol (3 mL) was heated to 85° C. in a pressure bottle overnight. The solvent was removed under reduced pressure and the residue was purified by reverse phase chromatography affording compound 112 (8.5 ma, 43%) HPLC-MS t$_R$=1.40 min (ELSD); mass calculated for formula C$_{20}$H$_{15}$N$_9$O$_4$ 389.1, observed LCMS m/z 390.1 (M+H).

Example 8

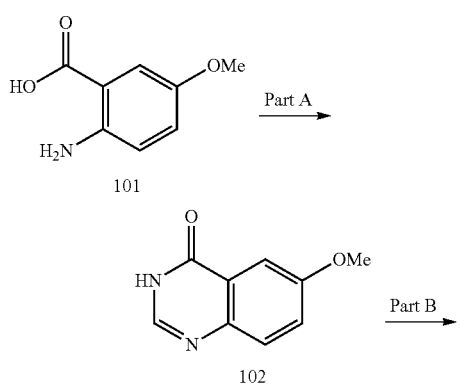

-continued

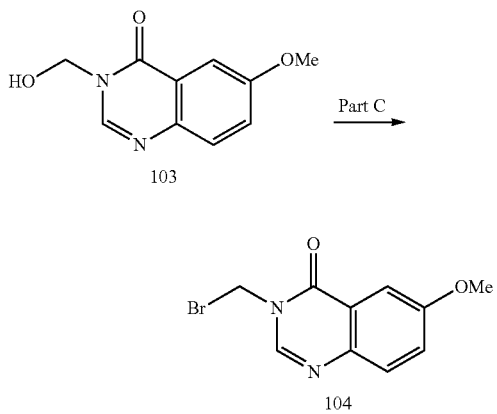

Part A:
Compound 101 (5.0 g, 30.0 mmol), formamidine acetate (9.37 g, 90.0 mmol), and 2-methoxyethanol (80 mL) were refluxed for 16 h. After cooling, the reaction mixture was poured into water (1 L) and stirred for 0.5 h. The solid was isolated by vacuum filtration to provide white solid 102 (5.3 g, 73%). HPLC-MS t$_R$=0.85 min (ELSD); mass calculated for formula C$_9$H$_8$N$_2$O$_2$ 176.1, observed LCMS m/z 177.1 (M+H).

Part B:
Compound 102 (2.85 g, 16.2 mmol), 37% aq. formaldehyde (15 mL), and water (100 mL) were heated at reflux for 2 h. The reaction was cooled to 0° C. and white solid was isolated by vacuum filtration to provide the desired product 103 (2.8 g, 85%). $^1$H NMR (400 MHz, DMSO-d$_6$) δ 8.27 (s, 1H), 7.64 (d, 1H), 7.54 (d, 1H), 7.44 (dd, 1H), 6.74 (t, 1H), 5.35 (d, 2H), 3.88 (s, 3H).

Part C:
Compound 103 (750 mg, 3.6 mmol) and triphenylphosphine (1.91 g, 7.3 mmol) were dissolved in DCM (200 mL) and allowed to stir for 5 min at RT. To the solution, carbon tetrabromide (2.42 g, 7.3 mmol) was added in one portion and stirred for 3 h. The solvent was evaporated and the crude product was purified by column chromatography (SiO$_2$, 5% methanol/dichloromethane) to provide the desired product 104 (237 mg, 24%). HPLC-MS t$_R$=1.35 min (ELSD); mass calculated for formula C$_{10}$H$_9$BrN$_2$O$_2$ 269.1, observed LCMS m/z 270.1 (M+H).

Example 9

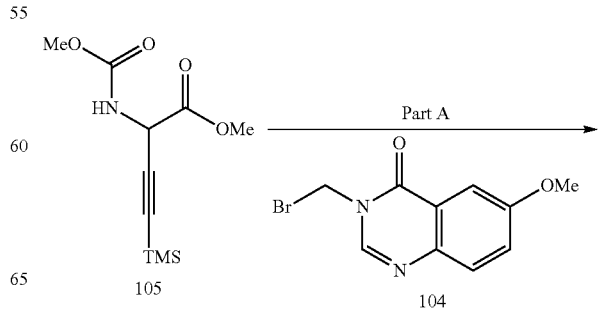

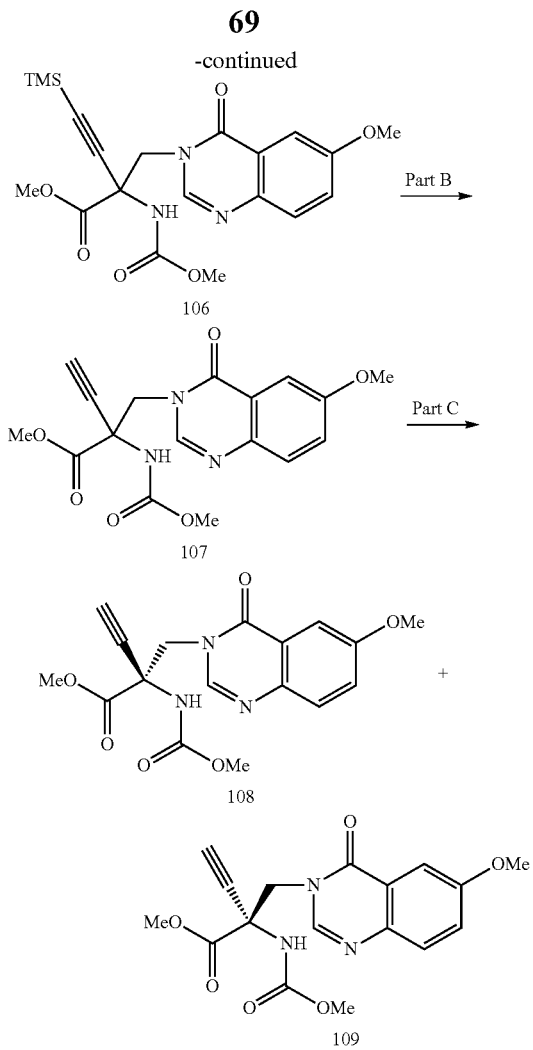

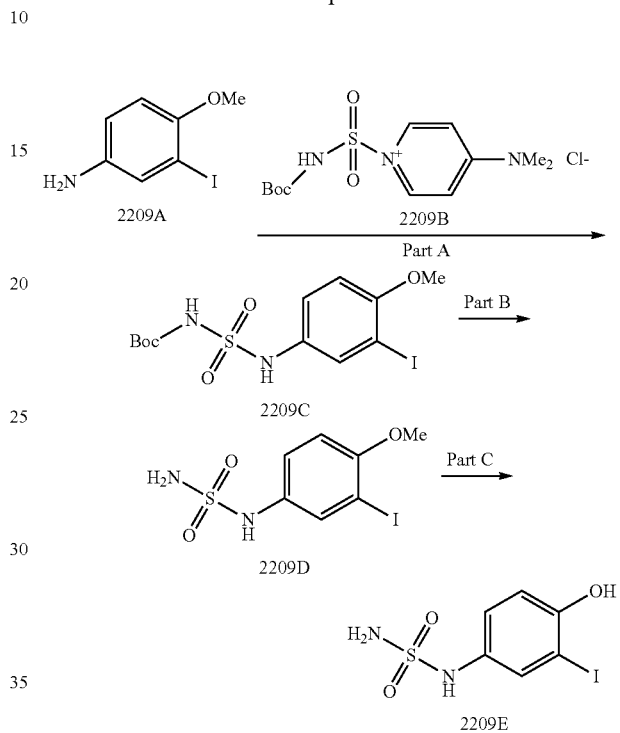

Part C:

The two isomers were separated using a chiral normal phase OD column. 107 was injected into the column and the two peaks were separated using a solvent mixture of 85% hexanes/ethanol. Isomer 108 (40.5 mg, 70%) and 109 (39.9 mg, 69%) were isolated.

Example 10

Part A:

Compound 2209A (209 mg, 0.84 mmol) and compound 2209B (311 mg, 0.92 mmol) were dissolved in methylene chloride (5 mL) and pyridine (5 mL) was added. The reaction was stirred at room temperature overnight and then quenched with 1N HCl (50 mL). The aqueous layer was extracted with ethyl acetate. The organic layer was dried over sodium sulfate and concentrated to provide the desired product (350 mg). $^1$H NMR (400 MHz, CDCl$_3$) δ 7.61 (d, 1H), 7.25 (m, 1H), 7.2 (m, 2H), 6.8 (d, 1H), 3.85 (s, 3H), 1.5 (s, 9H).

Part B:

Compound 2209C (350 mg, 0.85 mmol) was dissolved in methylene chloride (2 mL) and trifluoroacetic acid (2 mL) and stirred for 2 hours. All solvents were evaporated to provide the desired product (260 mg). $^1$H NMR (400 MHz, CDCl$_3$) δ 9.15 (s, 1H), 7.55 (d, 1H), 7.15 (m, 1H), 7.0 (s, 2H), 6.9 (d, 1H), 3.8 (s, 3H), Part C:

Compound 2209D (260 mg, 0.79 mmol) was dissolved in methylene chloride (6 mL) and 1 M boron tribromide in methylene chloride (3 mL) was added. The reaction was stirred at room temperature overnight and then quenched with water. The aqueous layer was extracted with ethyl acetate. The combined organic layers were dried over sodium sulfate and concentrated to provide the desired product (200 mg). $^1$H NMR (400 MHz, DMSO-d6) δ 10.0 (s, 1H), 8.95 (s, 1H), 7.45 (d, 1H), 7.0 (m, 1H), 6.9 (s, 2H), 6.75 (d, 1H).

Part A:

Compound 105 (212 mg, 0.87 mmol) and compound 104 (235 mg, 0.87 mmol) were dissolved in THF (30 mL) and cooled to −78° C. A 1M solution of LiHMDS (1.74 mL, 1.74 mmol) was added dropwise over 10 min and the reaction mixture was stirred for 2 h. Saturated ammonium chloride solution (100 mL) was added slowly and the reaction was allowed to warm to RT. The aqueous layer was extracted with ethyl acetate. The combined organic layers were washed with water, and brine, dried over sodium sulfate, and concentrated to dryness. Purification by reverse phase LC/MS afforded the desired product 106 (145 mg, 39%). HPLC-MS $t_R$=1.83 min (ELSD); mass calculated for formula $C_{20}H_{25}N_3O_6Si$ 431.1, observed LCMS m/z 432.1 (M+H).

Part B:

Compound 106 (140 mg, 0.32 mmol) was dissolved in THF (50 mL) and cooled to 0° C. Tetrabutylammonium fluoride (1 M in THF, 0.39 mL, 0.39 mmol) was added dropwise and the reaction was stirred for 1 h at room temperature. The reaction mixture was quenched with saturated ammonium chloride (50 mL), extracted with ethyl acetate, washed with water, brine, dried over sodium sulfate and concentrated to provide compound 107 (114 mg, 100%). HPLC-MS $t_R$=1.50 min (ELSD); mass calculated for formula $C_{17}H_{17}N_3O_6$ 359.1, observed LCMS m/z 360.1 (M+H).

Example 11

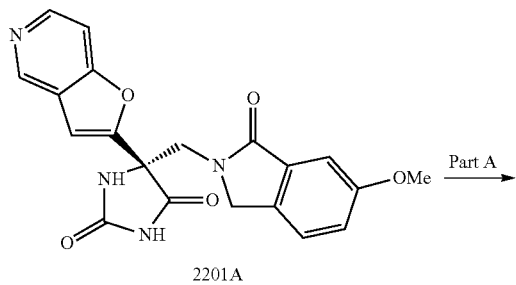

Part A:

Compound 2201A (prepared as described in Yu, W. et al., PCT Appl. WO2007084455A1) (60 mg, 0.12 mmol) and N-chlorosuccinimide (40 mg, 0.3 mmol) were dissolved in cold trifluoromethane sulfonic acid (0.5 mL) and stirred at room temperature for 2 h. The mixture was then cooled in a cold bath (−20° C.), quenched carefully with 5 mL of H$_2$O. The solution was then adjusted with 1N NaOH to pH around 7. The precipitate was collected and purified by HPLC to afford compound 2201. HPLC-MS (10 min) $t_R$=2.941 min (UV$_{254\ nm}$); mass calculated for formula C$_{20}$H$_{14}$Cl$_2$N$_4$O$_4$ 460.03, observed LCMS m/z 461.0 (M+H). $^1$H NMR (CD$_3$OD) δ (ppm): 9.30 (s, 1H), 8.76 (d, J=6.79 Hz, 1H), 8.24 (d, J=6.72 Hz, 1H), 7.98 (s, 1H), 7.63 (d, J=0.59 Hz, 1H), 7.51 (d, J=0.74 Hz, 1H), 4.57-4.35 (m, 4H), 3.89 (s, 3H).

Example 12

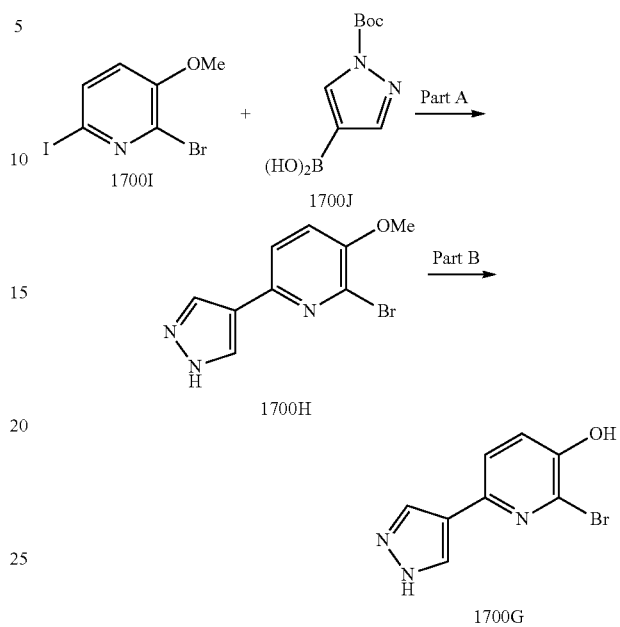

Part A:

To a pressure bottle was added compound 17001(314 mg, 1.0 mmol), compound 1700J (294 mg, 1.0 mmol), Pd(PPh$_3$)$_4$ (58 mg, 0.05 mmol), acetonitrile (5 mL) and potassium carbonate (5 mL, 1 N aq.). The reaction mixture was subjected to vacuum, and the purged with nitrogen for three times and stirred at 80° C. overnight. The reaction mixture was diluted with water (30 mL) and extracted with EtOAc (3×20 mL). The organic layers were combined and washed with brine, dried over sodium sulfate, and concentrated to dryness. The residue was purified by silica gel chromatography (Hexane/EtOAc:1:3) to afford 1700H, (110 mg, 43%).

Part B:

A mixture of compound 1700H (56 mg, 0.022 mmol) and AlCl$_3$ (70 mg, 0.055 mmol) was suspended in CH$_2$Cl$_2$ (5 mL). The reaction mixture was refluxed overnight. After cooling, the solvent was evaporated. The residue was mixed with water (10 mL) and extracted with EtOAc (10 mL×3). The organic layers were combined and washed with brine. The resulting organic layer was dried over sodium sulfate and concentrated to give compound 1700G. The compound was used in the next step without further purification.

Example 13

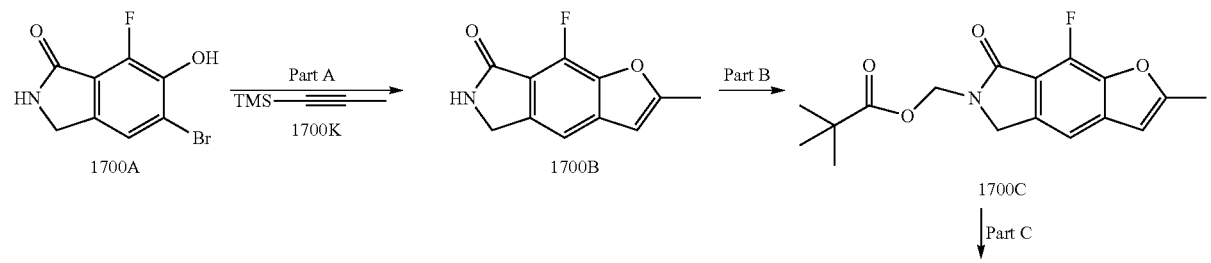

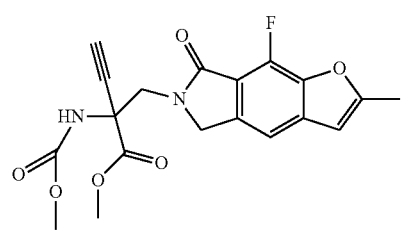
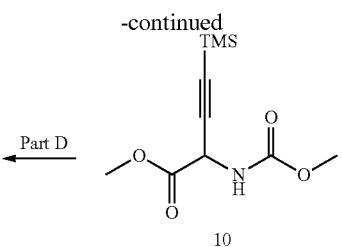
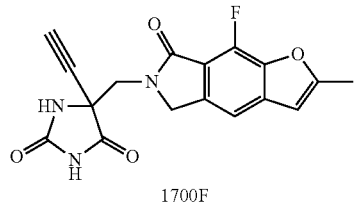
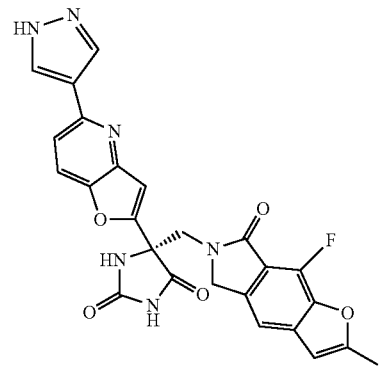

Part A:

Compound 1700A (800 mg, 3.26 mmol), compound 1700K (1.46 mL, 9.79 mmol), Pd(PPh$_3$)$_2$Cl$_2$ (183 mg, 0.26 mmol), CuI (93 mg, 4.9 mmol), and diisopropylamine (1 mL) were dissolved in DMF and stirred at 80° C. overnight. The solvent was removed under reduced pressure and the residue was diluted with CH$_2$Cl$_2$ (50 mL), washed by water and brine, and dried over sodium sulfate. The mixture was filtered. The filtrate was concentrated and the residue was purified by column chromatography (5% of 7N Ammonia in MeOH solution in CH$_2$Cl$_2$) to give 1700B (500 mg, 75%).

Part B:

Compound 1700B (500 mg, 2.44 mmol) was added to DMPU (20 mL) and heated with a heat gun until all the material was dissolved. The mixture was then cooled down to room temperature. Sodium t-butoxide (281 mg, 2.92 mmol) was added and the mixture was stirred at room temperature for 5 hours. Chloromethylpivalate (0.42 mL, 2.92 mmol) was added dropwise and the mixture was stirred at room temperature for 3 hours. The reaction mixture was poured into 150 ml water. The resulting solid was then filtered and collected to give 1700C (560 mg, 72%).

Part C:

Compound 1700C (560 mg, 1.75 mmol) was dissolved in methylene chloride (10 mL) and cooled in an ice bath. Bromotrimethylsilane (0.3 mL, 2.08 mmol) was added dropwise and the mixture was stirred in the ice bath for 30 minutes followed by 2 hours at room temperature. The reaction mixture was concentrated and re-dissolved in methylene chloride (2 mL). Hexanes (8 mL) was added and the solids were filtered to provide the desired product 1700D (360 mg, 70%).

Part D:

Compound 10 (294 mg, 1.21 mmol) and compound 1700D (360 mg, 1.21 mmol) were dissolved in THF (15 mL) and cooled to −78° C. A 1M solution of LiHMDS (2.6 mL, 2.6 mmol) was added dropwise and the reaction mixture was stirred for 3 hours. Saturated ammonium chloride solution was added slowly and the reaction was allowed to warm to room temperature. The aqueous layer was extracted with ethyl acetate. The combined organic layers were washed with water, brine, dried over sodium sulfate, and concentrated. Purification by column chromatography (SiO$_2$, 33% ethyl acetate/hexanes to 50% ethyl acetate/hexanes) afforded the desired product 1700E (360 mg, 65%).

Part E:

Compound 1700E (360 mg, 0.927 mmol) in 7 M ammonia in methanol (10 mL) was heated to 85° C. in a pressure bottle overnight. TLC indicated that the reaction was not complete. Therefore, the solvent was evaporated and the residue was dissolved in 7M ammonia in methanol (10 mL) and heated to 85° C. in a pressure bottle for overnight. The reaction mixture was concentrated. The residue was washed with ether and filtered. The solid was collected to afford 1700F (150 mg, 50%) which was used in the next step without further purification.

Part F:

Compound 1700F (36 mg, 0.10 mmol), compound 1700G (33 mg, 0.14 mmol), Pd(PPh$_3$)$_2$Cl$_2$ (5.9 mg, 0.084 mmol), CuI (3.0 mg, 0.016 mmol), and diisopropylamine (0.1 mL) were dissolved in DMF (1 mL) and stirred at 80° C. overnight. The reaction mixture was purified by Gilson reverse phase chromatography to afford 1700 (10.8 mg, 20%). HPLC-MS $t_R$=2.65 min (UV$_{254\ nm}$); mass calculated for formula C$_{25}$H$_{17}$FN$_6$O$_5$, 500.12, observed LCMS m/z 501.3 (M+H).

Example 14

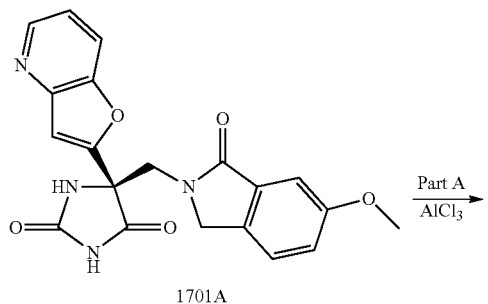
1701A

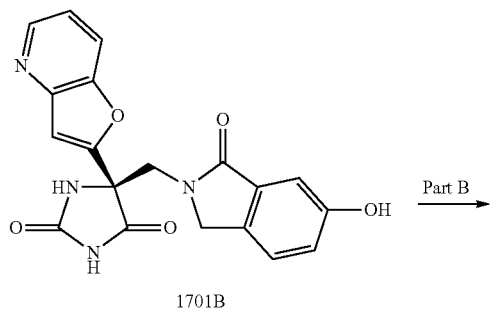
1701B

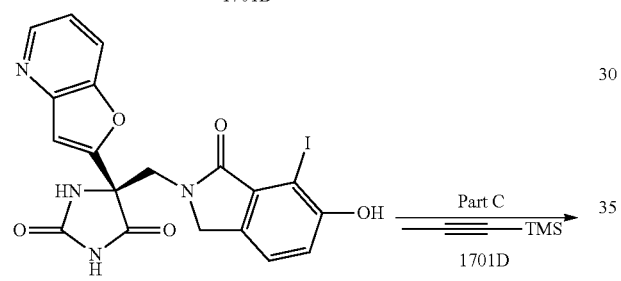
1701C

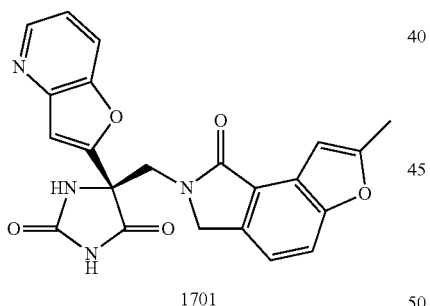
1701

Part A:

Compound 1701A (1.8 g, 4.59 mmol) and AlCl$_3$ (1.8 g, 13.50 mmol) were stirred in methylene chloride in a sealed tube at 75° C. overnight. After cooling, the reaction mixture was taken up in ethyl acetate and extracted with water. The aquous layer was extracted with ethyl acetate 3 times. The combined organic layers were dried with Na$_2$SO$_4$ and then concentrated to dryness. The crude material which was 1701B (1.6 g, 92%) was used without further purification.

Part B:

Compound 1701B (300 mg, 0.79 mmol) was dissolved in ammonium hydroxide (9 mL) and stirred in ice bath to make mixture 1. Iodine (180 mg, 0.63 mmol) and KI (421 mg, 2.54 mmol) were dissolved in H$_2$O (3 mL) and this mixture was added dropwise to mixture 1. After addition, the ice bath was removed and the reaction mixture was stirred at room temperature for 2 h. After the reaction was terminated, the solvent was removed. The crude material was purified with ISCO reverse phase column and eluted with actonitrile-water to give 1701C (100 mg, 25%).

Part C:

A mixture of 1701C (80 mg, 0.16 mmol), 1701D (53 mg, 0.47 mmol), copper iodide (5 mg, 0.028 mmol), Pd(PPh$_3$)$_2$Cl$_2$ (5 mg, 0.008 mmol) and diisopropylamine (0.120 mL. 0.86 mmol) in DMF (1 mL) was stirred at 85° C. overnight. The reaction mixture was purified by Gilson reverse phase HPLC using a 0.1% formic acid in the acetonitrile-water mobile phase. The isolated fractions were concentrated to afford 1701 (13 mg, 20%) as a light yellow solid. HPLC-MS $t_R$=2.61 min (UV$_{254\ nm}$); mass calculated for formula C$_{22}$H$_{16}$N$_4$O$_5$ 416.11, observed LCMS m/z 417.2 (M+H).

Example 15

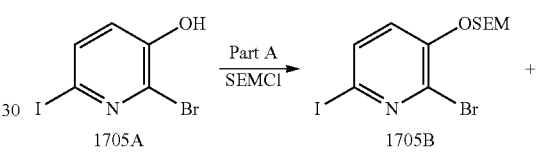
1705A    1705B

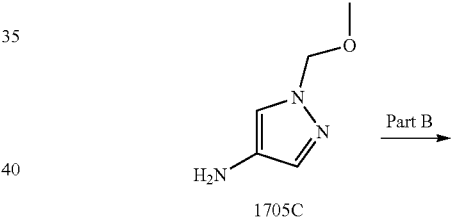
1705C

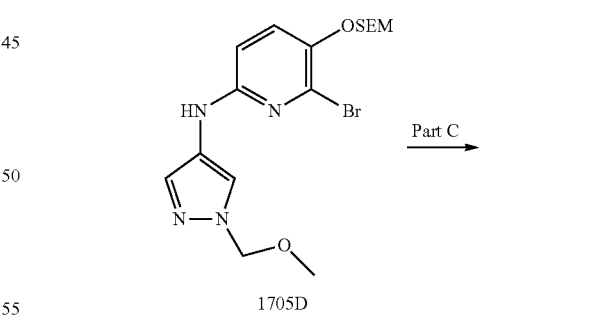
1705D 1705E    14

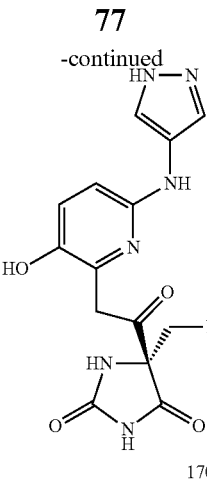

1705

Part A:

A mixture of compound 1705A (6.2 g, 20.67 mmol) which was made according to the literature procedures (*Synthesis,* 1990, 497-498) and triethylamine (8.7 mL, 62.41 mmol) was stirred in methylene chloride (100 mL) at room temperature. SEMCl (4.4 mL, 24.94 mmol) was added dropwise and the reaction mixture was stirred at room temperature overnight. The reaction mixture was extracted with $H_2O$ (100 mL) and layers were separated. The organic layer was dried and concentrated to dryness. The crude material was purified by silica gel chromatography (Hexane/EtOAc: 4:1) to afford compound 1705B (5 g, 56%).

Part B:

A mixture of 1705B (500 mg, 1.16 mmol), 1705C (148 mg. 1.16 mmol), $Pd(OAc)_2$ (23 mg, 0.10 mmol), Xantphos (40 mg, 0.069 mmol) and sodium t-butoxide (138 mg, 1.43 mmol) in dioxane (3 mL) was stirred in a sealed tube at 100° C. overnight. After cooling, the reaction mixture was diluted with ethyl acetate (100 mL) and $H_2O$ (100 mL). The layers were separated. The organic layer was dried with $Na_2SO_4$ and then concentrated to dryness. The crude material was purified by silica gel chromatography (Hexane/EtOAc:1:1) to afford compound 1705D (240 mg, 48%).

Part C:

Compound 1705D (240 gm, 0.56 mmol) was dissolved in methanol (10 mL) and HCl (20 mL, 4N in dioxane) was added and the reaction mixture was stirred at room temperature two and half days. The mass spectrum of the reaction mixture still showed the presence of starting material. Solvents were removed and HCl (50 mL, 6N in $H_2O$) and methanol (10 mL) were added and the mixture was stirred at room temperature overnight. Solvents were removed to afford compound 1705E (140 mg, 99%) which was used without further purification.

Part D:

A mixture of 1705E (72 mg, 0.28 mmol), compound 14 (93 mg, 0.31 mmol), copper iodide (5 mg, 0.028 mmol), $Pd(PPh_3)_2Cl_2$ (5 mg, 0.008 mmol) and diisopropylamine (0.40 mL, 2.85 mmol) in DMF (1 mL) was stirred at 85° C. overnight. The reaction mixture was purified by Gilson reverse phase HPLC using a 0.1% formic acid in the acetonitrile-water mobile phase. The fractions which contained 1705 were concentrated to a light yellow solid (24 mg, 17%). HPLC-MS $t_R$=2.38 min ($UV_{254\ nm}$); mass calculated for formula $C_{23}H_{21}N_7O_6$ 491.16, observed LCMS m/z 492.3 (M+H).

Example 16

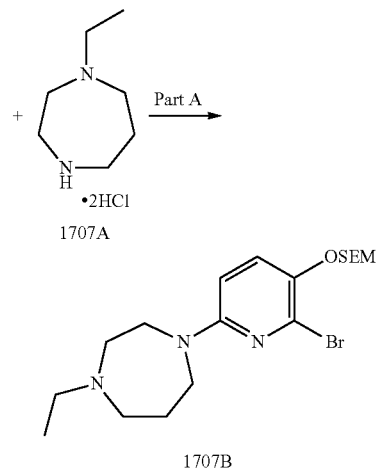

Part A:

A mixture of 1705B (813 mg, 1.89 mmol), 1707A (400 mg, 1.89 mmol), copper iodide (36 mg, 0.19 mmol), L-proline (44 mg, 0.38 mmol) and $K_2CO_3$ (0.8 g, 5.8 mmol) in DMSO (3 mL) was stirred at 70° C. overnight. After cooling, the reaction mixture was diluted with ethyl acetate (20 mL) and Brine (20 mL). The layers were separated. The organic layer was dried with $Na_2SO_4$ and then concentrated to dryness. The crude material was purified by silica gel chromatography (Hexane/EtOAc:9:1 to Hexane/EtOAc:3:1) to afford compound 1707B (360 mg, 44%).

Example 17

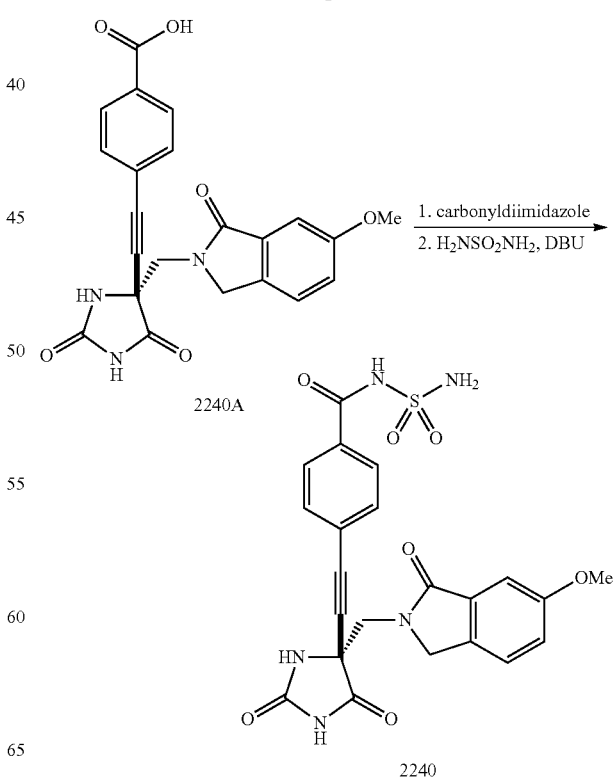

Compound 2240A and methods for its preparation are described in Lavey, B. J. et al. PCT Appl. WO2007084451 (A1). Solid carbonyldiimidazole (65 mg, 0.40 mmol) was added in one portion to a stirred solution of Compound 2240A (67 mg, 0.16 mmol) in THF (0.325 mL). The reaction was stirred for 1.5 h at reflux, then allowed to cool to rt. Solid sulfamide (31 mg, 0.32 mmol) and DBU (71 µL, 73 mg, 0.48 mmol) were added sequentially. The reaction mixture became turbid and was stirred at rt for 18 h. The reaction mixture was concentrated under reduced pressure to afford a crude solid product that was then purified by reverse-phase C18 chromatography (10-100% MeCN—H$_2$O gradient). The desired product, Compound 2240 was obtained as a white solid (47 mg, 60% yield).

Example 18

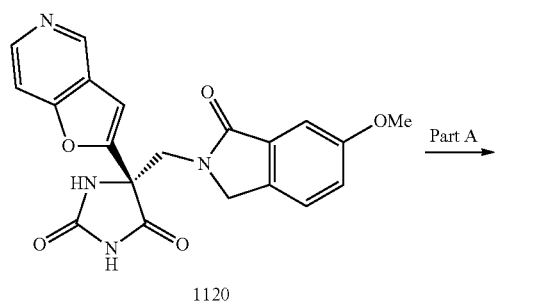

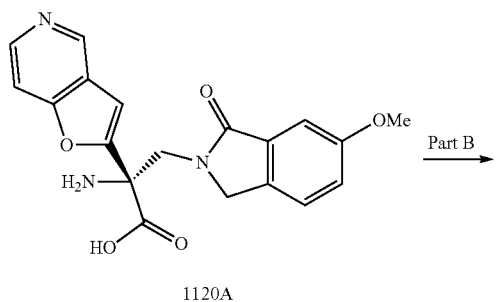

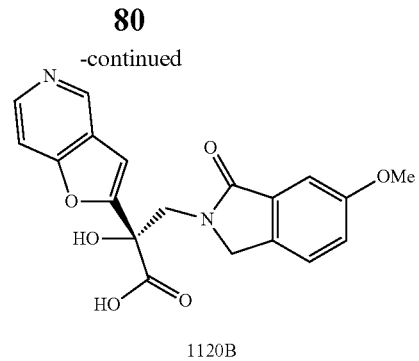

Part A

Compound 1120 was prepared as described in Yu, Wensheng et al Imidazolidinedione derivatives and their preparation, pharmaceutical compositions, and use for the treatment of inflammatory disorders. U.S. Patent Application Publication No. US 2007/0219218. Compound 1120 was converted to 1120A using the procedure of Hammarstrom, L. G. J.; Fu, Y.; Vail, S.; Hammer, R. P.; McLaughlin, L. Org. *Syntheses* 2005, 81, 213. LRMS calcd. 367.11 obsd 368.08.

Part B

Compound 1120A was converted to 1120B using the procedure of Foccella, A.; Bizzarro, F. and Exon, C. *Syn Comm* 1991, 21, 2165. The crude product was purified via reverse phase chromatography on a C-18 column using a 15%-80% CH$_3$CN/H$_2$O gradient with 0.1% formic acid added to each component of the mobile phase. The gradient was stopped temporarily at 35% CH$_3$CN while the main peak came off of the column to give 22 mg of impure product. This material was purified via reverse phase HPLC on a C-18 column using a 5%-50% CH$_3$CN/H$_2$O gradient with 0.1% formic acid added to each component of the mobile phase. Compound 1120B was obtained as a white solid. LCMS calcd. 368.1 obsd 369.2.

Example 19

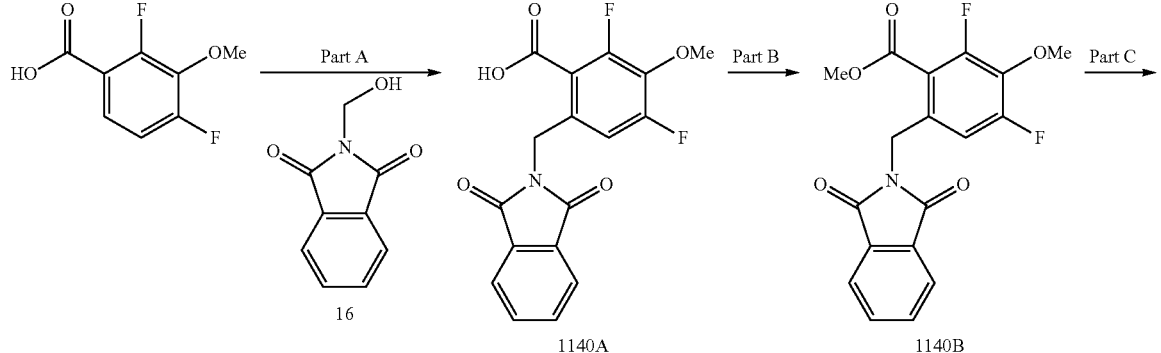

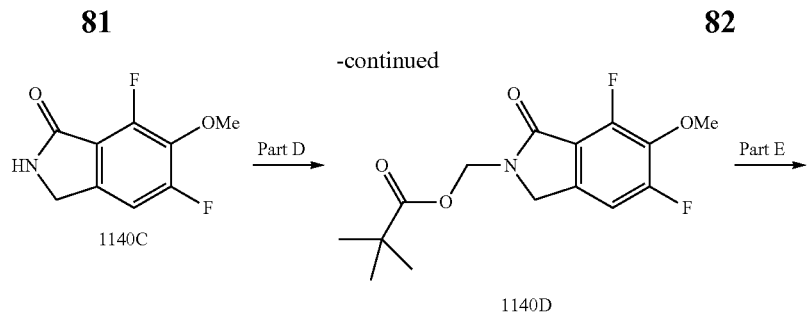

-continued

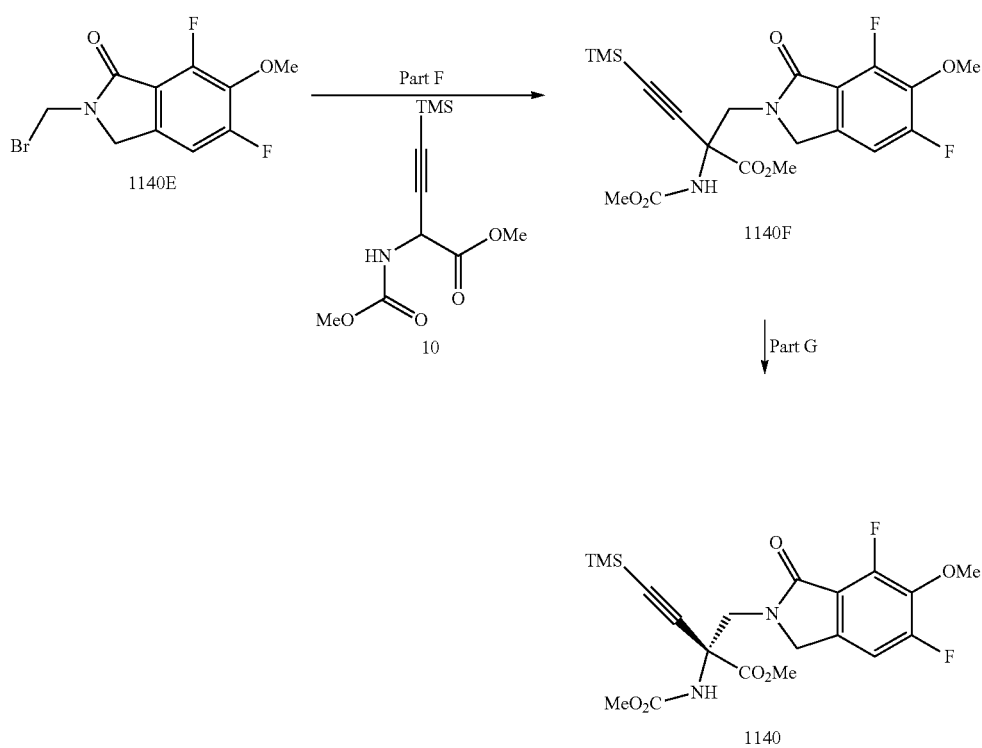

2,4-Difluoro-3-methoxy-benzoic acid was converted to compound 1140F using a sequence of reactions and a set of procedures similar to those described in Example 4.

Part A.

Compound 1140A: $^1$HNMR (CDCl$_3$) δ 7.94-7.86 (m, 2H), 7.82-7.75 (m, 2H), 6.96-6.87 (m, 1H), 5.11 (s, 2H), 4.02 (s, 3H).

Part B

Compound 1140B: $^1$HNMR (CDCl$_3$) 7.93-7.84 (m, 2H), 7.79-7.71 (m, 2H), 7.02-6.92 (m, 1H), 5.00 (s, 2H), 4.05-3.95 (m, 6H).

Part C

Compound 1140C: $^1$HNMR (DMSO) δ 8.65 (s, 1H), 7.44-7.34 (m, 1H), 4.33 (s, 2H), 3.93 (s, 3H).

Part D

Compound 1140D: $^1$HNMR (CDCl$_3$) δ 7.09-6.93 (m, 1H), 5.61 (s, 2H), 4.51 (s, 2H), 4.04 (s, 3H), 1.22 (s, 9H).

Part E

Compound 1140E: $^1$HNMR (CD$_3$OD) δ 7.39-7.15 (m, 1H), 4.56 (s, 2H), 4.02 (s, 3H).

Part F

Compound 1140F: $^1$HNMR (CDCl$_3$) δ 7.00-6.94 (m, 1H), 6.51 (s, 1H), 4.79-4.68 (m, 1H), 4.46-4.30 (m, 2H), 4.04 (s, 3H), 3.88 (s, 3H), 0.18 (s, 9H).

Part G

Compound 1140F was separated into its enantiomers via chiral HPLC. Compound 1140F (0.5 gram) was dissolved in 5 mL of 4:6 CHCl$_3$:MeOH and injected onto a preparative ChiralCel OD HPLC column from Chiral Technologies. The detector was set at 237 nm. The mobile phase was 95:5 hexanes:absolute ethanol at a flow rate of 50 mL/min.

Example 20

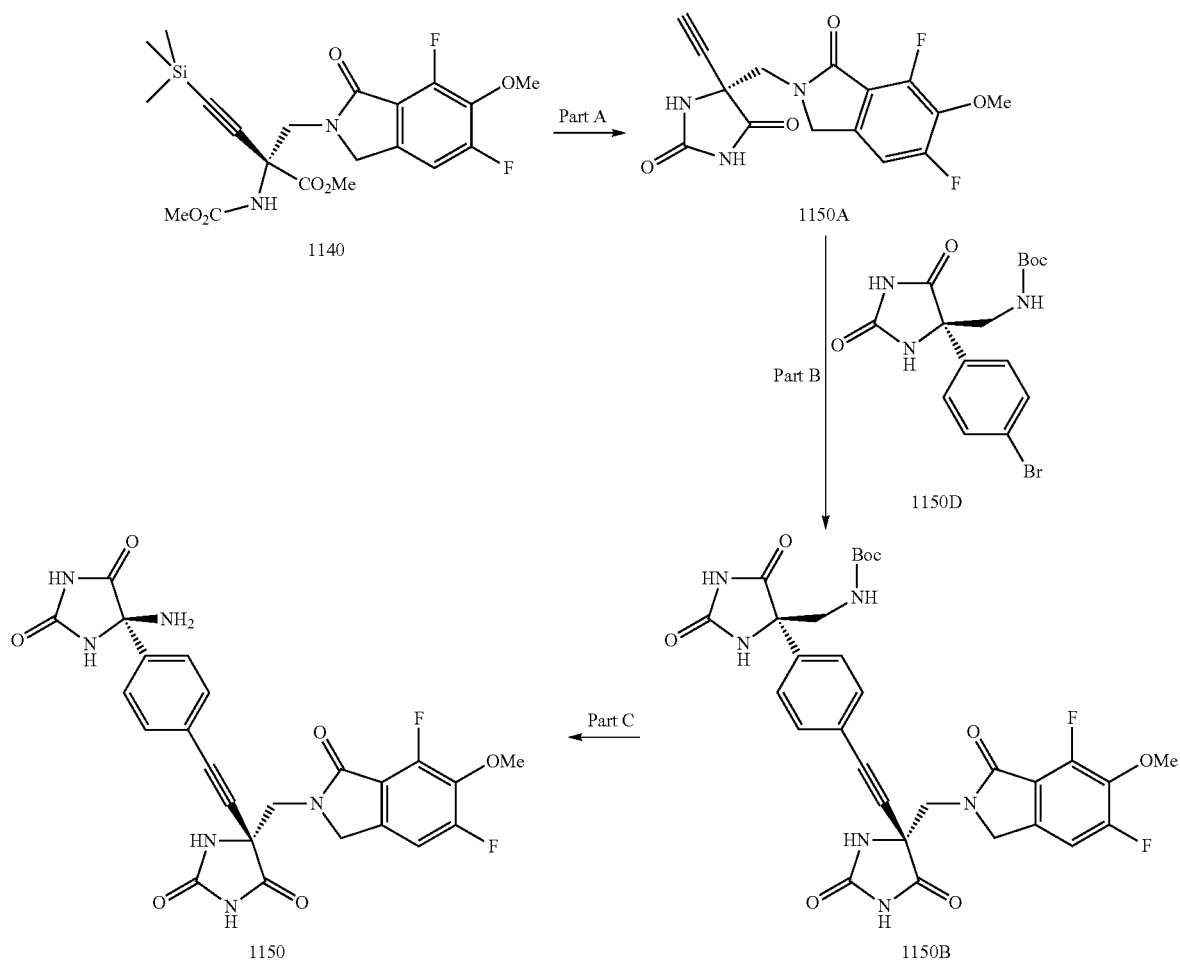

Part A.

Compound 1140 (0.6 g, 1.32 mmol), was added to a pressure tube. Methanolic ammonia (20 mL, Aldrich 7 N) was added. The tube was capped and the reaction mixture was heated at 80° C. overnight. The reaction mixture was concentrated to dryness to give compound 1150A (0.36 g, 82% yield). $^1$HNMR (CD$_3$OD) δ 7.28-7.21 (m, 1H), 4.73-4.51 (m, 2H), 4.08 (s, 3H), 3.62 (s, 1H).

Part B

Compound 1150A (50 mg, 0.15 mg) and compound 1150D were converted to 1150B using a Sonogashira procedure similar to that described in Example 7. $^1$HNMR (CD$_3$OD) δ 7.66-7.58 (m, 2H), 7.56-7.45 (m, 2H), 7.30-7.20 (m, 1H), 4.80-4.69 (m, 1H), 4.65-4.56 (m, 1H), 4.18 (s, 2H), 4.00 (s, 3H), 3.82-3.75 (m, 1H), 3.61-3.52 (m, 1H), 1.42 (s, 9H).

Part C

Compound 1150B (41 mg, 0.064 mmol) was dissolved in 2 mL of MeOH. A solution of 4N HCl in dioxane was added (3 mL). The reaction mixture was stirred for 4 h at it then concentrated to dryness. The product was dissolved in a minimum amount of MeOH. EtOAc was added, causing a precipitate to form. The mixture was placed in a centrifuge, to spin down the precipitate. The solution was removed via pipet. The solid was washed with EtOAc then dried under vacuum to give 30 mg of compound 1150. LCMS calcd 538.14 obsd 539.3.

Example 21

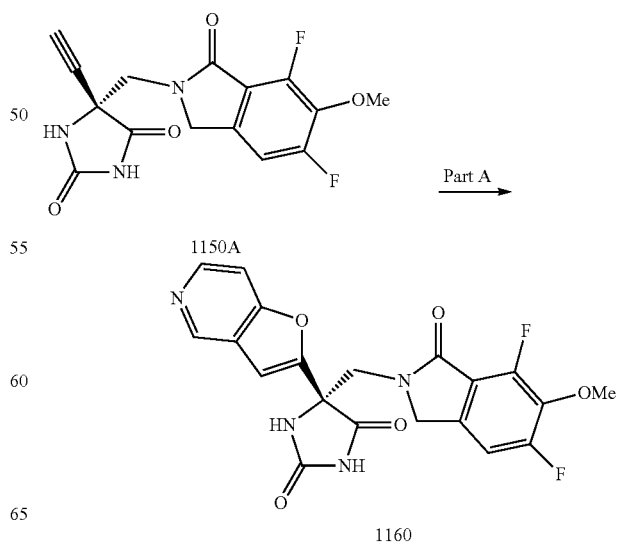

Part A

Compound 1150A was converted to 1160 using a procedure similar to that described in Example 7. LRMS calcd 428.09 obsd 429.2.

Example 22

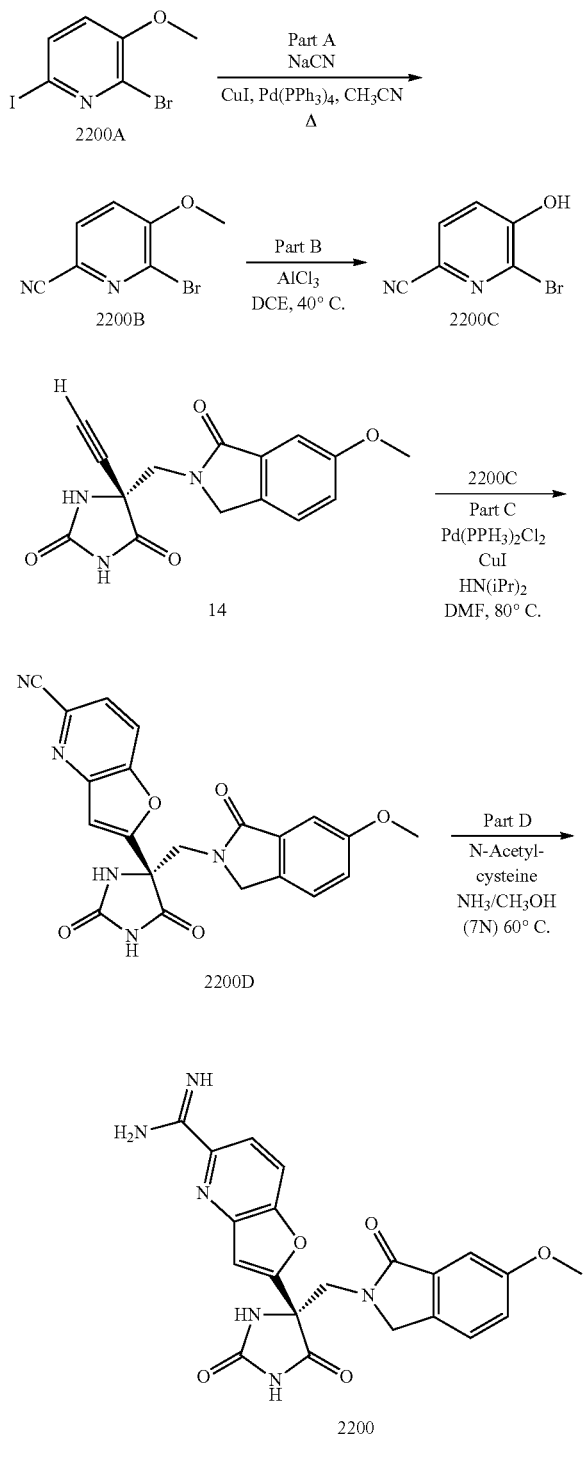

Part A:

A mixture of 2-Bromo-5-iodo-3-methoxy pyridine 2200A (0.95 g, 3.0 mmol), NaCN (0.176 g, 3.6 mmol), Palladium tetrakis triphenylphospine (0.2 g, 1.8 mmol), CuI (0.07 g, 0.4 mmol) and acetonitrile (10 mL) was charged into a sealed tube and purged with nitrogen (3×). The reaction was heated at 80° C. for 10 h. After cooling to room temperature the reaction was diluted with EtOAc (100 ml), washed with water (2×50 ml) and brine (1×50 mL), dried ($Na_2SO_4$), filtered, and concentrated to give a crude product which was purified by flash column chromatography (ISCO CombiFlash Rf, $SiO_2$, 12 g cartridge (hexanes to 35% EtOAc/hexanes) to yield compound 2200B (0.25 g, 30%).

Part B:

Compound 2200B (0.2 g, 0.93 mmol) was dissolved in dichloroethane (DCE) (5 mL) and aluminum chloride (0.1 g, 0.85 mmol) was added. The reaction mixture was stirred at 40° C. for 10 hours. The reaction was cooled and diluted with EtOAc (50 mL) and washed 2×25 mL water, and brine (1×25 mL) and then dried over sodium sulfate, and concentrated to provide a crude which was purified by flash column chromatography (ISCO CombiFlash Rf, $SiO_2$, 4 g cartridge (Hexanes to 25% EtOAc/hexanes) to yield compound 2200C (0.11 g, 60%).

Part C:

A mixture of 14 (0.11 g, 0.3 mmol), 2200C (0.12 g, 0.3 mmol), copper iodide (0.008 g, 0.045 mmol), $Pd(PPh_3)_2Cl_2$ (0.005 g, 0.008 mmol) and diisopropylethylamine (0.047 mL, 0.33 mmol) in DMF (3 mL) was charged into a sealed tube and purged with nitrogen (3×). The mixture was heated at 80° C. for 12 h. The reaction mixture was filtered and the filtrate was concentrated and purified by reverse phase chromatography using a 0.1% trifluoracetic acid in the aqueous mobile phase (100% water to 50% acetonotrile/water) to provide 2200D (0.09 g, 45%).

Part D:

A mixture of 2200D (0.02 g, 0.047 mmol), N-acetylcysteine[1] (0.02 g, 0.12 mmol), 7N $NH_3/CH_3OH$ (5 mL) was charged into a sealed tube and heated at 60° C. for 24 h. The reaction was cooled and the solvent was removed and the product was isolated by reverse phase chromatography using a 0.1% trifluoracetic acid in the aqueous mobile phase (100% water to 50% acetonitrile/water) to provide 2200 (0.017 g, 85%). LC-MS* $t_R$=1.87 min; observed LCMS m/z 435.2 (M+H).

Reference:

1. Udo E. W. Lange, Bernd Schäfer, Dorit Baucke, Ernst Buschmann, Helmut Mack. *Tetrahedron letters* 40, 7067, 1999.

The following compounds were made from 2200D using the procedure described in part D, using corresponding amines (hydroxylamine, N-ethylpiperazine, N-methyl homopiperazine.)

| ID | STRUCTURE | (M + 1)+ | LC MS* $t_R$ |
|---|---|---|---|
| 1500 | 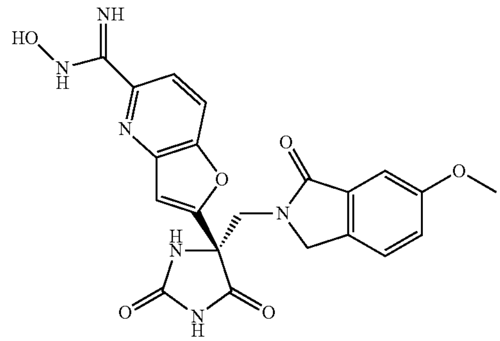 [SMILES: COc1ccc2c(c1)C(=O)N(C[C@@]1(c3cc4nc(C(=N)NO)ccc4o3)NC(=O)NC1=O)C2] | 451.2 | 1.79 |
| 1501 | 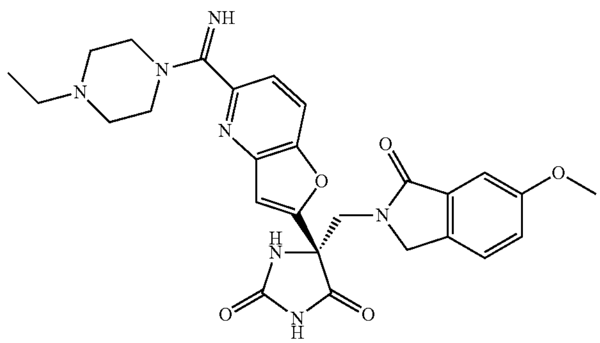 [SMILES: CCN1CCN(C(=N)c2ccc3oc([C@]4(CN5Cc6ccc(OC)cc6C5=O)NC(=O)NC4=O)cc3n2)CC1] | 533.3 | 1.89 |
| 1502 | 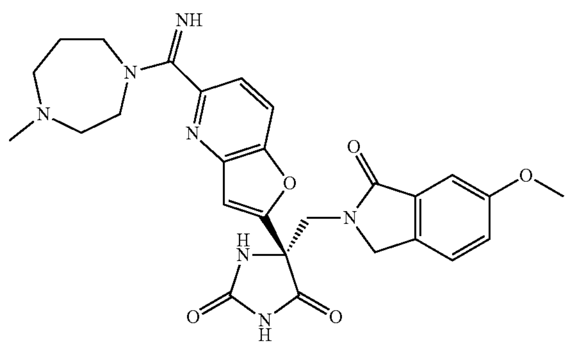 | 533.3 | 2.01 |
Example 23
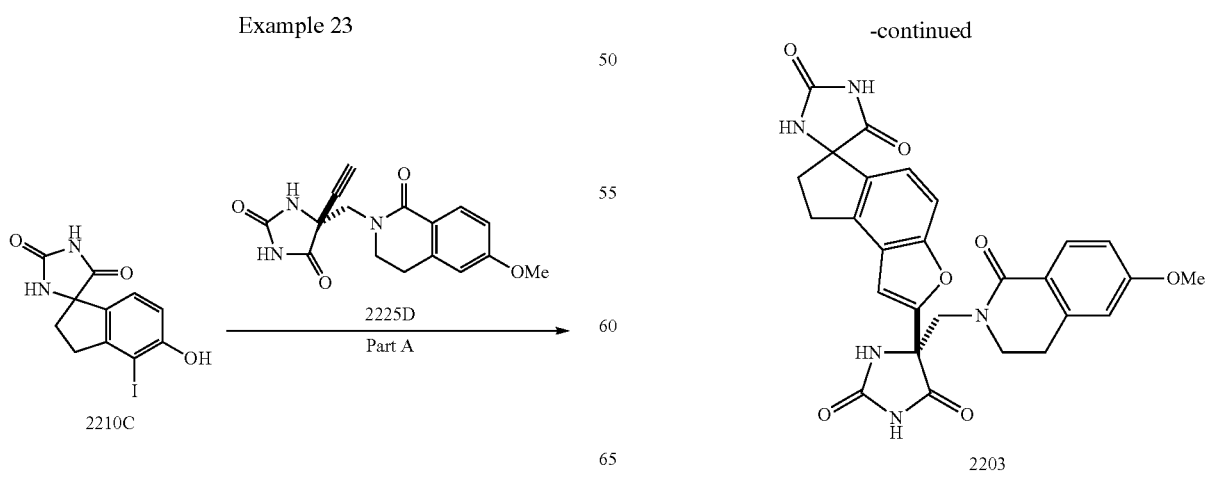

Part A:

Compound 2210C was prepared as described in Example 29. Compound 2225D was prepared using the method described previously in Lavey, B. J. WO 2007/084451, Example 1087. Compounds 2210C and 2225D were combined according to the procedure of Example 6 to afford Compound 2203. HPLC-MS $t_R$=2.60 min (UV$_{254\,nm}$); mass calculated for formula $C_{27}H_{23}N_5O_7$ 529.2, observed LCMS m/z 530.3 $[M+H]^+$.

Example 24

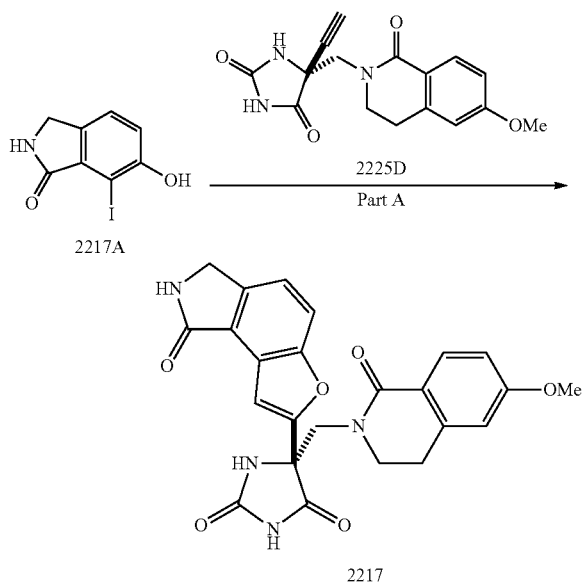

2217A

2217

Part A:

Compound 2217A was prepared as described in Example 14. Compound 2225D was described previously in Lavey, B. J. WO 2007/084451. Example 1087. Compounds 2217A and 2225D were combined according to the procedure of Example 6 to afford Compound 2217. HPLC-MS $t_R$=2.56 min (UV$_{254\,nm}$); mass calculated for formula $C_{24}H_{20}N_4O_6$ 460.1, observed LCMS m/z 461.3 $[M+H]^+$.

Example 25

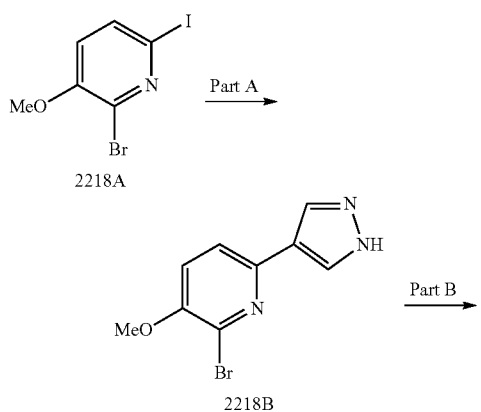

2218A

2218B

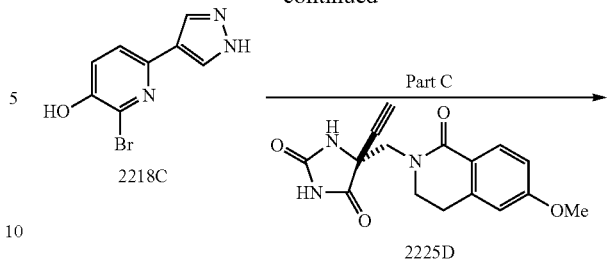

2218C

2225D

2218

Part A:

Compound 2218A was prepared according to the method described in Chapman, G. M.; Stanforth, S. P; Tarbit, B.; Watson, M. D. *J. Chem. Soc., Perkin Trans.* 1 2002, 581-582. A microwave tube containing Compound 2218A (1.0 g, 3.2 mmol), pyrazole-3-boronic acid (426 mg, 3.82 mmol) and (Ph3P)$_4$Pd (294 mg, 0.250 mmol) was sealed, evacuated, and placed under nitrogen atmosphere. Acetonitrile (16 mL) and 1 M aq. potassium carbonate solution (16 mL) were added and the reaction mixture was stirred at 100° C. for 2 d. The aqueous layer was separated and extracted with EtOAc (3×25 mL). The combined organic layers were washed with brine (~50 mL), dried over anhydrous MgSO$_4$, filtered, and concentrated under reduced pressure. From the complex reaction mixture, repeated sgc (10-70% EtOAc-hexanes gradient) afforded 80 mg (10% isolated yield) of the desired Compound 2218B.

Part B:

A solution of Compound 2218B (96 mg, 0.38 mmol) in DCE (5 mL) was treated with anhydrous aluminum chloride (126 mg, 0.94 mmol) in a pressure vessel. The vessel was capped and the reaction mixture was heated at reflux for 18 h. The reaction mixture was allowed to cool to rt and was concentrated under reduced pressure. The resulting residue was partitioned in EtOAc (~100 mL) and water (~100 mL). The aqueous layer was separated and extracted further with EtOAc (3×~25 mL). The combined organic phases were washed with brine (50 mL), dried over anhydrous MgSO$_4$, filtered, and concentrated under reduced pressure to afford 104 mg of crude product as a yellow solid. Mass calculated for formula $C_8H_6{}^{81}BrN_3O$ 241.0, observed m/z 241.9 $[M+H]^+$.

Part C:

Compound 2225D was prepared according to the method previously reported in Lavey, B. J. WO 2007/084451, Example 1087. A flame-dried microwave tube containing Compound 2225D (60 mg, 0.19 mmol), Compound 2218C (58.4 mg, 0.21 mmol), $(Ph_3P)_2PdCl_2$ (13 mg, 0.019 mmol), copper(I) iodide (3.6 mg, 0.019 mmol) and a magnetic stir bar was sealed, evacuated and placed under nitrogen atmosphere. Dry, degassed DMF (0.9 mL) and diisopropylamine (0.070 mL, 49 mg, 0.38 mmol) were added. The reaction mixture was stirred at 80° C., then allowed to cool to rt, and was filtered. The filtrate was subjected to reverse-phase C18 chromatography (10-90% MeCN-water gradient) to afford 41 mg (46% yield) of Compound 2218B. HPLC-MS $t_R$=2.22 min (UV$_{254\ nm}$); mass calculated for formula $C_{24}H_{20}N_6O_5$ 472.2, observed LCMS m/z 473.3 [M+H]$^+$.

Example 26

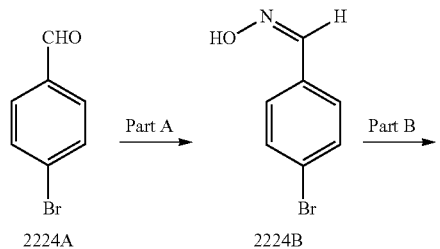

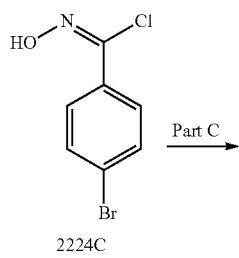

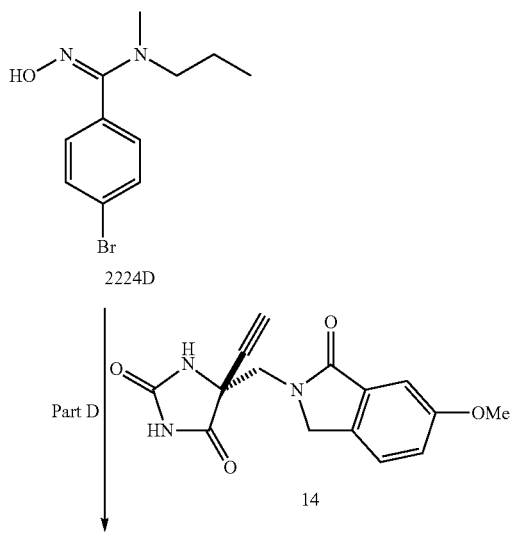

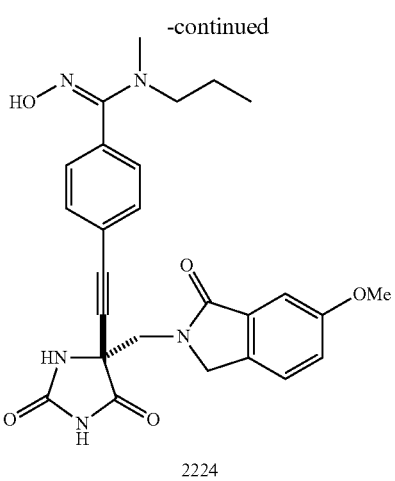

2224

Part A

A mixture of p-bromobenzaldehyde (Compound 2224A; 5.00 g, 27.0 mmol), hydroxylamine hydrochloride (3.73 g, 54.1 mmol) and anhydrous sodium acetate (4.43 g, 54.1 mmol) in absolute ethanol (100 mL) was stirred at reflux (80° C. external oil bath temperature) in a pressure vessel for 24 h. The solvent was removed under reduced pressure. The remaining solid was dissolved in Et$_2$O (~250 mL) and the resulting solution was washed sequentially with water (2×~100 mL) and brine (~100 mL). The organic layer was dried over anhydrous MgSO$_4$, filtered and concentrated under reduced pressure to afford Compound 2224B as a white solid (5.23 g, 97% yield).

Part B

Solid N-chlorosuccinimide (0.722 g, 5.39 mmol) was added to a stirred solution of oxime (Compound 2224B; 1.072 g, 5.39 mmol) in dry DMF (15 mL). The reaction mixture was stirred at rt for 18 h. The reaction mixture was diluted with Et$_2$O (150 mL) and was washed sequentially with water (3×50 mL) and brine (~50 mL). The organic layer was dried over anhydrous MgSO$_4$, filtered and concentrated under reduced pressure to give a pale yellow solid. Purification of the solid by sgc (40 g silica gel cartridge; 5-25% EtOAc-hexanes gradient) gave 973 mg (77% yield) of the desired product, Compound 2224C, as a white solid.

Part C

Methyl-n-propylamine (151 mg, 2.56 mmol) was added to a solution of oximyl chloride (Compound 2224C, 300 mg, 1.28 mmol) in CH$_2$Cl$_2$ (8 mL) and the resulting mixture was stirred overnight at rt. Evaporation of the solvent gave a residue that was purified by sgc (1-10% MeOH/NH$_3$ in CH$_2$Cl$_2$ gradient) to afford 215 mg (62% yield) of the desired product, Compound 2224D.

Part D

Aryl bromide 2224D was converted into Compound 2224 following the procedure given in Example 6. HPLC-MS $t_R$=2.28 min (UV$_{254\ nm}$); mass calculated for formula $C_{26}H_{27}N_5O_5$ 489.2, observed LCMS m/z 490.3 [M+H]$^+$.

Using the same procedure as described in this Example, the following compounds could be synthesized: Compounds 2227, 2228, 2229, 2231, and 2234.

Compound 2227: HPLC-MS $t_R$=2.83 min (UV$_{254\ nm}$); mass calculated for formula $C_{22}H_{21}N_5O_5S$ 467.1, observed LCMS m/z 468.3 [M+H]$^+$.

Compound 2228: HPLC-MS $t_R$=1.84 min (UV$_{254\ nm}$); mass calculated for formula $C_{27}H_{30}N_6O_5$ 518.6, observed LCMS m/z 519.3 [M+H]$^+$.

Compound 2229: HPLC-MS $t_R$=1.96 min (UV$_{254\ nm}$); mass calculated for formula $C_{29}H_{34}N_6O_5$ 546.3, observed LCMS m/z 547.3 [M+H]$^+$.

Compound 2231: HPLC-MS $t_R$=1.96 min (UV$_{254\ nm}$); mass calculated for formula $C_{24}H_{23}N_5O_5$ 461.2, observed LCMS m/z 462.3 [M+H]$^+$.

Compound 2234: HPLC-MS $t_R$=2.28 min (UV$_{254\ nm}$); mass calculated for formula $C_{26}H_{27}N_5O_5$ 489.2, observed LCMS m/z 490.3 [M+H]$^+$.

Example 27

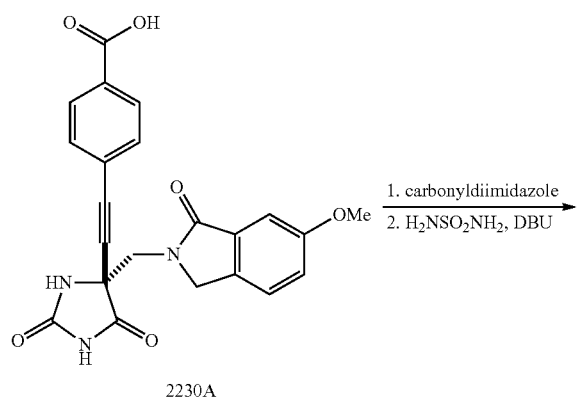

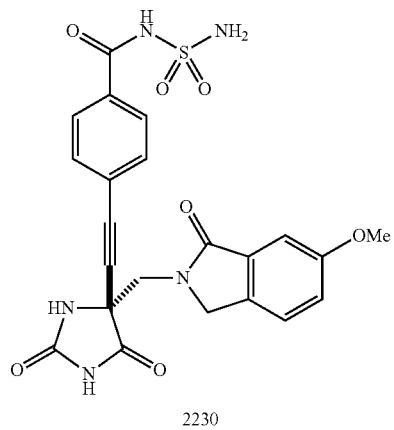

Compound 2230A and methods for its preparation are described in Lavey, B. J. et al. PCT Appl. WO2007084451 (A1). Solid carbonyldiimidazole (65 mg, 0.40 mmol) was added in one portion to a stirred solution of Compound 2230A (67 mg, 0.16 mmol) in THF (0.325 mL). The reaction was stirred for 1.5 h at reflux, then allowed to cool to it Solid sulfamide (31 mg, 0.32 mmol) and DBU (71 µL, 73 mg, 0.48 mmol) were added sequentially. The reaction mixture became turbid and was stirred at rt for 18 h. The reaction mixture was concentrated under reduced pressure to afford a crude solid product that was then purified by reverse-phase C18 chromatography (10-100% MeCN—H$_2$O gradient). The desired product, Compound 2230 was obtained as a white solid (47 mg, 60% yield). HPLC-MS $t_R$=2.69 min (UV$_{254\ nm}$); mass calculated for formula $C_{22}H_{19}N_5O_7S$ 497.1, observed LCMS m/z 498.3 [M+H]$^+$.

Example 28

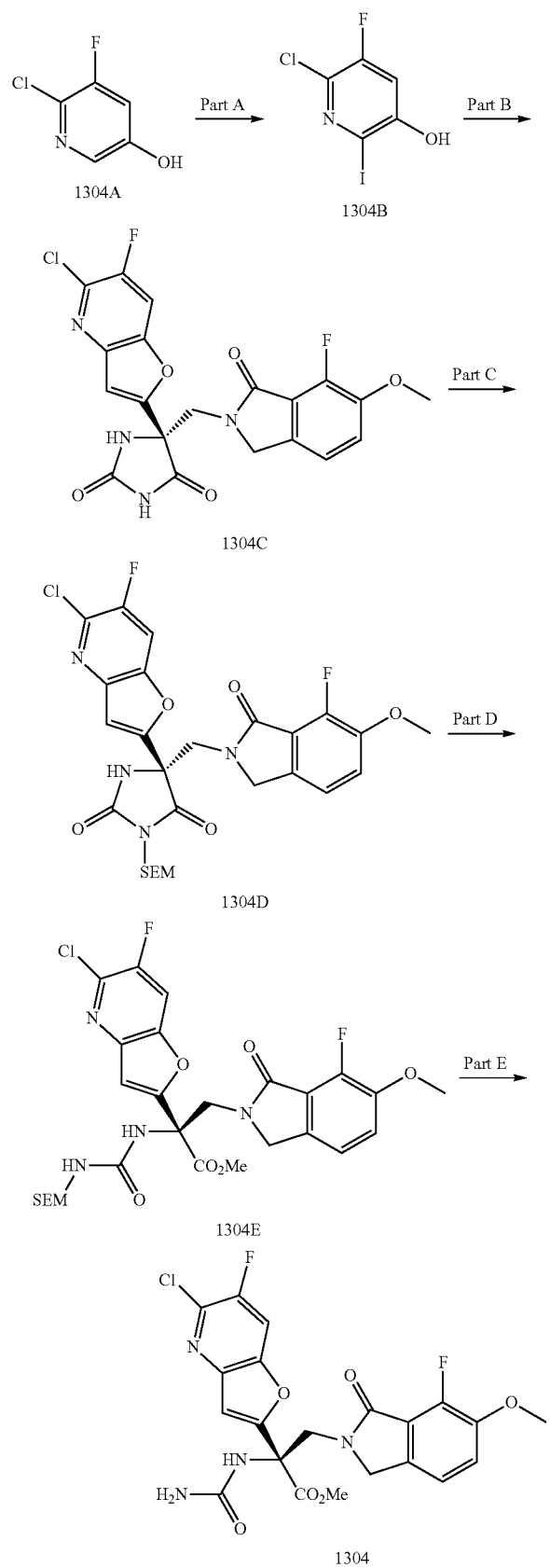

Part A

Compound 1304B was prepared by the same method described in Part B of Example 29.

Part B

Compound 1304C was prepared by the same method described in Example 6.

Part C

Compound 1304C (380 mg, 0.82 mmol) was dissolved in DMF (5 mL). DIPEA (0.28 mL, 1.64 mmol) and SEMCl (0.173 mL, 0.985 mmol) were added. The solution was stirred at RT for overnight. DMF was removed by rotary evaporator. The product was purified by sgc (EtOAc/Hexane: 20% to 100%) to give compound 1304D (441 mg, 90.7%).

Part D

To a 5 mL flask was added compound 13040 (65 mg, 0.11 mmol), 2-amino-5-(4,4,5,5-tetramethyl-1,3,2-dioxaborolan-2-yl)pyridine (35 mg, 0.16 mmol), Pd(dppf)$_2$Cl$_2$ (5 mg). The flask was subjected to vacuum and flushed with N$_2$ three times. K$_2$CO$_3$ (1M, 0.5 mL, 0.5 mmol) and CH$_3$CN were added. The solution was stirred at 80° C. overnight. After the flask had cooled, water and EtOAc were added. The organic layer was separated, washed with brine, dried over Na$_2$SO$_4$, and concentrated. The product was purified by SiO$_2$ chromatography (MeOH/DCM: 1% to 5%) to give compound 1304E.

Part E

Compound 1304E obtained in Part D was dissolved in MeOH (2 mL) in a 15 mL pressure tube. HCl (4M in dioxane, 2 mL) was added. The tube was capped and stirred at 90° C. for overnight. After cooling down, the solvent was removed and residue was dissolved in MeOH (3 ml) and DIPEA (0.5 mL) was added. The solution was stirred at RT for three hours. The solvent was removed and the product was purified by C18 chromatography (CH$_3$CN/H$_2$O, 5% to 90%, with 0.1% HCO$_2$H) to give compound 1304 (23.5 mg, 43.2%).

Example 29

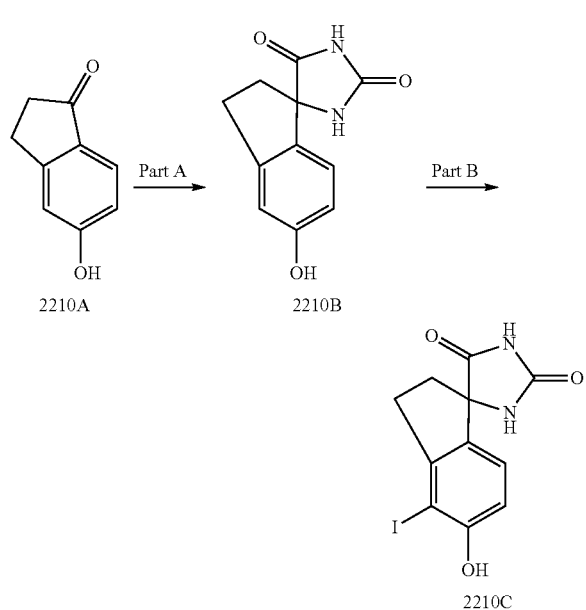

Part A

Compound 2210A (4.81 g, 32.5 mmol) was suspended in H$_2$O (30 mL) in a 350 mL pressure bottle. KCN (2.11 g, 32.5 mmol), (NH$_4$)$_2$CO$_3$ (12.5 g, 129.9 mmol), and NH$_3$/MeOH (7N, 30 mL) were added. The pressure bottle was capped and stirred at 80° C. for 2 days. After cooling down, water (30 mL) was added. The solid was collected by filtration, washed with water, and dried under vacuum to give compound 2210B (2.83 g, 40.0%)

Part B

Compound 2210B (600 mg, 2.75 mmol) was dissolved in NH$_3$—H$_2$O (37%, 40 mL). Heating may be needed to make a clear solution. A solution of I$_2$ (628 mg, 2.47 mmol) and KI (1.64 g, 9.88 mmol) in water (5 mL) was added dropwise. The solution was stirred at 25° C. for 1 hour. The solution was concentrated to half of its original volume, adjusting the pH to 2~4 with HCl (2N). The solid was collected by filtration, washed with water, dried under vacuum for overnight to give compound 2210C (805 mg, 85.1%)

Compounds 2210, 2211, 2214, 2216, and 2223 were prepared by the methods described in Example 29 and Example 6.

Example 30

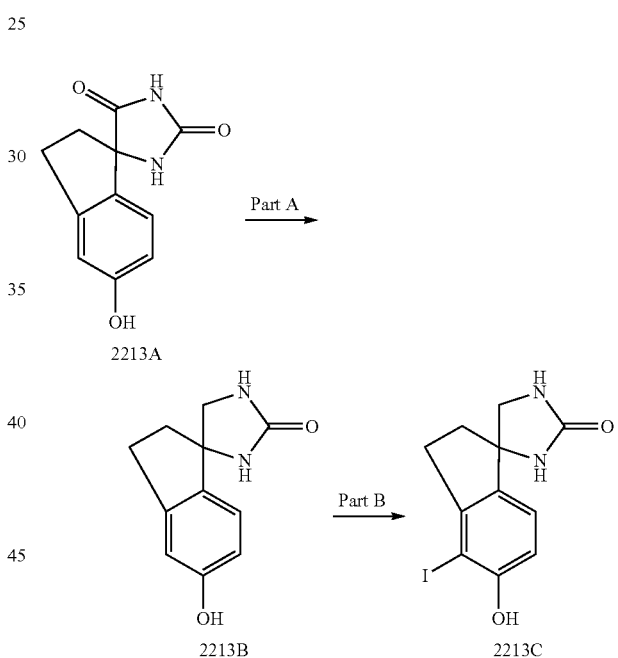

Part A

Compound 2213A (800 mg, 3.67 mmol) was suspended in anhydrous THF (40 mL) and cooled to 0° C. Red-Al (3.2 M, 9.2 mL, 29.4 mmol) was added dropwise. After the addition was completed, the solution was heated to 85° C. for 2 hours. It was then cooled to 0° C. and quenched with water. Organic solvent was removed by rotary evaporator. NaOH (1N) was added to adjust the pH to about 7. EtOAc was added and the organic layer was separated. The aqueous layer was extracted with EtOAc twice. The EtOAc layers were combined and concentrated. The product was purified by SiO$_2$ chromatography to give compound 2213C (539.5 mg, 72.1%).

Part B

Compound 2213C was prepared by the same method as described in part B of example 29.

Compounds 2213 and 2215 were prepared by the methods described in Example 30 and Example 6.

Example 31

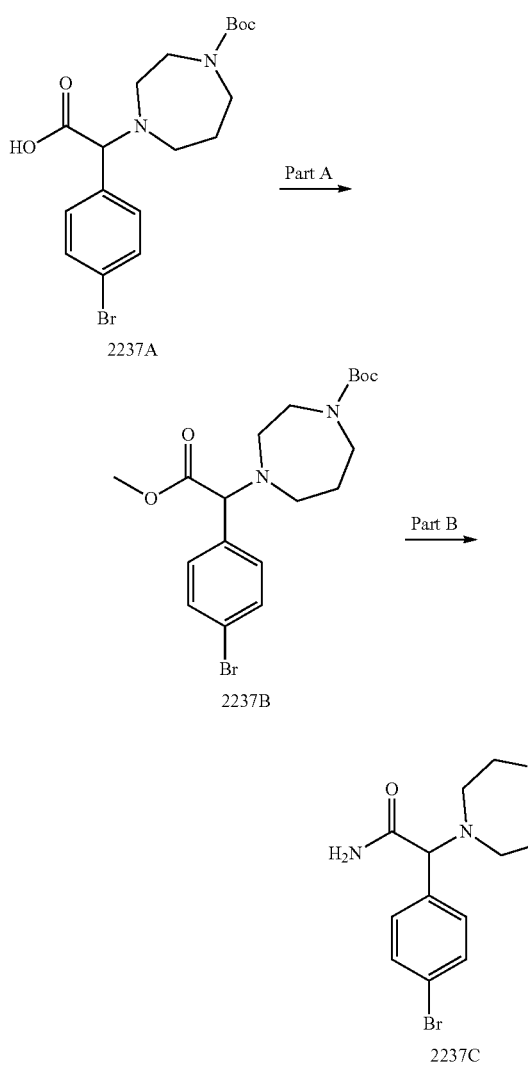

Part A

Compound 2237A (300 mg, 0.73 mmol) was dissolved in DMF (5 ml). Cs$_2$CO$_3$ (476 mg, 1.45 mmol) and MeI (0.5 mL) were added. The solution was stirred at RT for overnight. Water and EtOAc were added. The organic layer was separated, washed with brine, dried over Na$_2$SO$_4$, and concentrated. The product was purified by SiO$_2$ chromatography (Hexane/EtOAc 1:0 to 1:1) to give compound 2237B (295 mg, 95.1%).

Part B

Compound 2237B (140 mg, 0.33 mmol) was stirred with NH$_3$/MeOH (7N, 3 mL) in a pressure tube at 110° C. for three days. After cooling down, the solvent was removed by rotary evaporator and the product was purified by sgc (DCM/MeOH/NH$_3$—H$_2$O: 20; 1:0.1 to 10:1:0.1) to give compound 2237C (67 mg, 49%).

Compound 2237 were prepared by the methods described in Example 31 and Example 6.

Example 32

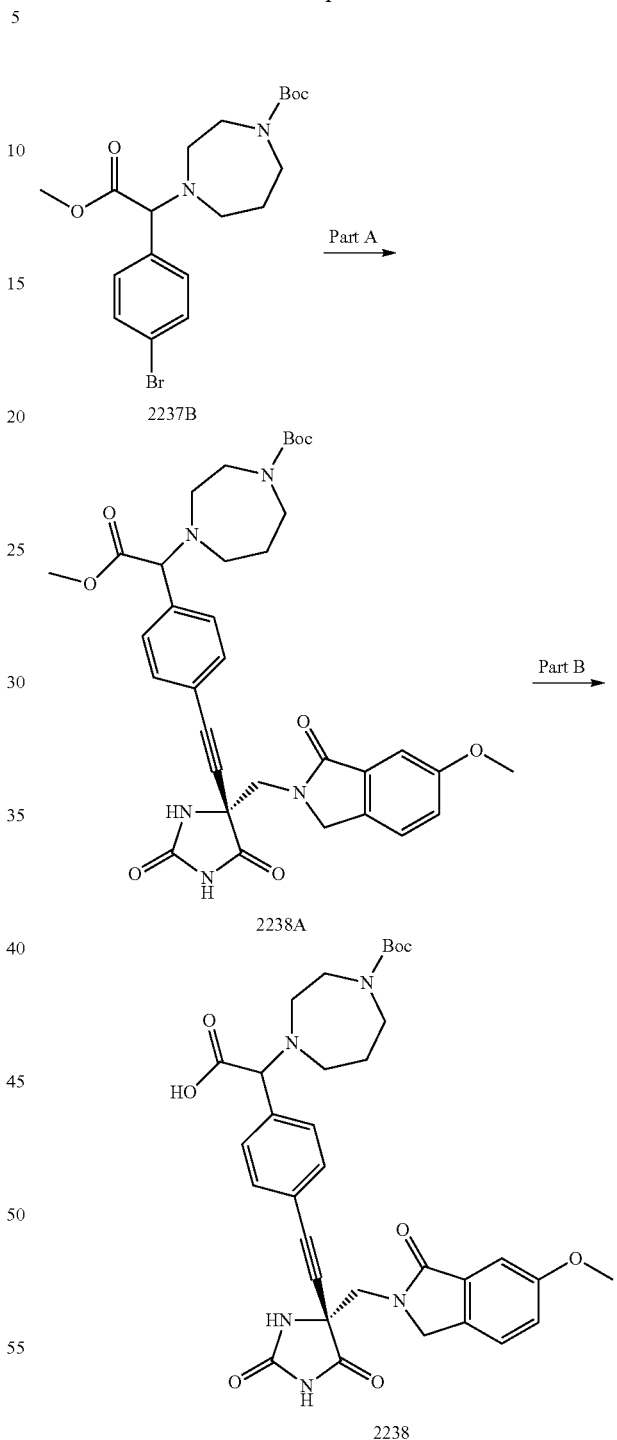

Part A

Compound 2238A was prepared by the method described in Example 6.

Part B

Compound 2238A (76 mg, 0.118 mmol) was dissolved in THF/water (2:1, 1.5 mL) solution. LiOH (11.3 mg, 0.471 mmol) was added. The solution was stirred at 70° C. for overnight. The product was purified by C18 chromatography (CH₃CN/H₂O, 5% to 90%, with 0.1% HCO₂H) to give compound 2238 (56 mg, 75.1%).

Example 33

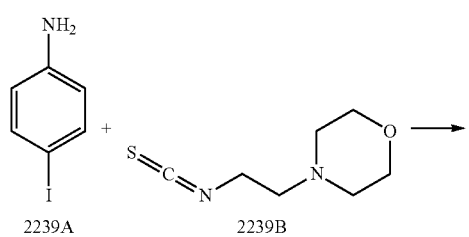

2239A    2239B

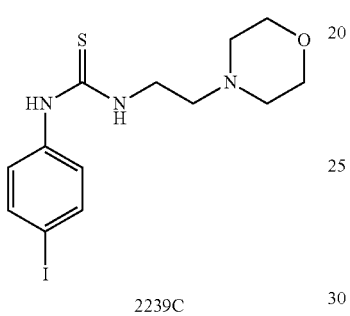

2239C

Compound 2239A (1.65 g, 7.54 mmol), 2239B (1.30 g, 7.54 mmol), and DIPEA (1.30 mL, 7.54 mmol) were stirred at DCM (25 mL) for overnight. The solvent was removed and the product was purified by sgc (DCM/MeOH: 0% to 5%) to give compound 2239C (1.88 g, 63.7%).

Compound 2239 were prepared by the methods described in Example 33 and Example 6.

Example 34

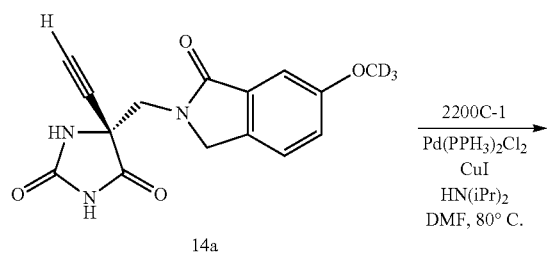

14a

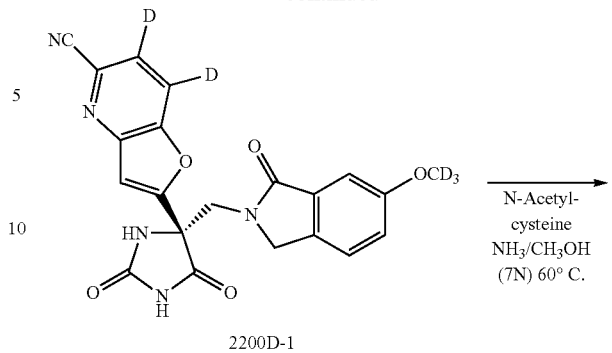

2200D-1

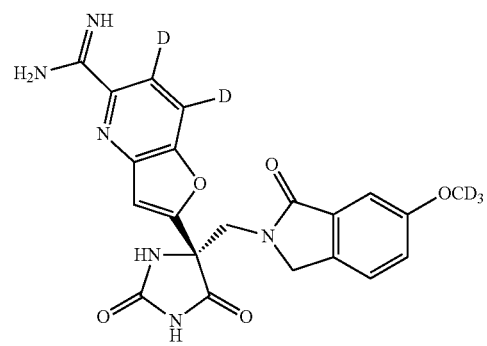

2242

Deuterated 2200 (2242)

Compound 2242 is prepared following the procedure of Example 22. Deuterated intermediate 14a is obtained from 6a following the procedures described in Example 2 and Example 3. Compound 6a itself can be obtained following the procedure in Example 1, starting from the known compound 1a-1. Compound 14a is reacted with intermediate 2200C-1 which is obtained following the procedure in Example 22 by first converting commercially available 2200A-1 to 2200 A4 following published procedures in the following references: Garrett, Mark D.; Scott, Robin; Sheldrake, Gary N.; Dalton, Howard; Goode, Paul. Organic & Biomolecular Chemistry (2006), 4(14), 2710-2715; Allen, C. F. H.; Thirtle, John R. USA. Organic Syntheses (1946 John Wiley & Sons, Inc.; and Koch, Volker; Schnatterer, Stefan. Synthesis (1990), (6), 497-8.

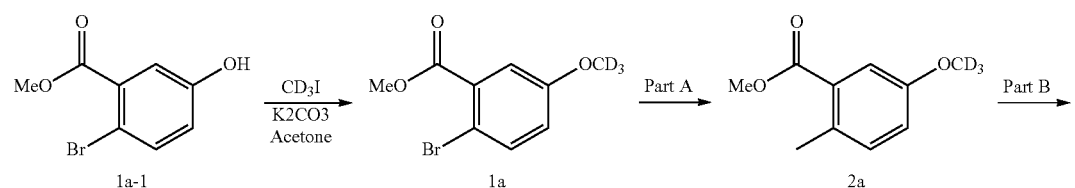

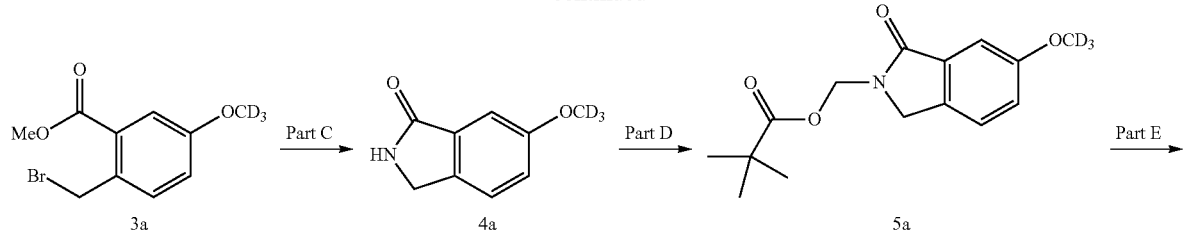

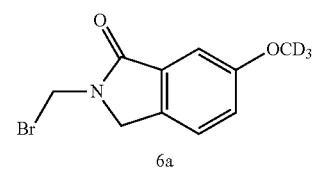

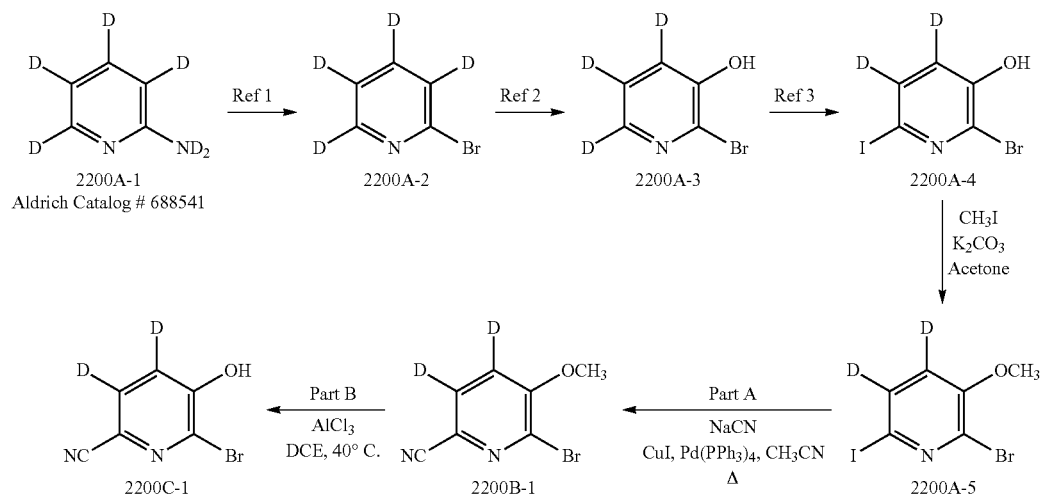

Example 35

Assay for Inhibition of TNF-α Production from Human Whole Blood (hWBA)

Human whole blood was diluted 1:1 with serum free medium (RPMI, L-glutamine, Pen-Strep, HEPES) and incubated with a test compound in a final volume of 360 μL for 1 h at 37° C. Forty microliters of LPS (10 μg/mL) was then added. Supernatant was collected after 3.5 h incubation and the concentration of TNF-α was determined by ELISA (R&D Systems). The concentration of the test compound which inhibits 50% of the amount of TNF-α from the control untreated control was determined. The $IC_{50}$ values for representative compounds of the formulae (I)-(IX) are shown below in Tables A and B.

Example 36

Area Under the Curve Determinations of Plasma Levels in Rats (rrAUC)

To gain insight into the pharmacokinetic properties of the compounds of formula (I), plasma levels of the compounds in rats were determined according to the protocol described in Korfmacher, W. A.; Cox, K. A.; Ng, K. J.; Veals, J.; Hsieh, Y.; Wainhaus, S.; Broske, L.; Prelusky, D.; Nomeir, A.; White, R. E. *Rapid Commun. Mass Spectrom,* 2001, 15, 335, Briefly, rats, after an overnight fast, were dosed orally with the test compound at a dose of 10 mg/kg in a 5 mL/kg dose volume. Blood was collected at 0.5, 1, 2, 3, 4, and 6 h post-dosing. Mass spectrometry using high performance liquid chromatography was used to identify and measure the concentrations of the test compounds in the plasma at the various time points. The parent ion of each test compound was used to identify and quantitate the compounds in plasma. The area under the curve (AUC) data for representative compounds of the formulae (I)-(IX) are shown below in in Tables A and B.

The following compounds were prepared using previously described procedures:

103

104

TABLE A

| ID | Structure | Exact Mass | Mass Obsvd | hWBA[2] IC$_{50}$ (nM) | RR[1] AUC (nM · h) |
|---|---|---|---|---|---|
| 1700 | 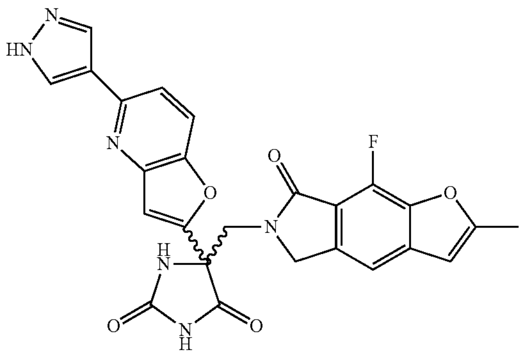 | 500.1 | 501.3 | 500.7 | |
| 1701 | 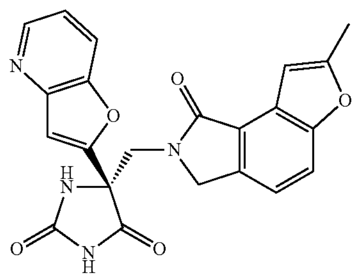 [SMILES: Cc1cc2c3c(ccc2o1)CN(C[C@@]1(c2cc4ncccc4o2)NC(=O)NC1=O)C3=O] | 416.1 | 417.2 | >10000 | |
| 1702 | 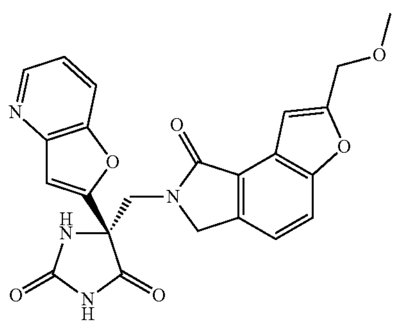 [SMILES: COCc1cc2c3c(ccc2o1)CN(C[C@@]1(c2cc4ncccc4o2)NC(=O)NC1=O)C3=O] | 446.1 | 447.2 | >10000 | |
| 1703 | 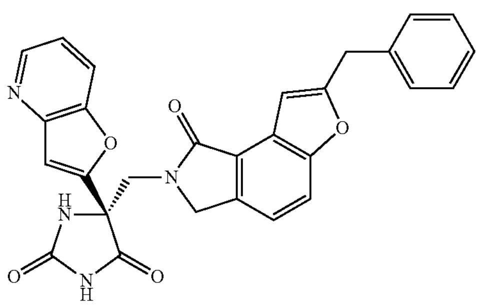 [SMILES: O=C1NC(=O)[C@](CN2Cc3ccc4oc(Cc5ccccc5)cc4c3C2=O)(c2cc3ncccc3o2)N1] | 492.1 | 493.3 | >10000 | |
| 1704 | 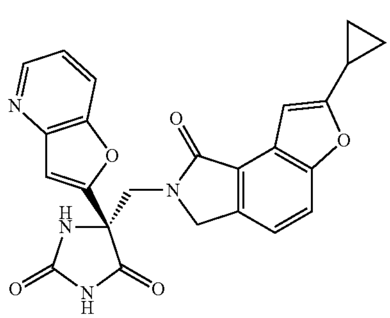 [SMILES: O=C1NC(=O)[C@](CN2Cc3ccc4oc(C5CC5)cc4c3C2=O)(c2cc3ncccc3o2)N1] | 442.1 | 443.2 | >10000 | |

TABLE A-continued

| ID | Structure | Exact Mass | Mass Obsvd | hWBA[2] IC$_{50}$ (nM) | RR[1] AUC (nM·h) |
|---|---|---|---|---|---|
| 1705 | 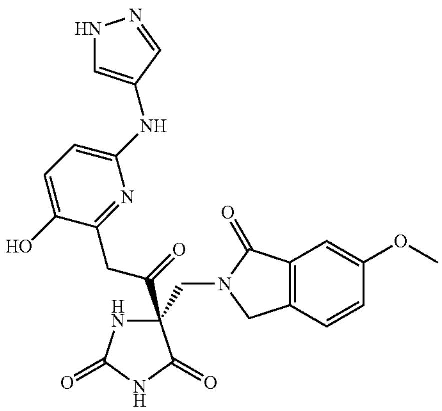 [SMILES: COc1ccc2c(c1)C(=O)N(C[C@@]1(C(=O)Cc3nc(Nc4cn[nH]c4)ccc3O)NC(=O)NC1=O)C2] | 491.2 | 492.3 | 292 | |
| 1707 | 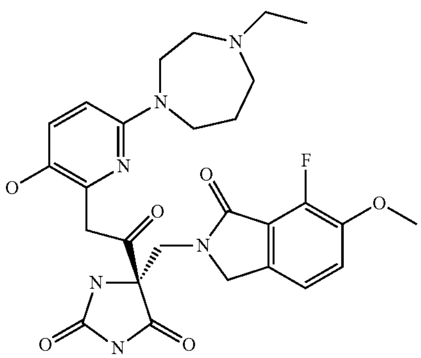 [SMILES: CCN1CCCN(c2ccc(O)c(CC(=O)[C@]3(CN4Cc5ccc(OC)c(F)c5C4=O)NC(=O)NC3=O)n2)CC1] | 554.2 | 555.3 | 1570 | |
| 112 | 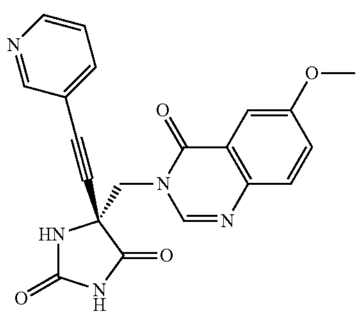 [SMILES: COc1ccc2ncn(C[C@@]3(C#Cc4cccnc4)NC(=O)NC3=O)c(=O)c2c1] | 389.1 | 390.1 | 10000001 | |
| 113 | 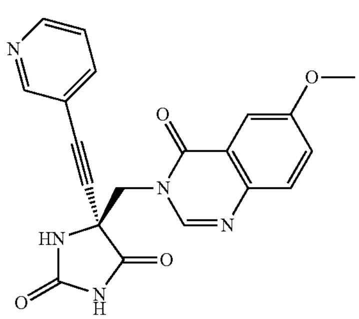 [SMILES: COc1ccc2ncn(C[C@]3(C#Cc4cccnc4)NC(=O)NC3=O)c(=O)c2c1] | 389.1 | 390.1 | 10000001 | |

TABLE A-continued

| ID | Structure | Exact Mass | Mass Obsvd | hWBA[2] IC$_{50}$ (nM) | RR[1] AUC (nM·h) |
|---|---|---|---|---|---|
| 114 | 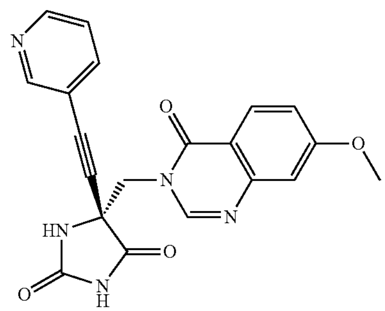 [SMILES: COc1ccc2c(=O)n(C[C@@]3(C#Cc4cccnc4)NC(=O)NC3=O)cnc2c1] | 389.1 | 390.1 | 10000001 | |
| 1150 | 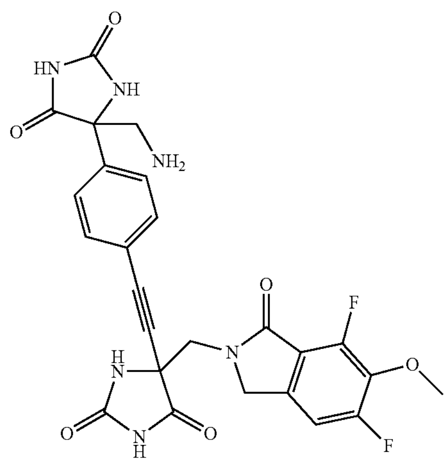 [SMILES: COc1c(F)cc2c(c1F)C(=O)N(CC1(C#Cc3ccc(C4(CN)NC(=O)NC4=O)cc3)NC(=O)NC1=O)C2] | 538.14 | 539.3 | >10,000 | |
| 1160 | 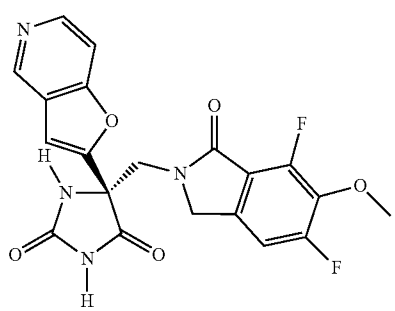 [SMILES: COc1c(F)cc2c(c1F)C(=O)N(C[C@@]1(c3cc4cnccc4o3)NC(=O)NC1=O)C2] | 428.09 | 429.2 | 7142 | |
| 1165 | 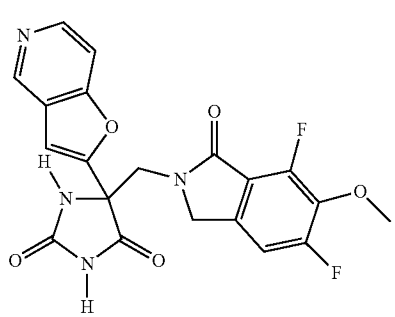 [SMILES: COc1c(F)cc2c(c1F)C(=O)N(CC1(c3cc4cnccc4o3)NC(=O)NC1=O)C2] | 428.09 | 429.2 | >10,000 | |

TABLE A-continued

| ID | Structure | Exact Mass | Mass Obsvd | hWBA² IC₅₀ (nM) | RR¹ AUC (nM · h) |
|---|---|---|---|---|---|
| 1170 | 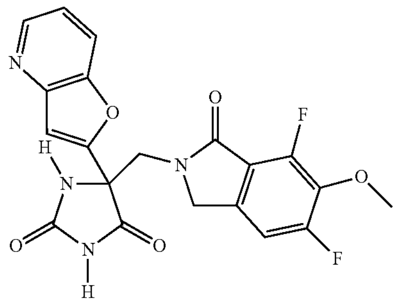 [SMILES: COc1c(F)cc2c(c1F)C(=O)N(CC1(c3cc4ncccc4o3)NC(=O)NC1=O)C2] | 428.09 | 429.2 | >10,000 | |
| 1175 | 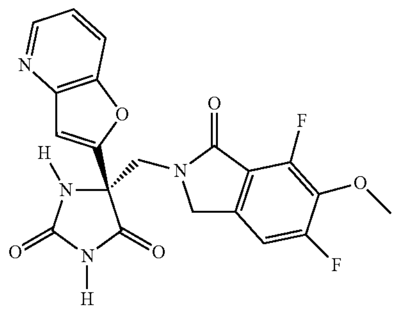 [SMILES: COc1c(F)cc2c(c1F)C(=O)N(C[C@@]1(c3cc4ncccc4o3)NC(=O)NC1=O)C2] | 428.09 | 429.2 | 7120 | |
| 1180 | 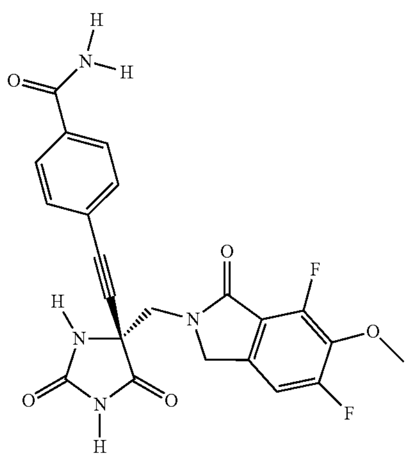 [SMILES: COc1c(F)cc2c(c1F)C(=O)N(C[C@@]1(C#Cc3ccc(C(N)=O)cc3)NC(=O)NC1=O)C2] | 454.11 | 455.3 | 1431 | |
| 1190 | 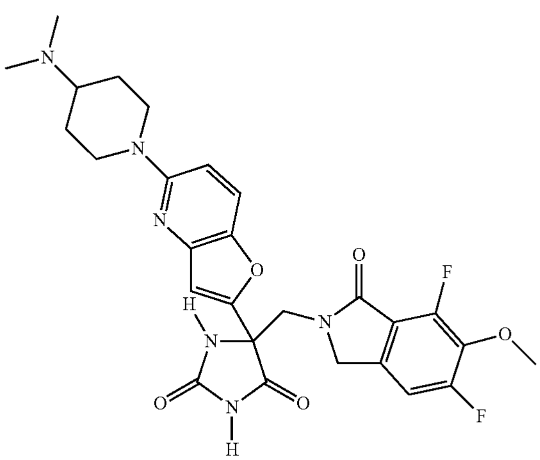 | 554.21 | 555.3 | >10,000 | |

TABLE A-continued

| ID | Structure | Exact Mass | Mass Obsvd | hWBA[2] IC$_{50}$ (nM) | RR[1] AUC (nM·h) |
|---|---|---|---|---|---|
| 1120A | 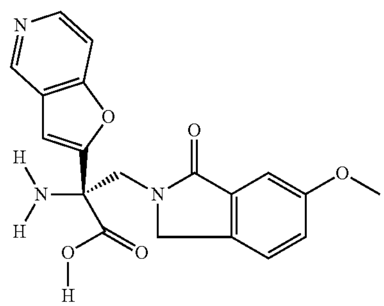 [SMILES: COc1ccc2c(c1)C(=O)N(C[C@@](N)(C(=O)O)c1cc3cnccc3o1)C2] | 367.11 | 368.08 | >10,000 | |
| 1120B | 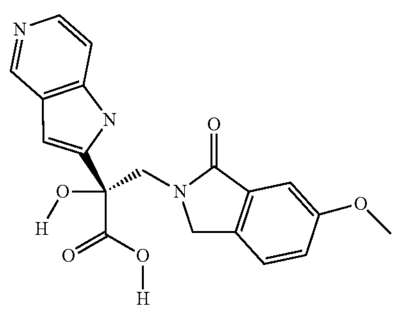 [SMILES: COc1ccc2c(c1)C(=O)N(C[C@@](O)(C(=O)O)c1cc3cnccc3[nH]1)C2] | 368.1 | 369.2 | >10,000 | |
| 1500 | 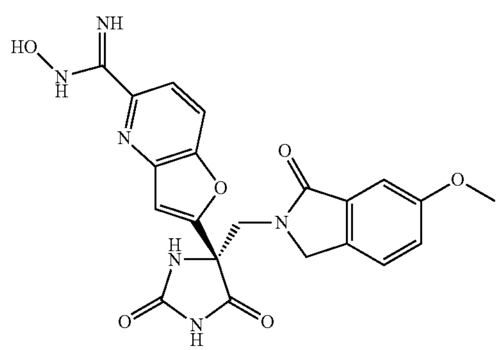 [SMILES: COc1ccc2c(c1)C(=O)N(C[C@@]1(c3cc4nc(C(=N)NO)ccc4o3)NC(=O)NC1=O)C2] | 450.4 | 451.2 | | 640.2 |
| 1501 | 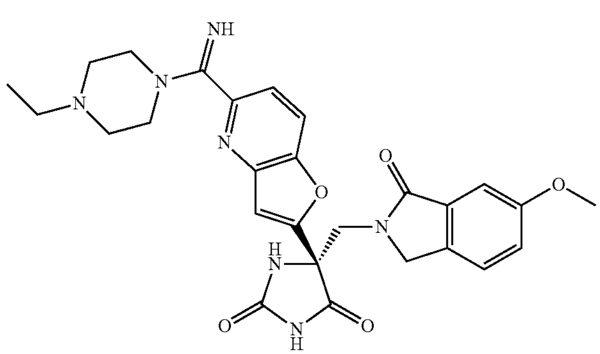 [SMILES: CCN1CCN(C(=N)c2ccc3oc([C@]4(CN5Cc6ccc(OC)cc6C5=O)NC(=O)NC4=O)cc3n2)CC1] | 531.6 | 533.3 | | 1891.5 |

TABLE A-continued
| ID | Structure | Exact Mass | Mass Obsvd | hWBA[2] IC$_{50}$ (nM) | RR[1] AUC (nM·h) |
|---|---|---|---|---|---|
| 1502 | 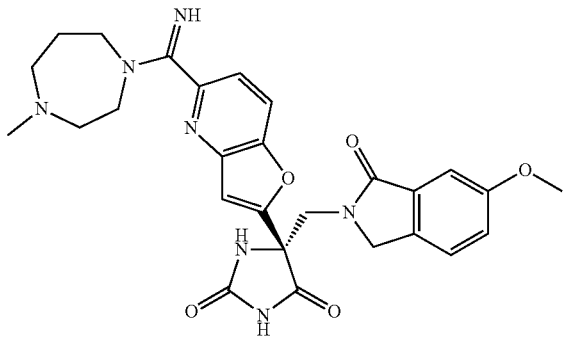 | 531.6 | 533.3 | 1821.1 | |
| 1304 | 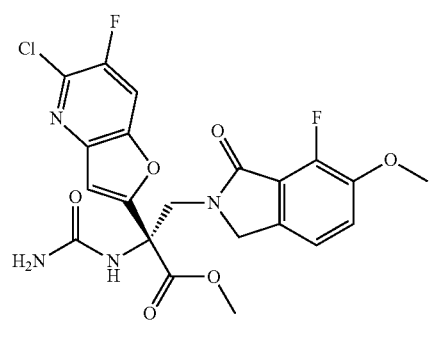 [SMILES: COC(=O)[C@@](CN1Cc2ccc(OC)c(F)c2C1=O)(NC(N)=O)c1cc2nc(Cl)c(F)cc2o1] | 494.08 | 495.3 | 3098 | 113 |
[1]RR AUC = rapid rat AUC
[2]hWBA = human whole blood assay
TABLE B
| ID | Structures | Exact Mass | Mass Obsvd | hWBA[2] IC$_{50}$ nM | RR AUC[1] (nM·h) |
|---|---|---|---|---|---|
| 2200 | 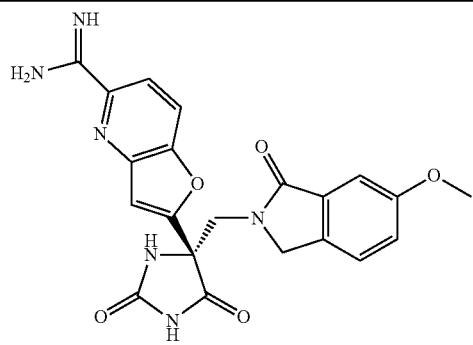 | 434.4 | 435.2 | 307 | |
| 2201 | 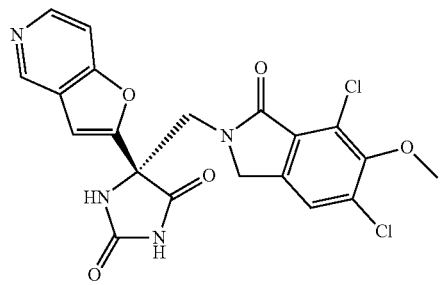 [SMILES: COc1c(Cl)cc2c(c1Cl)C(=O)N(C[C@@]1(c3cc4cnccc4o3)NC(=O)NC1=O)C2] | 460.03 | 461.0 | 10000 | |

TABLE B-continued

| ID | Structures | Exact Mass | Mass Obsvd | hWBA[2] IC$_{50}$ nM | RR AUC[1] (nM·h) |
|---|---|---|---|---|---|
| 2203 | 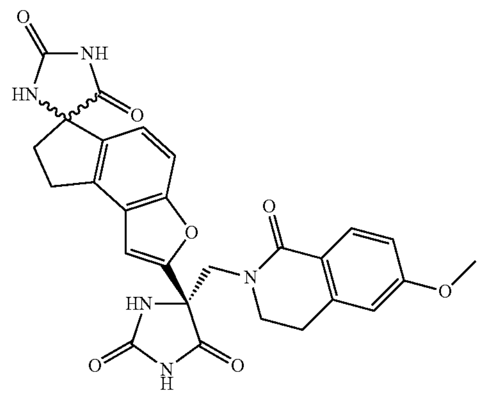 | 529.2 | 530.3 | 3559 | |
| 2206 | 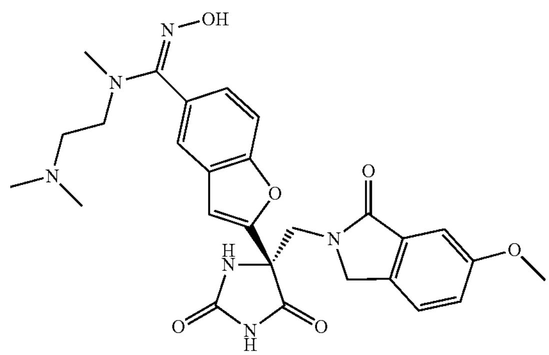 | 534.2 | 535.3 | 384 | |
| 2207 | 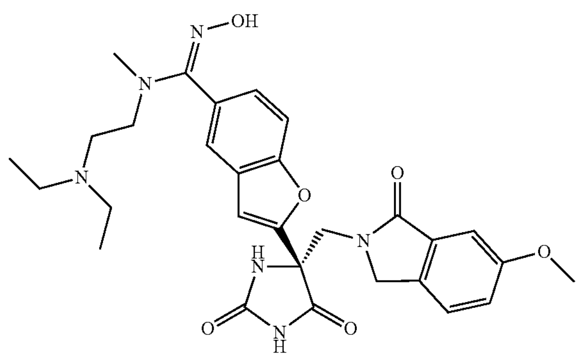 [SMILES: CCN(CC)CCN(C)/C(=N/O)c1ccc2oc([C@]3(CN4Cc5ccc(OC)cc5C4=O)NC(=O)NC3=O)cc2c1] | 562.3 | 563.3 | 308 | 0 |
| 2208 | 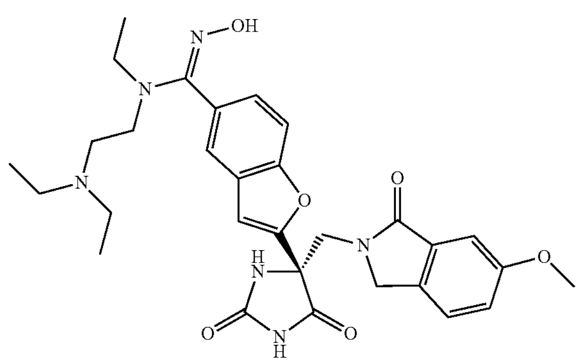 [SMILES: CCN(CC)CCN(CC)/C(=N/O)c1ccc2oc([C@]3(CN4Cc5ccc(OC)cc5C4=O)NC(=O)NC3=O)cc2c1] | 576.3 | 577.3 | 281 | |

TABLE B-continued
| ID | Structures | Exact Mass | Mass Obsvd | hWBA[2] IC$_{50}$ nM | RR AUC[1] (nM · h) |
|---|---|---|---|---|---|
| 2209 | 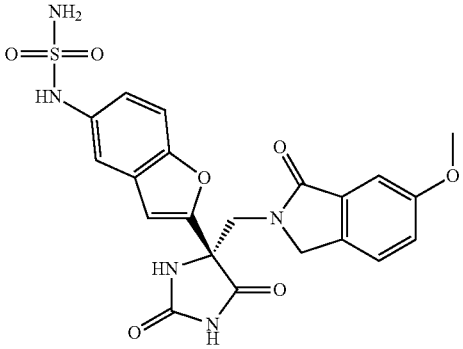 [SMILES: COc1ccc2c(c1)C(=O)N(C[C@@]1(c3cc4cc(NS(N)(=O)=O)ccc4o3)NC(=O)NC1=O)C2] | 485.10 | 486.1 | 315 | |
| 2210 | 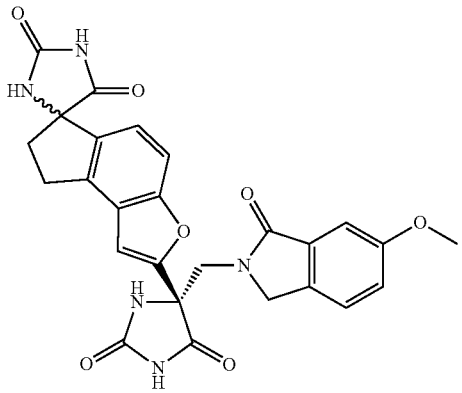 [SMILES: COc1ccc2c(c1)C(=O)N(C[C@@]1(c3cc4c5c(ccc4o3)C3(CC5)NC(=O)NC3=O)NC(=O)NC1=O)C2] | 515.14 | 516.3 | 187 | 321 |
| 2211 | 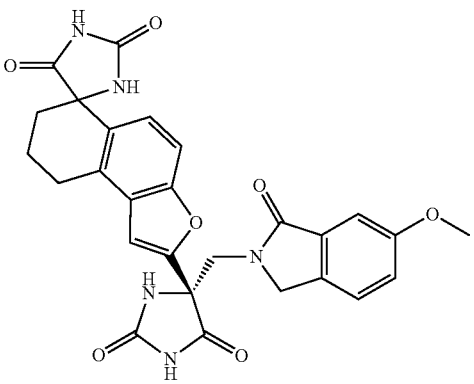 [SMILES: COc1ccc2c(c1)C(=O)N(C[C@@]1(c3cc4c5c(ccc4o3)C3(CCC5)NC(=O)NC3=O)NC(=O)NC1=O)C2] | 529.16 | 530.3 | 570 | 55 |
| 2213 | 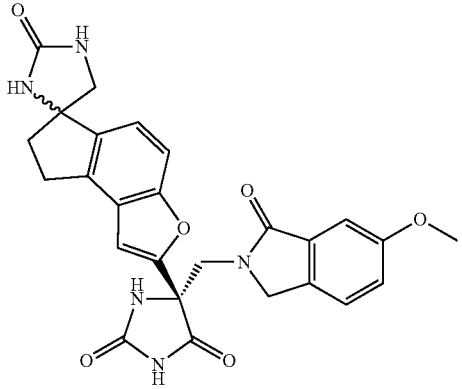 [SMILES: COc1ccc2c(c1)C(=O)N(C[C@@]1(c3cc4c5c(ccc4o3)C3(CC5)CNC(=O)N3)NC(=O)NC1=O)C2] | 501.16 | 502.3 | 335 | 0 |

TABLE B-continued

| ID | Structures | Exact Mass | Mass Obsvd | hWBA[2] IC$_{50}$ nM | RR AUC[1] (nM·h) |
|---|---|---|---|---|---|
| 2214 | 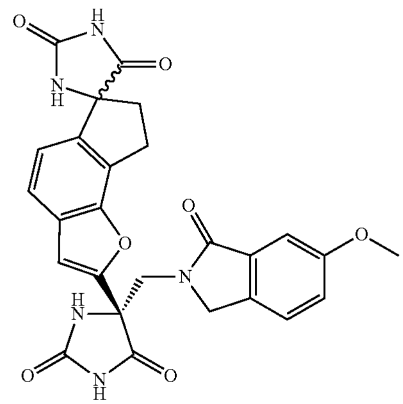 [SMILES: COc1ccc2c(c1)C(=O)N(C[C@@]1(c3cc4ccc5c(c4o3)CCC53NC(=O)NC3=O)NC(=O)NC1=O)C2] | 515.14 | 516.3 | 1011 | 128 |
| 2215 | 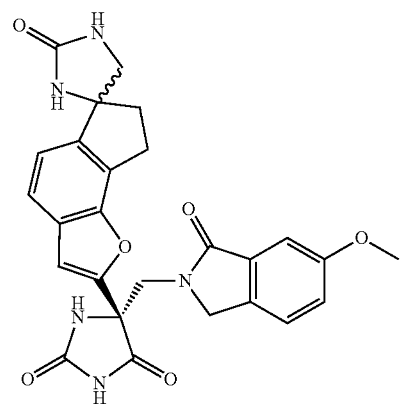 [SMILES: COc1ccc2c(c1)C(=O)N(C[C@@]1(c3cc4ccc5c(c4o3)CCC53CNC(=O)N3)NC(=O)NC1=O)C2] | 501.16 | 502.3 | 628 | 0 |
| 2216 | 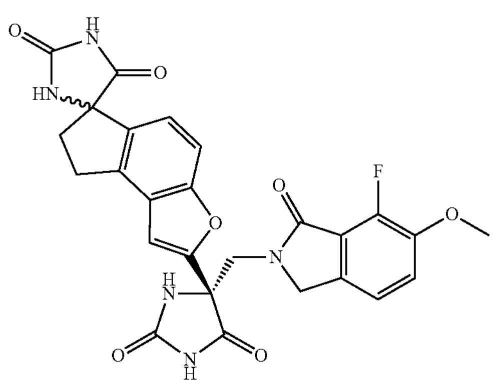 [SMILES: COc1ccc2c(c1F)C(=O)N(C[C@@]1(c3cc4c5c(ccc4o3)C3(CC5)NC(=O)NC3=O)NC(=O)NC1=O)C2] | 533.13 | 534.3 | 145 | 1604 |
| 2217 | 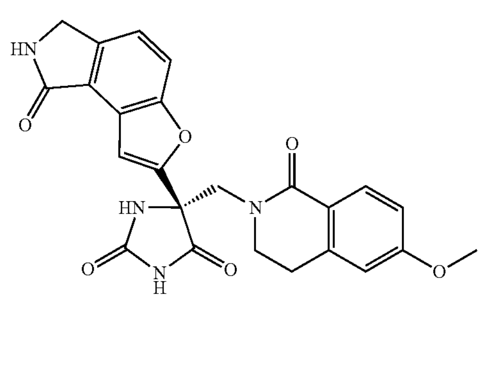 [SMILES: COc1ccc2c(c1)CCN(C[C@@]1(c3cc4c5c(ccc4o3)CNC5=O)NC(=O)NC1=O)C2=O] | 460.1 | 461.3 | 1940 | |

TABLE B-continued

| ID | Structures | Exact Mass | Mass Obsvd | hWBA[2] IC$_{50}$ nM | RR AUC[1] (nM·h) |
|---|---|---|---|---|---|
| 2218 | 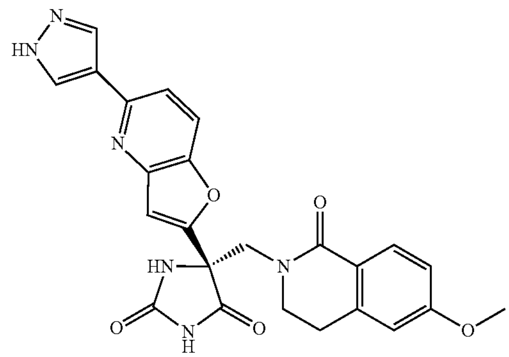 [SMILES: COc1ccc2c(c1)CCN(C[C@@]1(c3cc4nc(-c5cn[nH]c5)ccc4o3)NC(=O)NC1=O)C2=O] | 472.1 | 473.3 | 284 | 0 |
| 2219 | 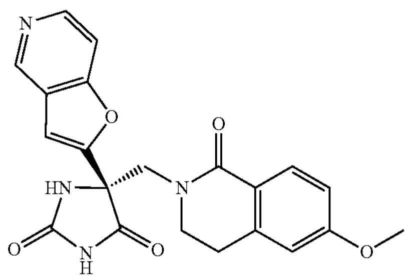 [SMILES: COc1ccc2c(c1)CCN(C[C@@]1(c3cc4cnccc4o3)NC(=O)NC1=O)C2=O] | 406.1 | 407.2 | 1374 | |
| 2223 | 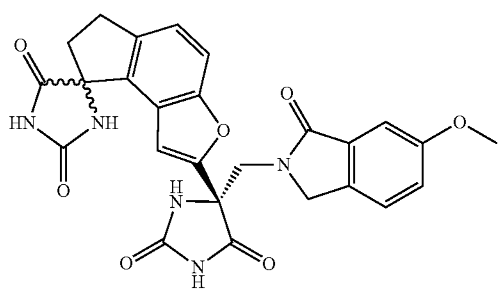 | 515.14 | | 1001 | |
| 2224 | 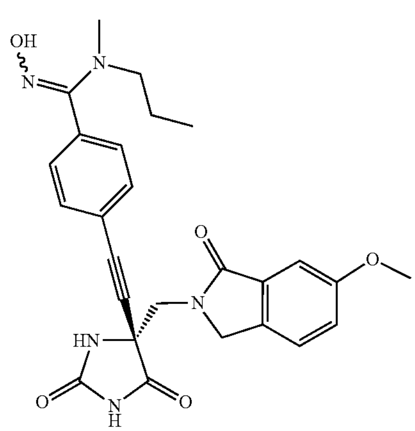 [SMILES: CCCN(C)C(=NO)c1ccc(C#C[C@]2(CN3Cc4ccc(OC)cc4C3=O)NC(=O)NC2=O)cc1] | 489.2 | 490.3 | 239 | |

TABLE B-continued
| ID | Structures | Exact Mass | Mass Obsvd | hWBA[2] IC$_{50}$ nM | RR AUC[1] (nM·h) |
|---|---|---|---|---|---|
| 2227 | 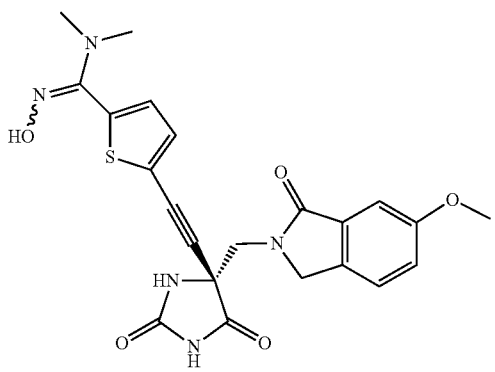 [SMILES: COc1ccc2c(c1)C(=O)N(C[C@@]1(C#Cc3ccc(C(=NO)N(C)C)s3)NC(=O)NC1=O)C2] | 467.1 | 468.3 | 813 | |
| 2228 | 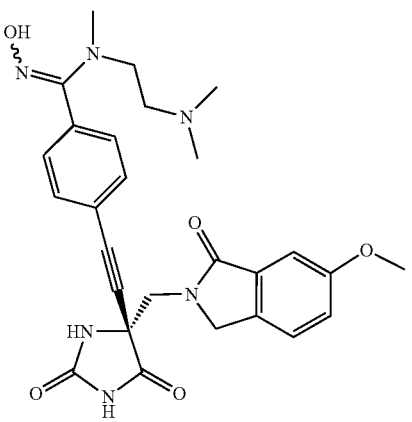 [SMILES: COc1ccc2c(c1)C(=O)N(C[C@@]1(C#Cc3ccc(C(=NO)N(C)CCN(C)C)cc3)NC(=O)NC1=O)C2] | 518.2 | 519.3 | 91 | |
| 2229 | 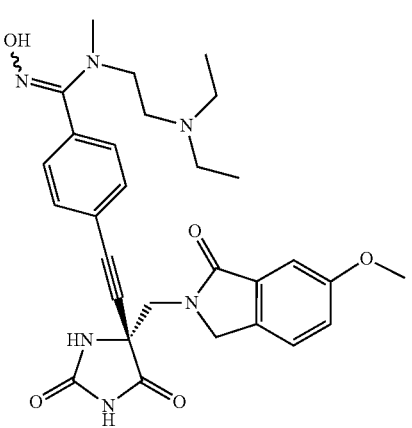 [SMILES: CCN(CC)CCN(C)C(=NO)c1ccc(C#C[C@]2(CN3Cc4ccc(OC)cc4C3=O)NC(=O)NC2=O)cc1] | 546.2 | 547.3 | 96 | |

TABLE B-continued

| ID | Structures | Exact Mass | Mass Obsvd | hWBA[2] IC$_{50}$ nM | RR AUC[1] (nM · h) |
|---|---|---|---|---|---|
| 2230 | 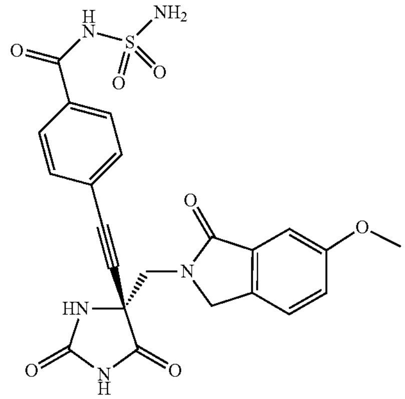 [SMILES: COc1ccc2c(c1)C(=O)N(C[C@@]1(C#Cc3ccc(C(=O)NS(N)(=O)=O)cc3)NC(=O)NC1=O)C2] | 497.1 | 498.3 | 434 | |
| 2231 | 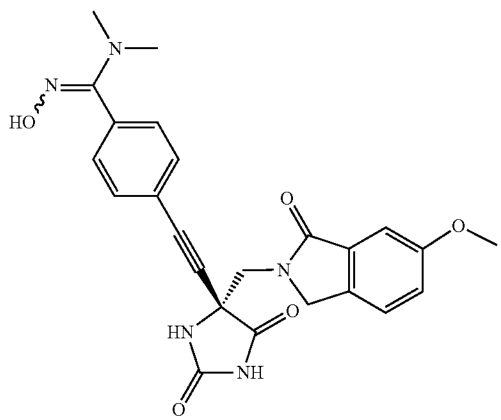 [SMILES: COc1ccc2c(c1)C(=O)N(C[C@@]1(C#Cc3ccc(C(=NO)N(C)C)cc3)NC(=O)NC1=O)C2] | 461.1 | 462.3 | 152 | |
| 2234 | 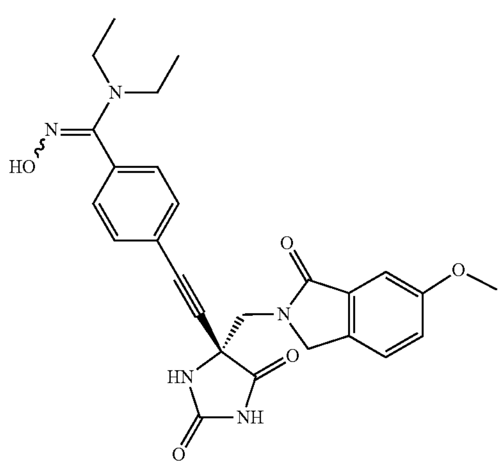 [SMILES: CCN(CC)C(=NO)c1ccc(C#C[C@]2(CN3Cc4ccc(OC)cc4C3=O)NC(=O)NC2=O)cc1] | 489.2 | 490.3 | 205 | |

TABLE B-continued

| ID | Structures | Exact Mass | Mass Obsvd | hWBA[2] IC$_{50}$ nM | RR AUC[1] (nM·h) |
|---|---|---|---|---|---|
| 2237 | 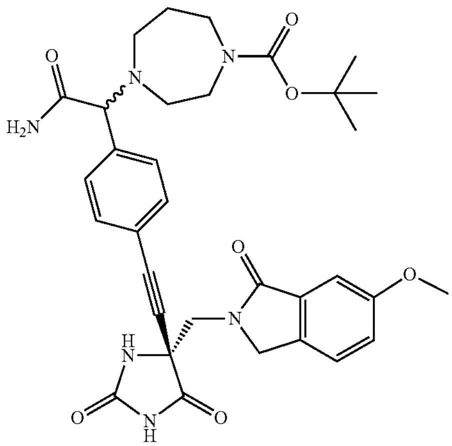 [SMILES: COc1ccc2c(c1)C(=O)N(C[C@@]1(C#Cc3ccc(C(C(N)=O)N4CCCN(C(=O)OC(C)(C)C)CC4)cc3)NC(=O)NC1=O)C2] | 630.28 | 631.3 | 1184 | |
| 2238 | 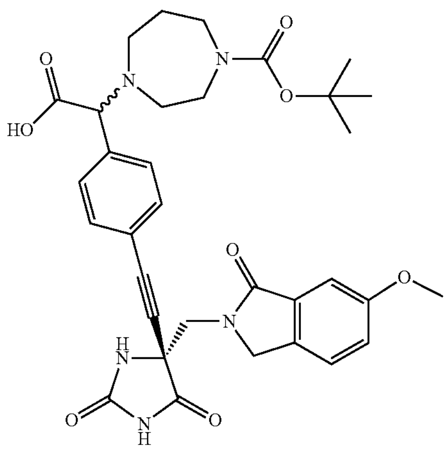 [SMILES: COc1ccc2c(c1)C(=O)N(C[C@@]1(C#Cc3ccc(C(C(=O)O)N4CCCN(C(=O)OC(C)(C)C)CC4)cc3)NC(=O)NC1=O)C2] | 631.26 | 632.3 | 1025 | |
| 2239 | 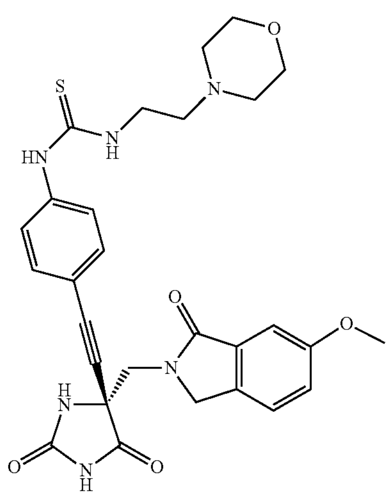 [SMILES: COc1ccc2c(c1)C(=O)N(C[C@@]1(C#Cc3ccc(NC(=S)NCCN4CCOCC4)cc3)NC(=O)NC1=O)C2] | 562.20 | 563.3 | 267 | 0 |

TABLE B-continued

| ID | Structures | Exact Mass | Mass Obsvd | hWBA[2] IC$_{50}$ nM | RR AUC[1] (nM·h) |
|---|---|---|---|---|---|
| 2241 | 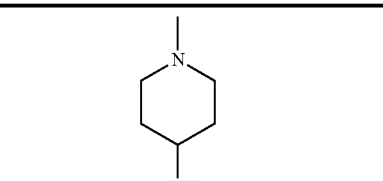 | 522.22 | 523.3 | | 1274 |

[1]RR AUC = rapid rat AUC
[2]hWBA = human whole blood assay

It will be appreciated by those skilled in the art that changes could be made to the embodiments described above without departing from the broad inventive concept thereof. It is understood, therefore, that this invention is not limited to the particular embodiments disclosed, but it is intended to cover modifications that are within the spirit and scope of the invention, as defined by the appended claims.

Each document referred to herein is incorporated by reference in its entirety for all purposes.

Therefore, we claim:
1. A compound represented by Formula (I):

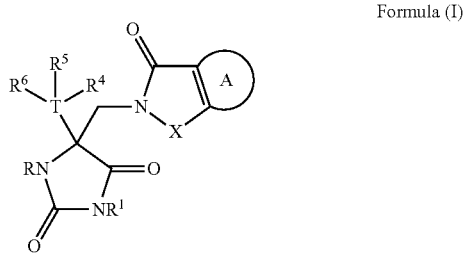

Formula (I)

or a pharmaceutically acceptable salt thereof, wherein:
ring A is aryl or heteroaryl, wherein said aryl or heteroaryl is unsubstituted or substituted with $R^2$ or —$OR^3$, wherein $R^2$ is H or halo, and $R^3$ is H or alkyl;
T is aryl or heteroaryl, substituted with an $R^4$, $R^5$, and $R^6$ as shown;
X is selected from the group consisting of —S—, —O—, —S(O)$_2$—, —S(O)—, —(CR$^8_2$)$_p$— and —N(R')—;
p is 1 to 3;
R' is selected from the group consisting of H, alkyl, and aryl;
R is selected from the group consisting of H, alkyl, cycloalkyl, cycloalkenyl, heterocyclyl, heterocyclenyl, aryl, heteroaryl, —C(=O)alkyl, —C(=O)cycloalkyl, —C(=O) heterocyclyl, —C(=O)aryl, —C(=O)heteroaryl, —C(=O) O-alkyl, —C(=O)O-cycloalkyl, —C(=O)O-heterocyclyl, —C(=O)O-aryl, and —C(=O)O-heteroaryl;
$R^1$ is selected from the group consisting of H and —C(R$^7$)$_2$-(Q)$_n$R$^9$;
$R^4$ is selected from the group consisting of H, alkyl, and halogen;
$R^5$ and $R^6$ are substituents on adjacent carbon atoms, wherein $R^5$ and $R^6$ together with the carbon atoms to which they are attached form a first five-to eight-membered cycloalkyl, cycloalkenyl, heterocyclyl, or heterocyclenyl; wherein said first five-to eight-membered cycloalkyl, cycloalkenyl, heterocyclyl, or heterocyclenyl contains two radicals on the same carbon atom, and said radicals taken together with the carbon atom to which they are attached form a second five-to eight-membered cycloalkyl, cycloalkenyl, heterocyclyl, or heterocyclenyl; wherein said first five-to eight-membered cycloalkyl, cycloalkenyl, heterocyclyl, or heterocyclenyl, optionally with said second five-to eight-membered cycloalkyl, cycloalkenyl, heterocyclyl, or heterocyclenyl is unsubstituted or substituted with one to four $R^{10}$ moieties;
each $R^7$ independently is selected from the group consisting of H, alkyl, and aryl;
each $R^8$ independently is selected from the group consisting of H, alkyl, and aryl;
$R^9$ is selected from the group consisting of H, alkyl, heterocyclyl, aryl, heteroaryl, —C(=O)N(R$^{12}$)$_2$, —C(=O)-alkyl, C(=O)-cycloalkyl, C(=O)-heterocyclyl, —C(=O)-aryl, —C(=O)-heteroaryl, —C(=O)—O-alkyl, —C(=O)—O-cycloalkyl, —C(=O)—O-heterocyclyl, —C(=O)—O-aryl, —C(=O)—O-heteroaryl, —P(=O)(—OH)$_2$, —P(=O)(—O-alkyl)$_2$, wherein when each of said "cycloalkyl", "heterocyclyl", "aryl", or "heteroaryl" in any of the aforementioned $R^9$ groups contains two radicals on adjacent carbon atoms, said radicals may optionally be taken together with the carbon atoms to which they are attached to form a five-or six-membered cycloalkyl, aryl, heterocyclyl or heteroaryl ring;

each $R^{10}$ is independently selected from the group consisting of cyano, nitro, —OC(O)$R^{11}$, —C($R^{11}$)=N—O$R^{11}$, —O$R^{11}$, —S$R^{11}$, —N($R^{11}$)$_2$, —S(O)$R^{11}$, —S(O)$_2R^{11}$, —N($R^{11}$)S(O)$_2R^{11}$, —N($R^{11}$)—C(O)—$R^{11}$, —N($R^{11}$)—C(O)—N($R^{11}$)$_2$, —N($R^{11}$)—C(O)—O$R^{11}$, —OC(O)N($R^{11}$)$_2$, —C(O)N($R^{11}$)—S(O)$_2R^{11}$, —S(O)$_2$N($R^{11}$)—C(O)—$R^{11}$, —C(O)N($R^{11}$)C(O)$R^{11}$, —C(O)N($R^{11}$)C(O)N$R^{11}$, —S(O)$_2$N($R^{11}$)$_2$, —N($R^{11}$)—C(=N$R^{11}$)—N($R^{11}$)$_2$, —N($R^{11}$)—C(=N—CN)—N($R^{11}$)$_2$, -haloalkoxy, —C(O)O$R^{11}$, —C(O)$R^{11}$, —C(O)N($R^{11}$)$_2$, halogen, alkyl, haloalkyl, aryl, heteroaryl, heterocyclyl, heterocyclenyl, cycloalkenyl, and cycloalkyl, with the proviso that there are no adjacent heteroatoms in any of said $R^{10}$;

each $R^{11}$ independently is selected from the group consisting of H, alkyl, cycloalkyl, haloalkyl, hydroxy, heterocyclyl, aryl, and heteroaryl;

Q is selected from the group consisting of —N$R^{12}$—, —O—, —S—, —S(O)—, and —S(O)$_2$—;

each $R^{12}$ is independently selected from the group consisting of H and alkyl; and n is 0 or 1.

2. The compound of claim 1, selected from the group consisting of:

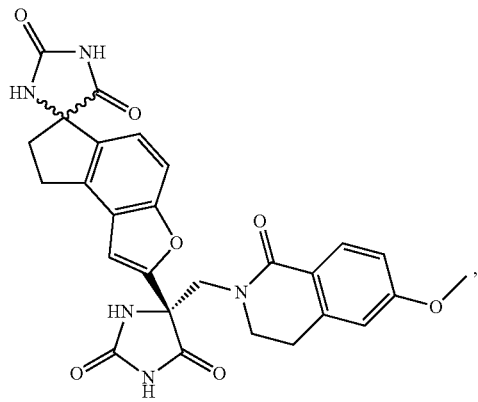

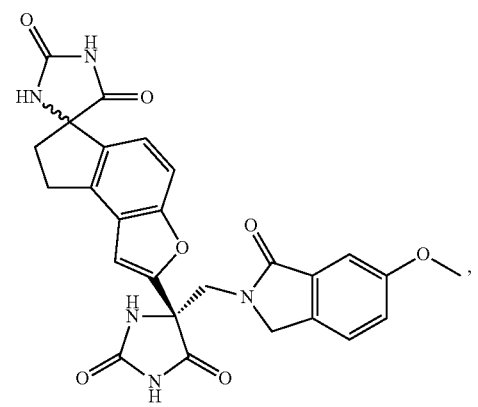

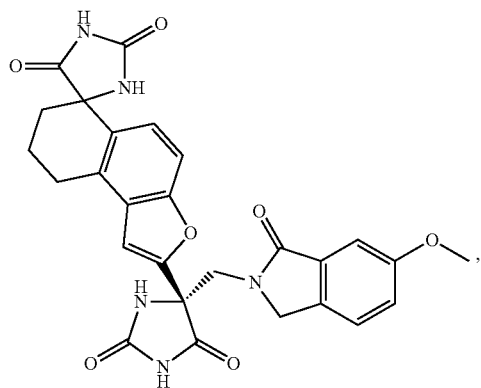

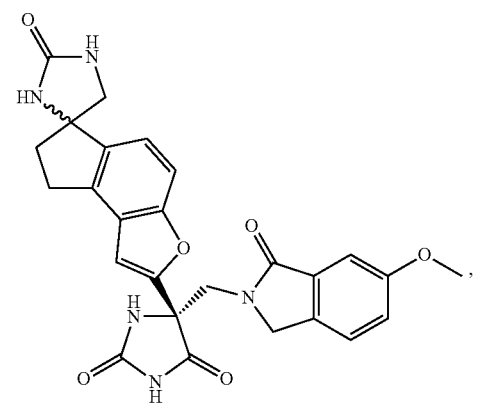

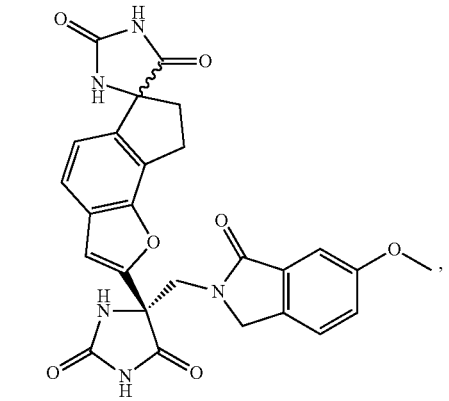

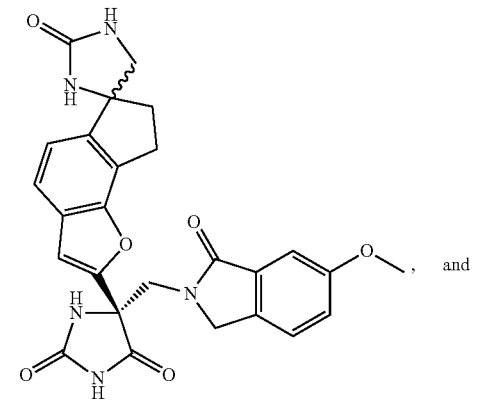, and

133

-continued

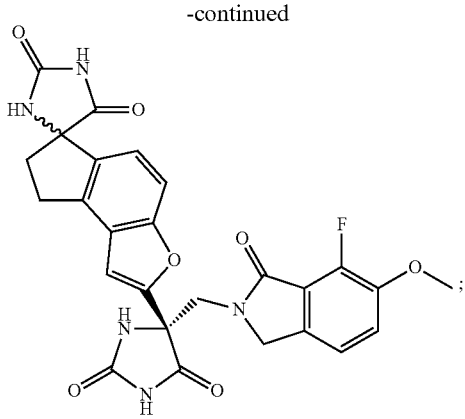

or a pharmaceutically acceptable salt thereof.

3. A compound represented by Formula (II)

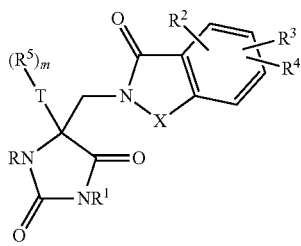

Formula (II)

or a pharmaceutically acceptable salt thereof, wherein:
T is aryl or heteroaryl, each of which is substituted with m $R^5$ substituents as shown;
X is selected from the group consisting of —S—, —O—, —S(O)$_2$—, —S(O)—, —(CR$^6{}_2$)$_p$-and —N(R')—,
p is 1 to 3;
R' is selected from the group consisting of H, alkyl, and aryl;
R is selected from the group consisting of H, alkyl, cycloalkyl, cycloalkenyl, heterocyclyl, heterocyclenyl, aryl, heteroaryl, —C(=O)alkyl, —C(=O)cycloalkyl, —C(=O)heterocyclyl, —C(=O)aryl, —C(=O)heteroaryl, —C(=O)O-alkyl, —C(=O)O-cycloalkyl, —C(=O)O-heterocyclyl, —C(=O)O-aryl, and —C(=O)O-heteroaryl;
$R^1$ is selected from the group consisting of H and —C(R$^6$)$_2$-(Q)$_n$R$^7$;
$R^2$ is selected from the group consisting of H, alkyl, and halogen;
$R^3$ and $R^4$ are substituents on adjacent carbon atoms, wherein $R^3$ and $R^4$ together with the carbon atoms to which they are attached form a first five or six-membered heteroaryl, which is unsubstituted or substituted with one or two substituents independently selected from the group consisting of alkyl and cycloalkyl;
$R^5$ is selected from the group consisting of alkyl, cycloalkyl, heterocyclyl, aryl and heteroaryl;
each $R^6$ independently is selected from the group consisting of H, alkyl, and aryl;
$R^7$ is selected from the group consisting of H, alkyl, heterocyclyl, aryl, heteroaryl, —C(=O)N(R$^8$)$_2$, —C(=O)-alkyl, C(=O)-cycloalkyl, C(=O)-heterocyclyl, —C(=O)-aryl, —C(=O)-heteroaryl, —C(=O)—O-alkyl, —C(=O)—O-cycloalkyl, —C(=O)—O-heterocyclyl, —C(=O)—O-aryl,

134

—C(=O)—O-heteroaryl, —P(=O)(—OH)$_2$, —P(=O)(—O-alkyl)$_2$, wherein when each of said "cycloalkyl", "heterocyclyl", "aryl", or "heteroaryl" in any of the aforementioned R$^9$ groups contains two radicals on adjacent carbon atoms, said radicals may optionally be taken together with the carbon atoms to which they are attached to form a five-or six-membered cycloalkyl, aryl, heterocyclyl or heteroaryl ring;
each $R^8$ is independently selected from the group consisting of H and alkyl;
Q is selected from the group consisting of —NR$^8$—, —O—, —S—, —S(O)—, and —S(O)$_2$—;
n is 0 or 1; and
m is 0-3.

4. The compound of claim 3, selected from the group consisting of:

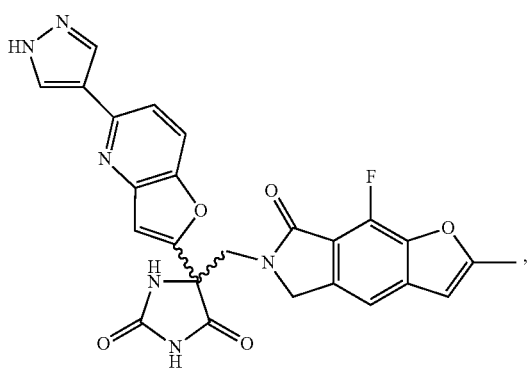

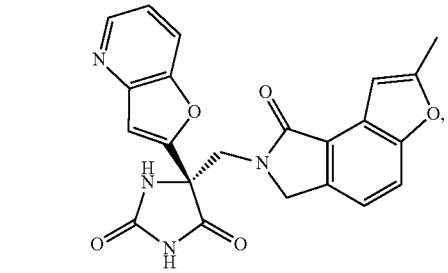

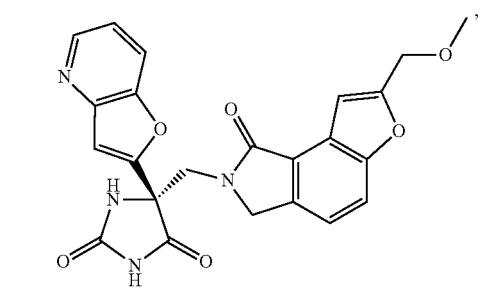

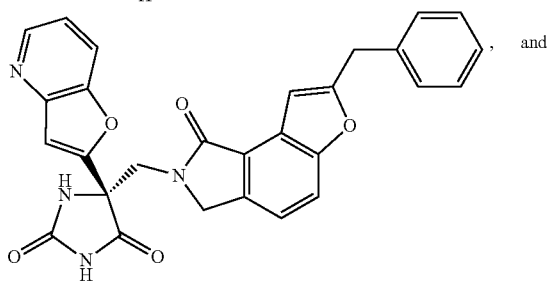

and

-continued

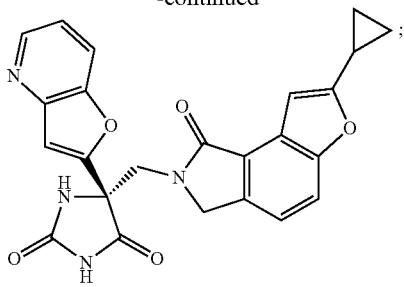

or a pharmaceutically acceptable salt thereof.

5. A compound represented by Formula (III)

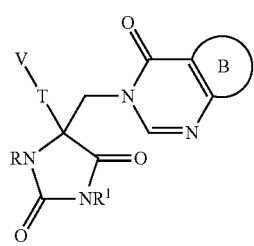

Formula (III)

or a pharmaceutically acceptable salt thereof, wherein:
ring B is aryl or heteroaryl, wherein said aryl or heteroaryl is unsubstituted or substituted with alkoxy;
at least one of T and V is present;
T is absent or present, and if present, is selected from the group consisting of alkyl, alkenyl, alkynyl, cycloalkyl, cycloalkenyl, aryl, heterocyclyl, heterocyclenyl, and heteroaryl;
V is absent or present, and if present, is selected from the group consisting of alkyl, alkenyl, alkynyl, cycloalkyl, cycloalkenyl, aryl, heterocyclyl, heterocyclenyl, and heteroaryl;
R is selected from the group consisting of H, alkyl, cycloalkyl, cycloalkenyl, heterocyclyl, heterocyclenyl, aryl, heteroaryl, —C(═O)alkyl, —C(═O)cycloalkyl, —C(═O)heterocyclyl, —C(═O)aryl, —C(═O)heteroaryl, —C(═O)O-alkyl, —C(═O)O-cycloalkyl, —C(═O)O-heterocyclyl, —C(═O)O-aryl, and —C(═O)O-heteroaryl;
$R^1$ is selected from the group consisting of H and —C($R^3$)$_2$-(Q)$_n R^4$;
each $R^3$ independently is selected from the group consisting of H, alkyl and aryl;
$R^4$ is selected from the group consisting of H, alkyl, heterocyclyl, aryl, heteroaryl, —C(═O)N($R^5$)$_2$, —C(═O)-alkyl, C(═O)-cycloalkyl, C(═O)-heterocyclyl, —C(═O)-aryl, —C(═O)-heteroaryl, —C(═O)—O-alkyl, —C(═O)—O-cycloalkyl, —C(═O)—O-heterocyclyl, —C(═O)—O-aryl, —C(═O)—O-heteroaryl, —P(═O)(—OH)$_2$, —P(═O)(—O-alkyl)$_2$, wherein when each of said "cycloalkyl", "heterocyclyl", "aryl", or "heteroaryl" in any of the aforementioned $R^9$ groups contains two radicals on adjacent carbon atoms, said radicals may optionally be taken together with the carbon atoms to which they are attached to form a five-or six-membered cycloalkyl, aryl, heterocyclyl or heteroaryl ring;

Q is selected from the group consisting of —NR$^5$—, —O—, —S—, —S(O)—, and —S(O)$_2$—;
each $R^5$ is independently selected from the group consisting of H and alkyl;
and n is 0 or 1.

6. The compound of claim 5, selected from the group consisting of:

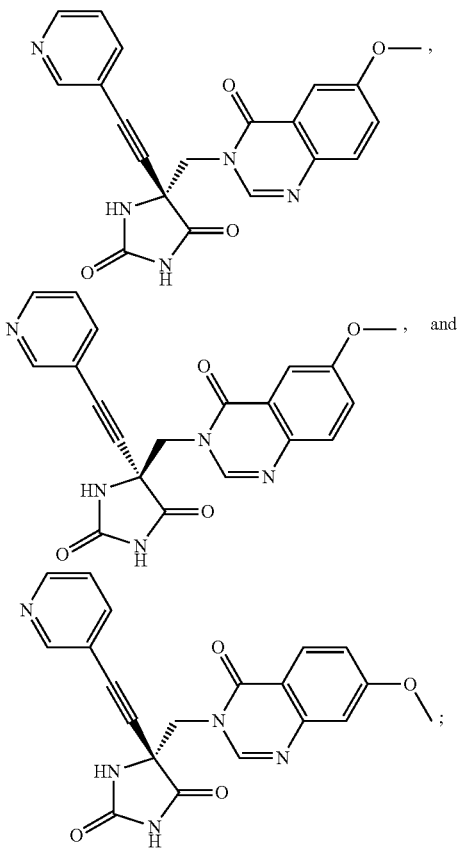

or a pharmaceutically acceptable salt thereof.

7. A compound represented by Formula (IV):

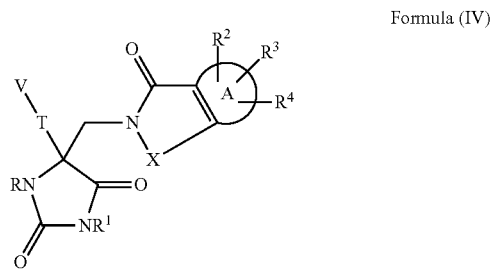

Formula (IV)

or a pharmaceutically acceptable salt thereof, wherein:
ring A is aryl or heteroaryl, substituted on adjacent ring atoms with $R^2$, $R^3$, and $R^4$;
at least one of T and V is present;
T is absent or present, and if present, is selected from the group consisting of alkyl, alkenyl, alkynyl, cycloalkyl, cycloalkenyl, aryl, heterocyclyl, heterocyclenyl, and heteroaryl;

V is absent or present, and if present, is selected from the group consisting of alkyl, alkenyl, alkynyl, cycloalkyl, cycloalkenyl, aryl, heterocyclyl, heterocyclenyl, and heteroaryl;

X is selected from the group consisting of —S—, —O—, —S(O)$_2$—, —S(O)—, —(CR$^5$$_2$)$_p$- and —N(R')—;

p is 1 to 3;

R' is selected from the group consisting of H, alkyl, and aryl;

R is selected from the group consisting of H, alkyl, cycloalkyl, cycloalkenyl, heterocyclyl, heterocyclenyl, aryl, heteroaryl, —C(=O)alkyl, —C(=O)cycloalkyl, —C(=O)heterocyclyl, —C(=O)aryl, —C(=O)heteroaryl, —C(=O)O-alkyl, —C(=O)O-cycloalkyl, —C(=O)O-heterocyclyl, —C(=O)O-aryl, and —C(=O)O-heteroaryl;

R$^1$ is selected from the group consisting of H and —C(R$^6$)$_2$-(Q)$_n$R$^7$;

R$^2$, R$^3$, and R$^4$ are substituents on adjacent ring atoms, wherein each of R$^2$, R$^3$, and R$^4$ is independently selected from the group consisting of halo, alkyl, and alkoxy;

each R$^5$ independently is selected from the group consisting of H, alkyl, and aryl;

each R$^6$ independently is selected from the group consisting of H, alkyl, and aryl;

R$^7$ is selected from the group consisting of H, alkyl, heterocyclyl, aryl, heteroaryl, —C(=O)N(R$^8$)$_2$, —C(=O)-alkyl, C(=O)-cycloalkyl, C(=O)-heterocyclyl, —C(=O)-aryl, —C(=O)-heteroaryl, —C(=O)—O-alkyl, —C(=O)—O-cycloalkyl, —C(=O)—O-heterocyclyl, —C(=O)—O-aryl, —C(=O)—O-heteroaryl, —P(=O)(—OH)$_2$, —P(=O)(—O-alkyl)$_2$, wherein when each of said "cycloalkyl", "heterocyclyl", "aryl", or "heteroaryl" in any of the aforementioned R$^9$ groups contains two radicals on adjacent carbon atoms, said radicals may optionally be taken together with the carbon atoms to which they are attached to form a five- or six-membered cycloalkyl, aryl, heterocyclyl or heteroaryl ring;

Q is selected from the group consisting of —NR$^8$—, —O—, —S—, —S(O)—, and —S(O)$_2$—;

each R$^8$ is independently selected from the group consisting of H and alkyl; and n is 0 or 1.

8. The compound of claim 7, selected from the group consisting of:

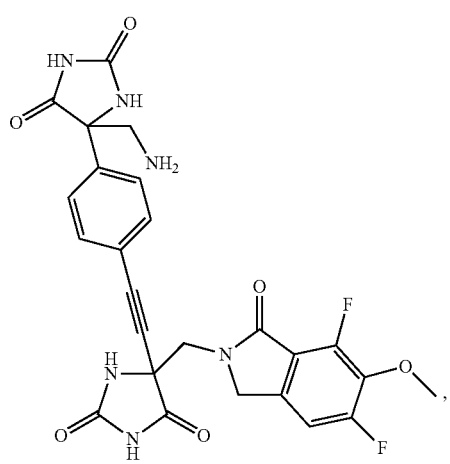

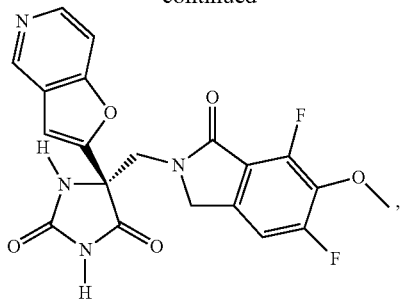

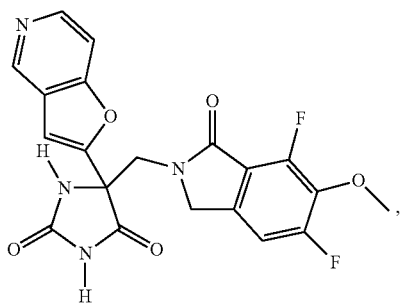

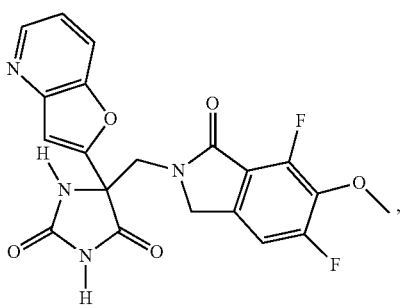

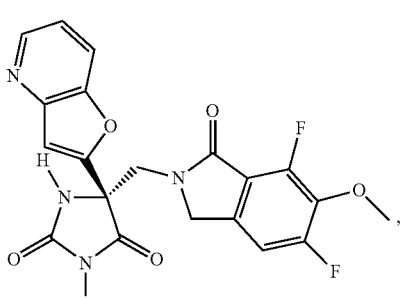

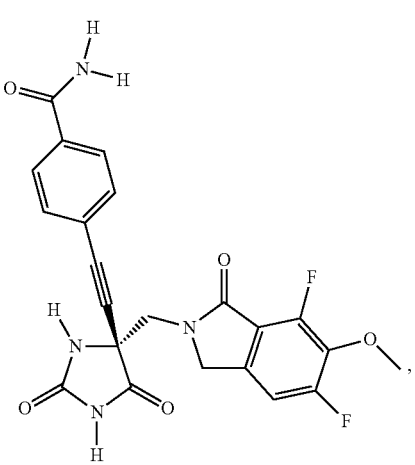

-continued

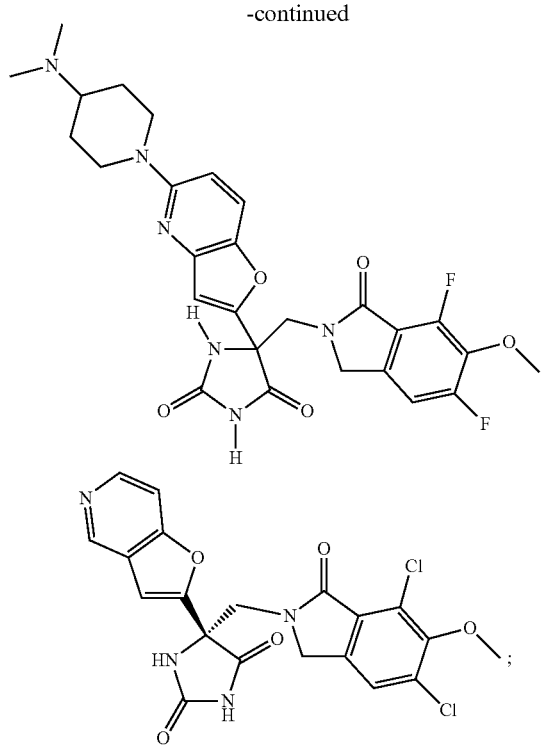

or a pharmaceutically acceptable salt thereof.

9. A compound represented by Formula (V):

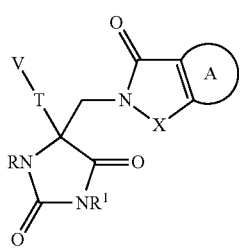

Formula (V)

or a pharmaceutically acceptable salt thereof, wherein:
ring A is aryl or heteroaryl, wherein said aryl or heteroaryl is unsubstituted or substituted with alkoxy or deuterium;
at least one of T and V is present, and at least one of T and V is substituted with 1-3 $R^2$ substituents;
T is absent or present, and if present is selected from the group consisting of: alkyl, alkenyl, alkynyl, cycloalkyl, cycloalkenyl, aryl, heterocyclyl, heterocyclenyl, and heteroaryl;
V is absent or present, and if present is selected from the group consisting of: alkyl, alkenyl, alkynyl, cycloalkyl, cycloalkenyl, aryl, heterocyclyl, heterocyclenyl, and heteroaryl;
X is selected from the group consisting of —S—, —O—, —S(O)$_2$—, —S(O)—, —(CR$^7$$_2$)$_p$-and —N(R')—;
p is 1 to 3;
R' is selected from the group consisting of H, alkyl, and aryl;
R is selected from the group consisting of H, alkyl, cycloalkyl, cycloalkenyl, heterocyclyl, heterocyclenyl, aryl, heteroaryl, —C(=O)alkyl, —C(=O)cycloalkyl, —C(=O)heterocyclyl, —C(=O)aryl, —C(=O)heteroaryl, —C(=O)O-alkyl, —C(=O)O-cycloalkyl, —C(=O)O-heterocyclyl, —C(=O)O-aryl, and —C(=O)O-heteroaryl;
$R^1$ is selected from the group consisting of H and —C(R$^6$)$_2$-(Q)$_n$R$^9$;
Q is selected from the group consisting of —NR$^6$-, —O—, —S—, —S(O)—, and —S(O)$_2$—; and
n is 0 or 1;
$R^2$ is selected from the group consisting of deuterium, —C(=N—OH)—N(R$^6$)$_2$, —C(=O)NR$^6$S(=O)$_2$N(R$^6$)$_2$, —C(R$^6$)((C=O)OR$^6$)-heterocyclyl—C(=O)OR$^6$, —C(R$^6$)((C=O)N(R$^6$)$_2$)-heterocyclyl—C(=O)Oalkyl, —C(=NR$^6$)—N(R$^6$)OR$^6$, —C(=NR$^6$)—N(R$^6$)-heterocyclyl, —C(=NR$^6$)—N(R$^6$)-aryl, —C(=NR$^6$)—N(R$^6$)-heteroaryl, —C(=NR$^6$)—N(R$^6$)$_2$, and —NR$^6$—C(=S)N(R$^6$)-alkyl-heterocyclyl;
each $R^6$ independently is H or alkyl;
each $R^7$ independently is H, alkyl, or aryl;
$R^9$ is selected from the group consisting of H, alkyl, heterocyclyl, aryl, heteroaryl, —C(=O)N(R$^6$)$_2$, —C(=O)-alkyl, C(=O)-cycloalkyl, C(=O)-heterocyclyl, —C(=O)-aryl, —C(=O)-heteroaryl, —C(=O)—O-alkyl, —C(=O)—O-cycloalkyl, —C(=O)—O-heterocyclyl, —C(=O)—O-aryl, —C(=O)—O-heteroaryl, —P(=O)(—OH)$_2$, —P(=O)(—O-alkyl)$_2$, wherein when each of said "cycloalkyl", "heterocyclyl", "aryl", or "heteroaryl" in any of the aforementioned $R^9$ groups contains two radicals on adjacent carbon atoms, said radicals may optionally be taken together with the carbon atoms to which they are attached to form a five-or six-membered cycloalkyl, aryl, heterocyclyl or heteroaryl ring.

10. The compound of claim 9, selected from the group consisting of:

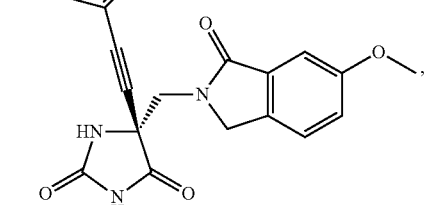

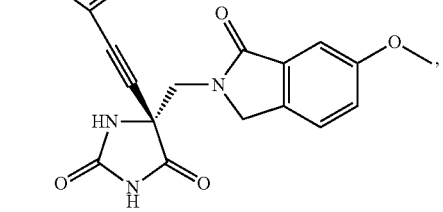

141
-continued
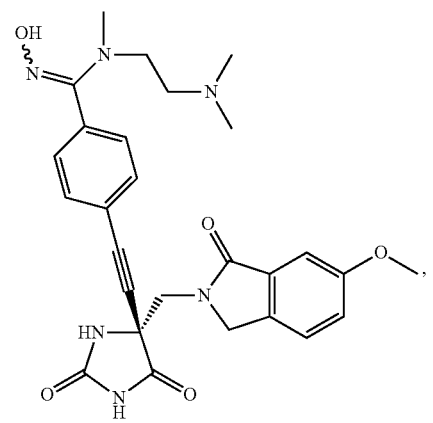
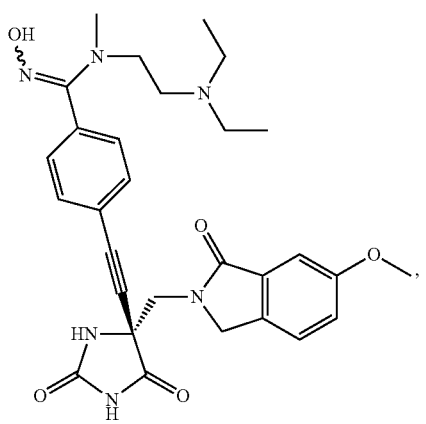
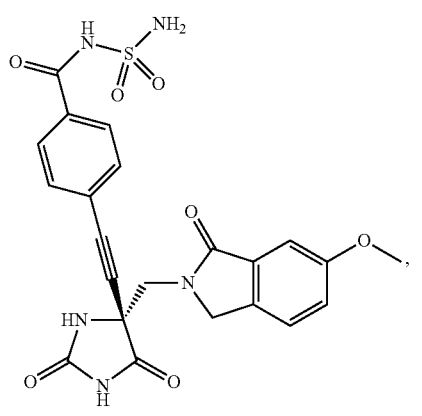
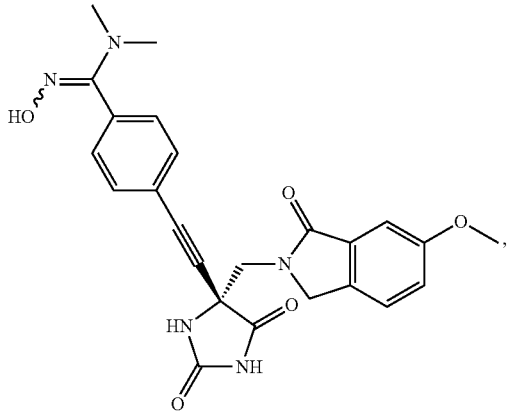
142
-continued
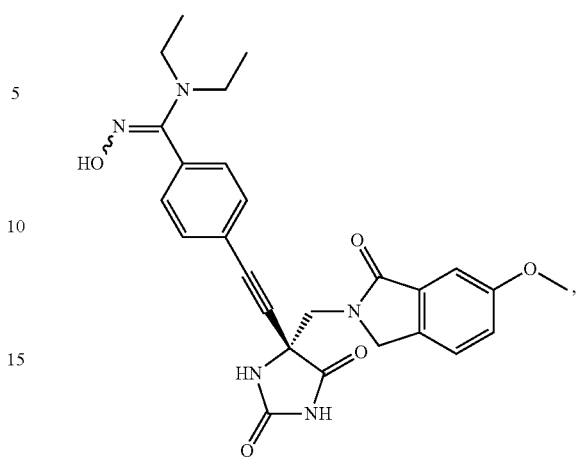
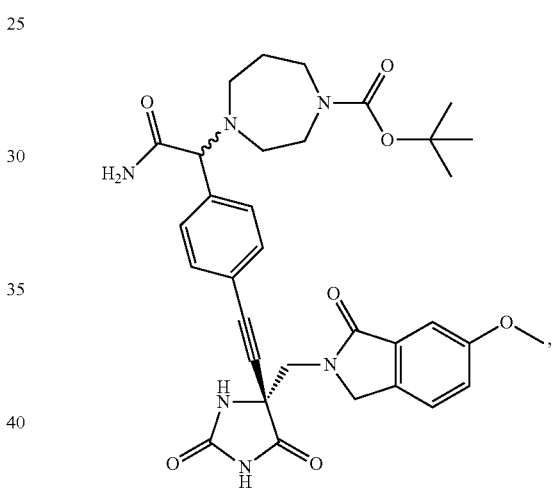
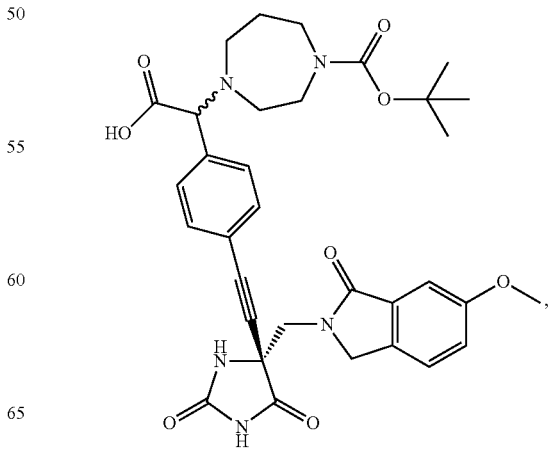

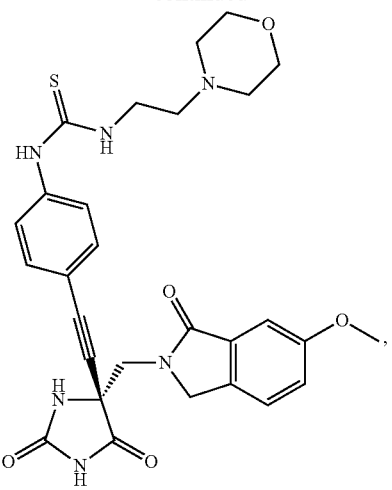

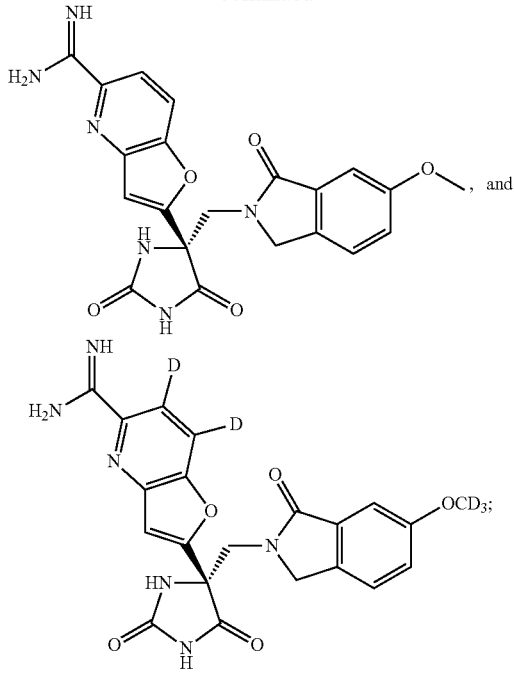

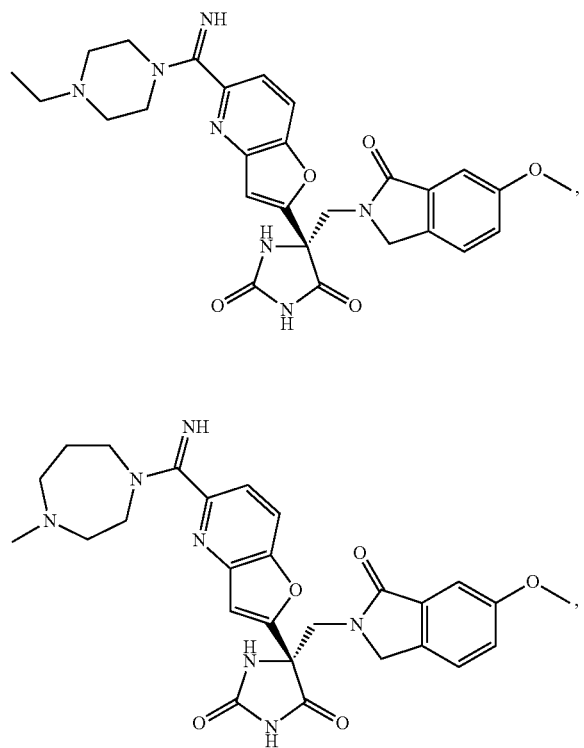

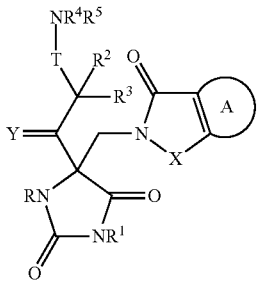

or a pharmaceutically acceptable salt thereof.

11. A compound represented by Formula (VI):

Formula (VI)

or a pharmaceutically acceptable salt thereof; wherein:
ring A is aryl or heteroaryl, where said aryl or heteroaryl is unsubstituted or is substituted with one or two substituents selected from the group consisting of halo and alkoxy;
X is selected from the group consisting of —S—, —O—, —S(O)$_2$—, —S(O)—, —(CR$^7_2$)$_p$— and —N(R')—;
p is 1 to 3;
Y is O or S;
T is aryl or heteroaryl;
R' is selected from the group consisting of H, alkyl, and aryl;
R is selected from the group consisting of H, alkyl, cycloalkyl, cycloalkenyl, heterocyclyl, heterocyclenyl, aryl, heteroaryl, —C(=O)alkyl, —C(=O)cycloalkyl, —C(=O)heterocyclyl, —C(=O)aryl, —C(=O)heteroaryl, —C(=O)O-alkyl, —C(=O)O-cycloalkyl, —C(=O)O-heterocyclyl, —C(=O)O-aryl, and —C(=O)O-heteroaryl;
R$^1$ is selected from the group consisting of H and —C(R$^6$)$_2$-(Q)$_n$R$^9$,
Q is selected from the group consisting of —NR$^6$—, —O—, —S—, —S(O)—, and —S(O)$_2$—, n is 0 or 1;

each of $R^1$ and $R^2$ is independently H or alkyl;

each of $R^4$ and $R^5$ is independently selected from the group consisting of H, alkyl, cycloalkyl, heterocyclyl, aryl, and heteroaryl;

or wherein $R^4$ and $R^5$ together with the nitrogen atom to which they are shown attached form a heterocyclyl or heteroaryl ring;

each $R^6$ independently is H or alkyl;

each $R^7$ independently is H, alkyl or aryl; and $R^9$ is selected from the group consisting of H, alkyl, heterocyclyl, aryl, heteroaryl, —C(=O)N($R^6$)$_2$, —C(=O)-alkyl, C(=O)-cycloalkyl, C(=O)-heterocyclyl, —C(=O)-aryl, —C(=O)-heteroaryl, —C(=O)—O-alkyl, —C(=O)—O-cycloalkyl, —C(=O)—O-heterocyclyl, —C(=O)—O-aryl, —C(=O)—O-heteroaryl, —P(=O)(—OH)$_2$, —P(=O)(—O-alkyl)$_2$, wherein when each of said "cycloalkyl", "heterocyclyl", "aryl", or "heteroaryl" in any of the aforementioned $R^9$ groups contains two radicals on adjacent carbon atoms, said radicals may optionally be taken together with the carbon atoms to which they are attached to form a five-or six-membered cycloalkyl, aryl, heterocyclyl or heteroaryl ring.

12. The compound of claim 11, selected from the group consisting of:

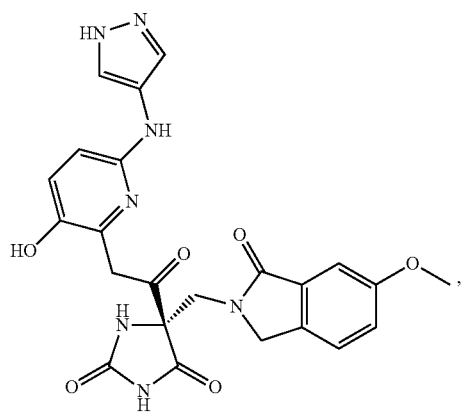

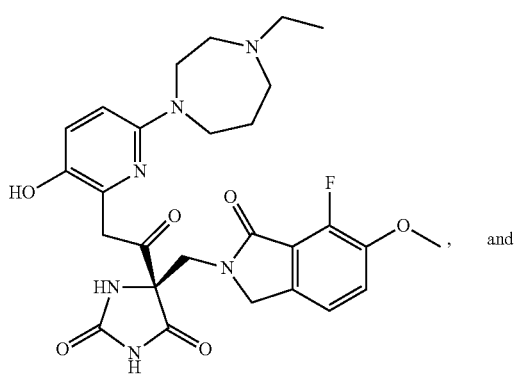

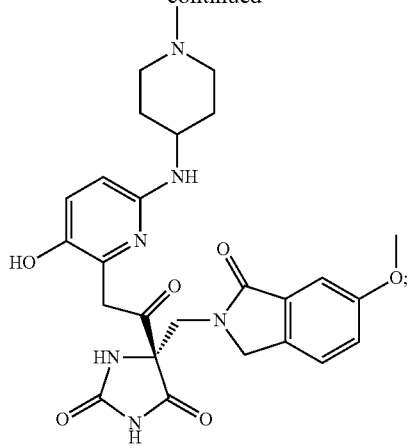

or a pharmaceutically acceptable salt thereof.

13. A compound represented by Formula (VII):

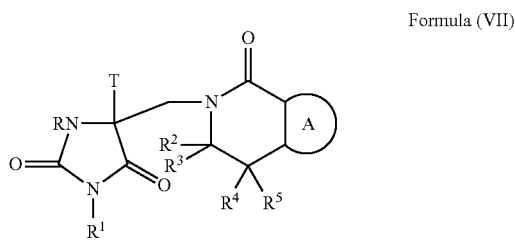

Formula (VII)

or a pharmaceutically acceptable salt thereof; wherein:
ring A is aryl, wherein said aryl is unsubstituted or substituted with alkoxy;

T is heteroaryl, wherein when said T heteroaryl contains two radicals on adjacent carbon atoms, said radicals may optionally be taken together with the carbon atoms to which they are attached to form a five-to eight membered heterocyclyl ring;

R is selected from the group consisting of H, alkyl, cycloalkyl, cycloalkenyl, heterocyclyl, heterocyclenyl, aryl, heteroaryl, —C(=O)alkyl, —C(=O)cycloalkyl, —C(=O)heterocyclyl, —C(=O)aryl, —C(=O)heteroaryl, —C(=O)O-alkyl, —C(=O)O-cycloalkyl, —C(=O)O-heterocyclyl, —C(=O)O-aryl, and —C(=O)O-heteroaryl;

$R^1$ is selected from the group consisting of H and —C($R^6$)$_2$-(Q)$_n$$R^7$;

each of $R^2$, $R^3$, $R^4$, and $R^5$ independently is H or alkyl;

each $R^6$ independently is H or alkyl;

$R^7$ is selected from the group consisting of H, alkyl, heterocyclyl, aryl, heteroaryl, —C(=O)N($R^6$)$_2$, —C(=O)-alkyl, C(=O)-cycloalkyl, C(=O)-heterocyclyl, —C(=O)-aryl, —C(=O)-heteroaryl, —C(=O)—O-alkyl, —C(=O)—O-cycloalkyl, —C(=O)—O-heterocyclyl, —C(=O)—O-aryl, —C(=O)—O-heteroaryl, —P(=O)(—OH)$_2$, —P(=O)(—O-alkyl)$_2$, wherein when each of said "cycloalkyl", "heterocyclyl", "aryl", or "heteroaryl" in any of the aforementioned $R^7$ groups contains two radicals on adjacent carbon atoms, said radicals may optionally be taken together with the carbon atoms to which they are attached to form a five-or six-membered cycloalkyl, aryl, heterocyclyl or heteroaryl ring; and Q is selected from the group consisting of —NR⁶—, —O—, —S—, —S(O)—, and —S(O)₂—; and n is 0 or 1.

14. The compound of claim 13, selected from the group consisting of:

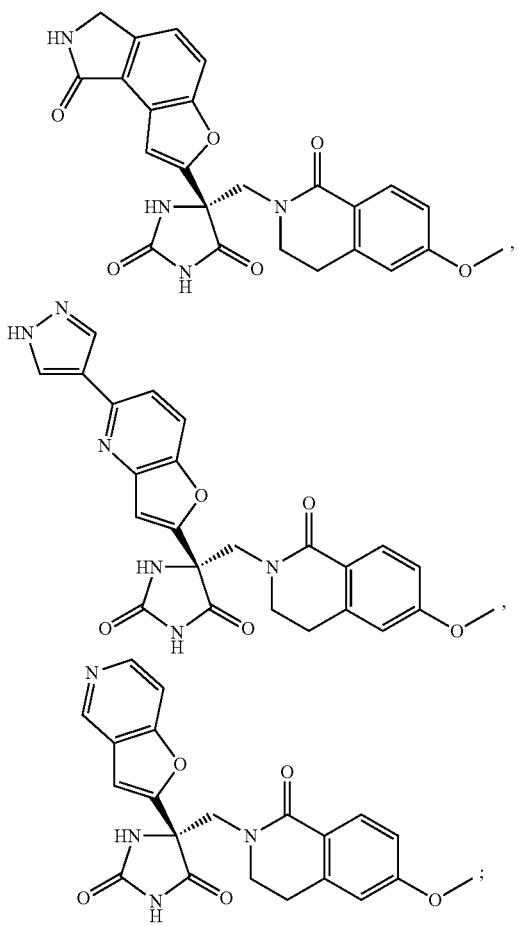

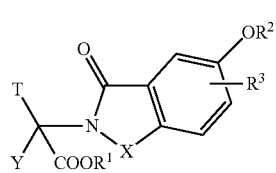

or a pharmaceutically acceptable salt thereof.

15. A compound represented by Formula (VIII)

Formula (VIII)

or a pharmaceutically acceptable salt thereof; wherein:

X is selected from the group consisting of —S—, —O—, —S(O)₂—, —S(O)—, —(CR⁷₂)$_p$—and —N(R')—;

R' is selected from the group consisting of H, alkyl, and aryl;

T is heteroaryl, wherein said heteroaryl is unsubstituted or substituted with a halo;

Y is selected from the group consisting of —OR⁶, —N(R⁶)₂, and —NR⁶—C(=O)N(R⁶)₂;

each of R¹ and R² is independently H or alkyl;

R³ is selected from the group consisting of H or halo;

each R⁶ independently is H or alkyl;

each R⁷ independently is H, alkyl or aryl;

and p is 1-3.

16. The compound of claim 15, selected from the group consisting of:

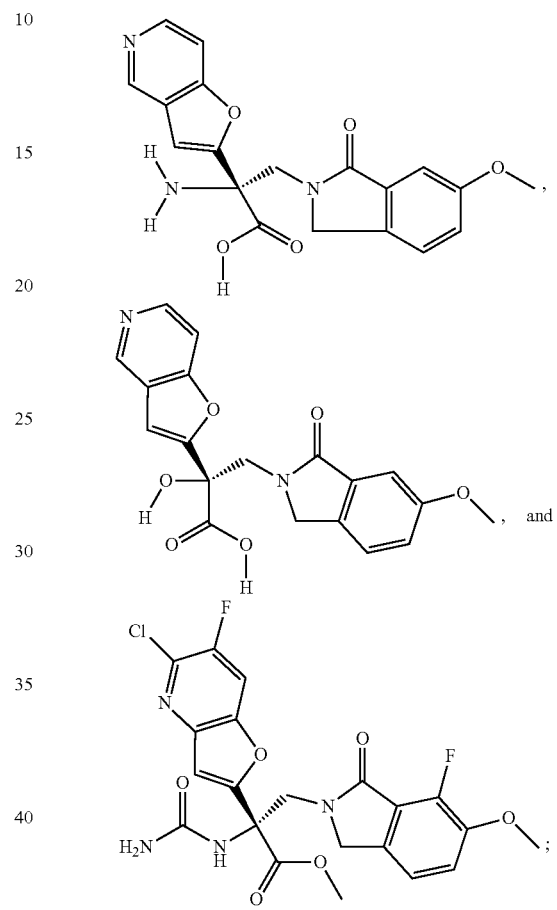

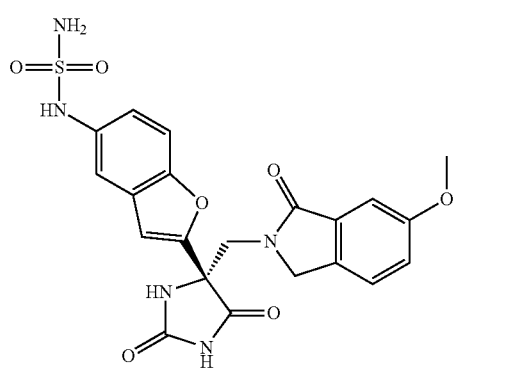

or a pharmaceutically acceptable salt thereof.

17. A compound represented by Formula (IX):

Formula (IX)

or a pharmaceutically acceptable salt thereof.

18. A compound selected from the group consisting of:
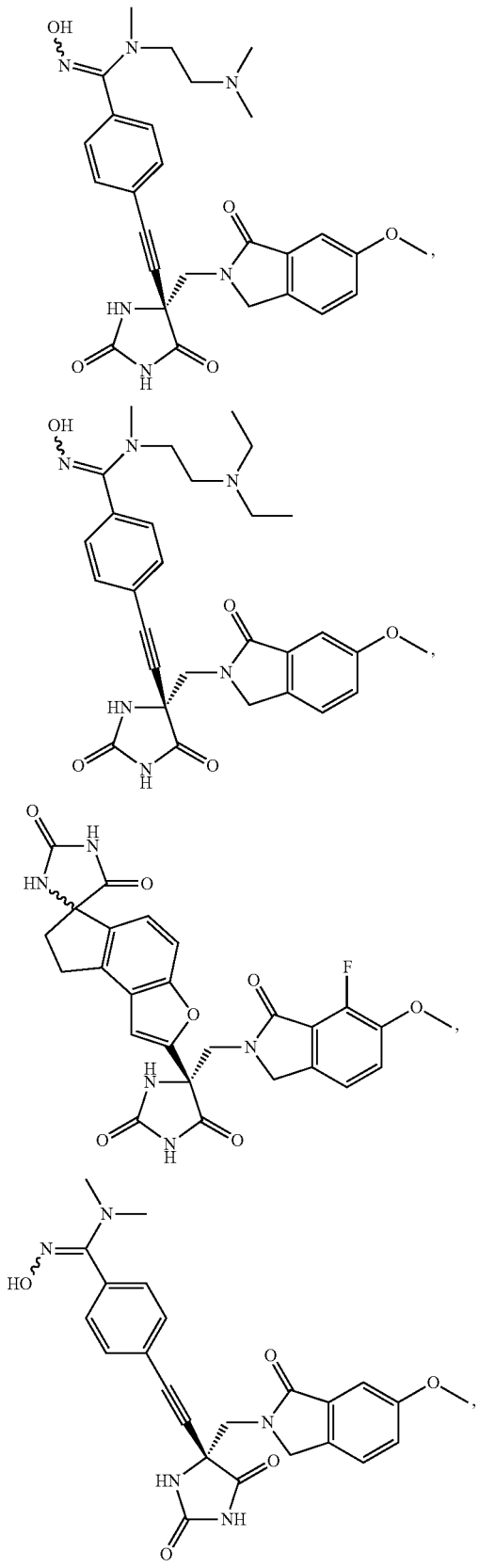
-continued
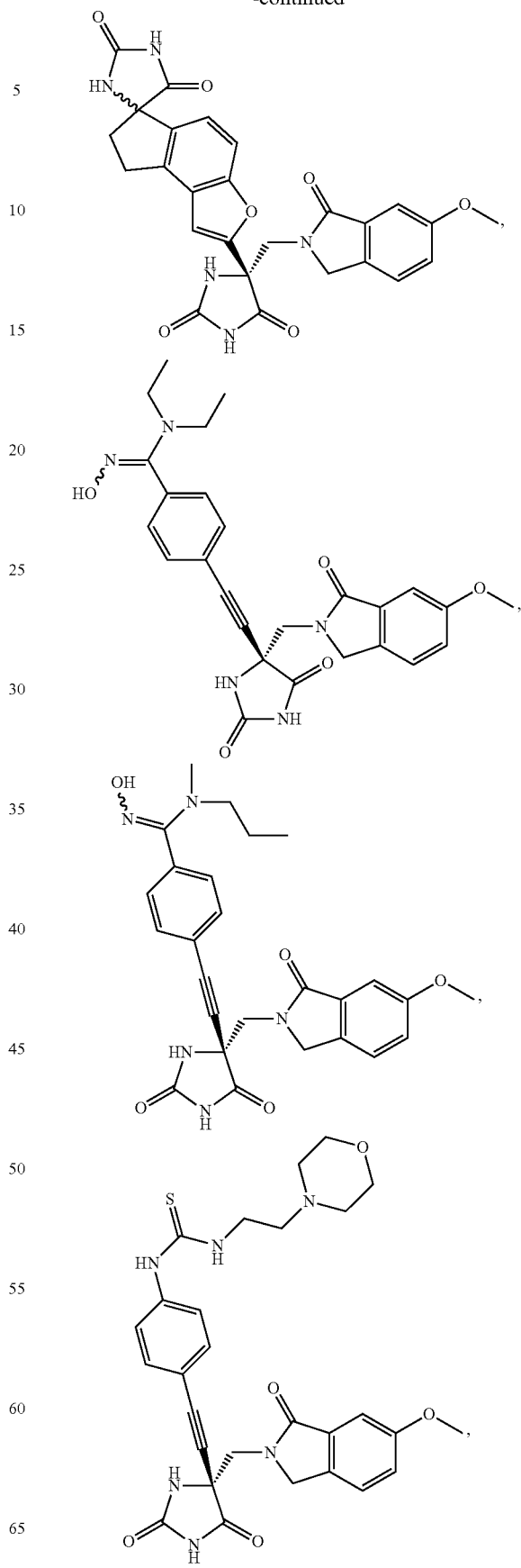

151
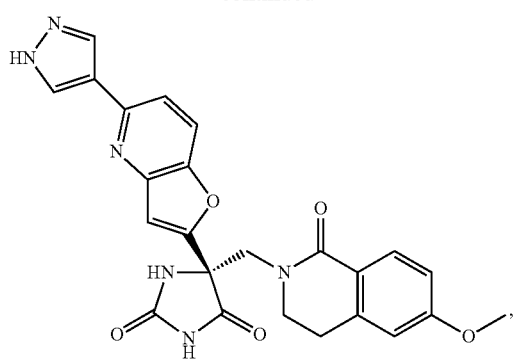
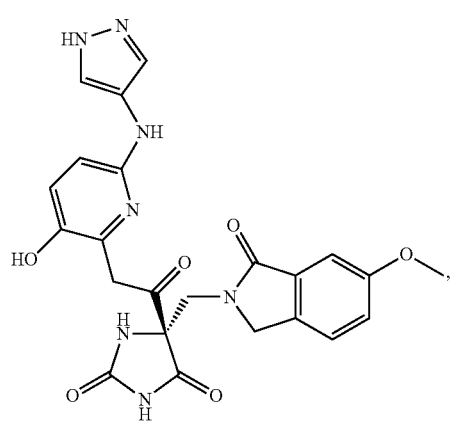
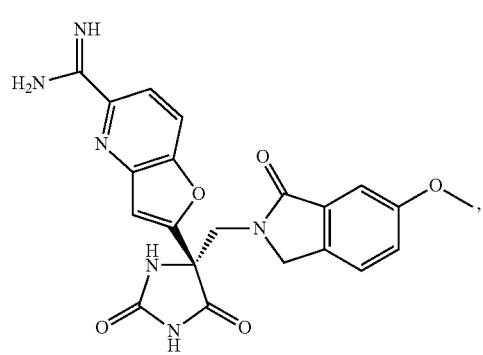
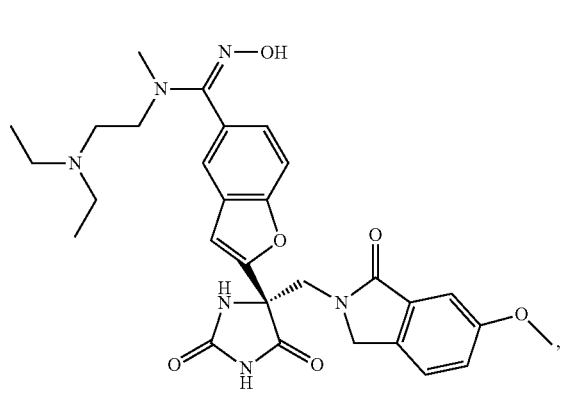
152
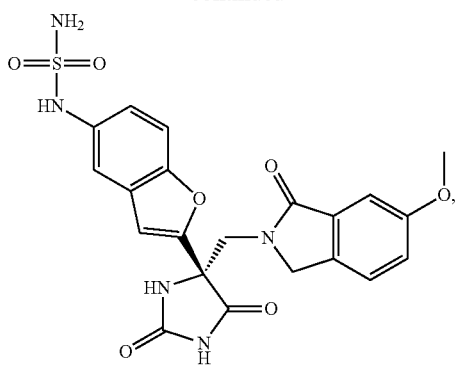
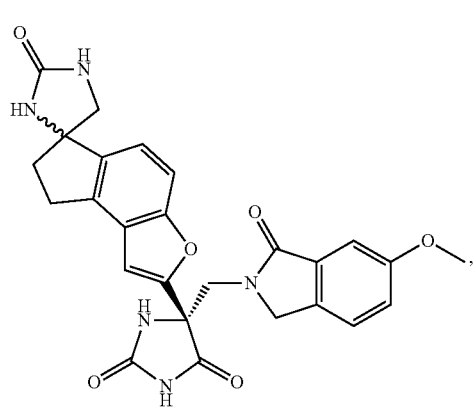
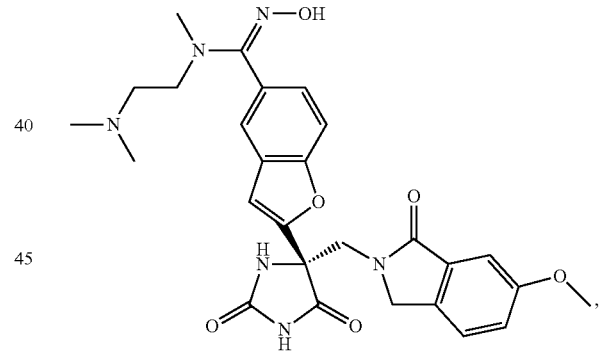
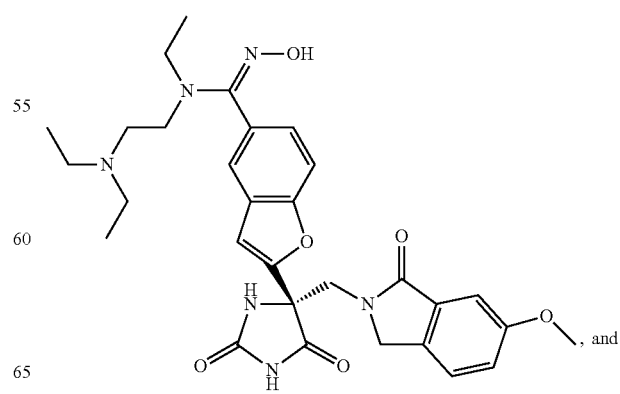
, and -continued
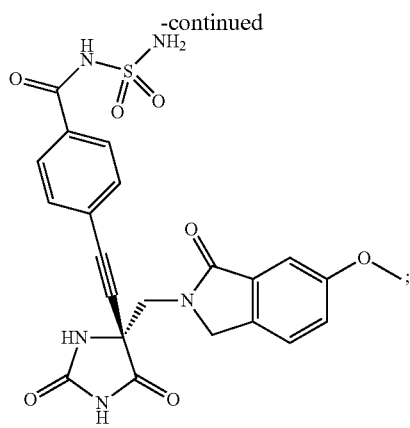
or a pharmaceutically acceptable salt thereof.
19. A pharmaceutical composition comprising a compound of claim 1, or a pharmaceutically acceptable salt thereof, and at least one pharmaceutically acceptable carrier.
* * * * *

UNITED STATES PATENT AND TRADEMARK OFFICE
CERTIFICATE OF CORRECTION

| | | |
|---|---|---|
| PATENT NO. | : 8,450,355 B2 | Page 1 of 1 |
| APPLICATION NO. | : 13/120730 | |
| DATED | : May 28, 2013 | |
| INVENTOR(S) | : Wong et al. | |

It is certified that error appears in the above-identified patent and that said Letters Patent is hereby corrected as shown below:

On the title page in item (75) in the Inventors field:

Please replace "Aneta Maria Kosinzki" with

-- Aneta Maria Kosinski --

Signed and Sealed this
Twenty-seventh Day of May, 2014

Michelle K. Lee
*Deputy Director of the United States Patent and Trademark Office*